(12) United States Patent
Yamanaka

(10) Patent No.: US 7,964,401 B2
(45) Date of Patent: Jun. 21, 2011

(54) SCREENING METHOD FOR SOMATIC CELL NUCLEAR REPROGRAMMING SUBSTANCE AFFECTING ECAT2 AND ECAT3

(75) Inventor: Shinya Yamanaka, Osaka (JP)

(73) Assignees: Kyoto University, Kyoto-shi (JP); Dainippon Sumitomo Pharma Co., Ltd., Osaka-shi (JP)

( * ) Notice: Subject to any disclaimer, the term of this patent is extended or adjusted under 35 U.S.C. 154(b) by 866 days.

(21) Appl. No.: 10/589,905

(22) PCT Filed: Feb. 16, 2005

(86) PCT No.: PCT/JP2005/002842
§ 371 (c)(1),
(2), (4) Date: Dec. 5, 2006

(87) PCT Pub. No.: WO2005/080598
PCT Pub. Date: Sep. 1, 2005

(65) Prior Publication Data
US 2008/0274914 A1 Nov. 6, 2008

(30) Foreign Application Priority Data

Feb. 19, 2004 (JP) ................................ 2004-042337
Aug. 10, 2004 (JP) ................................ 2004-232961
Sep. 24, 2004 (JP) ................................ 2004-276572

(51) Int. Cl.
*C12N 5/02* (2006.01)
*C12N 5/04* (2006.01)
*C12N 15/00* (2006.01)

(52) U.S. Cl. ........ 435/377; 435/354; 435/363; 435/366; 435/373; 435/455; 435/456

(58) Field of Classification Search .................. None
See application file for complete search history.

(56) References Cited

U.S. PATENT DOCUMENTS

| | | | |
|---|---|---|---|
| 2004/0137460 A1 | 7/2004 | Yamanaka et al. | |
| 2006/0281179 A1 | 12/2006 | Sasai et al. | |
| 2008/0003560 A1 | 1/2008 | Nakatsuji et al. | |
| 2008/0280362 A1* | 11/2008 | Jaenisch et al. | 435/455 |

FOREIGN PATENT DOCUMENTS

| | | |
|---|---|---|
| JP | 9-500004 A | 1/1997 |
| JP | 2002-065261 A | 3/2002 |
| JP | 2002-512787 A | 5/2002 |
| JP | 2003-009854 A | 1/2003 |
| JP | 2003-506075 A | 2/2003 |
| JP | 2005-095027 A | 4/2005 |
| WO | 94/24274 A1 | 10/1994 |
| WO | 99/55841 A2 | 11/1999 |
| WO | WO 00/18885 A1 | 4/2000 |
| WO | 01/11011 A2 | 2/2001 |
| WO | WO 01/51616 A2 | 7/2001 |
| WO | WO 02/061033 A2 | 8/2002 |
| WO | WO 02/097090 A1 | 12/2002 |
| WO | 03/027278 A1 | 4/2003 |
| WO | 03/042384 A1 | 5/2003 |
| WO | 03/083089 A2 | 10/2003 |
| WO | 03/095628 A2 | 11/2003 |

OTHER PUBLICATIONS

Mitsui et al. The Homeoprotein Nanog is Required for Maintenance of Pluripotency in Mouse Epiblast and ES Cells. Cell. May 30, 2003, vol. 113, pp. 631-642.*
Chambers et al. Functional Expression Cloning of Nanog, a Pluripotency Sustaining Factor in Embryonic Stem Cells. Cell. May 30, 2003, vol. 113, p. 643-655.*
Ying et al. Conversion of embryonic stem cells to neuroectodermal precursors in adherent monoculture. Nature Biotechnology, Apr. 2003, vol. 21, pp. 183-186.*
Ying et al. Changing potency by spontaneous Fusion. Nature, Apr. 2002, vol. 416 pp. 545-548.*
Prelle et al. Establishment of Pluripotent Cell Lines from Vertbrate Species—Present Status and Future Prospects. Cells, Tissues, Organs, 1999, vol. 165, pp. 220-236.*
Sedivy et al. Gene Targeting and Somatic Cell Genetics—a rebirth or coming of age?. Trends in Genetics, 1999, vol. 15, pp. 88-90.*
Piedrathita et al. Cloning and Transgenesis in Mammals; Implications for Xenotransplantation. American Journal of Transplantation, 2004, vol. 2004 (suppl. 6), pp. 43-50.*
Williams et al. Evaluation of Gene Targeting by Homologous Recombination in Ovine Somatic Cells. Molecular Reproduction and Development, 2003, vol. 66, pp. 115-125.*
Denning et al. Gene Targeting in Primary Fetal Fibroblasts from Sheep and Pig. Cloning and Stem Cells, 2001, vol. 3, pp. 221-231.*
Mitsui et al., *Cell*, 113: 631-642 (May 30, 2003).
Tada et al., *Current Biology*, 11(19): 1553-1558 (2001).
Takahashi et al., *Nature*, 423: 541-545 (May 29, 2003).
Takeda et al., *Nucleic Acids Research*, 20(17): 4613-4620 (1992).
Tokuzawa et al., *Molecular and Cellular Biology*, 23(8): 2699-2708 (2003).

* cited by examiner

*Primary Examiner* — Deborah Crouch
(74) *Attorney, Agent, or Firm* — Leydig, Voit & Mayer, Ltd.

(57) ABSTRACT

The present invention provides a screening method for somatic cell nuclear reprogramming substances, which comprises (a) a step for bringing into contact with each other a somatic cell comprising a gene wherein a marker gene is present at a position permitting expression control by the expression control region of an ECAT gene, and a test substance, and (b) a step following the aforementioned step (a), for determining the presence or absence of the emergence of cells expressing the marker gene, and selecting a test substance allowing the emergence of the cells as a somatic cell nuclear reprogramming substance candidate, and the like.

15 Claims, 9 Drawing Sheets

NAT1$^{-/-}$(neo/Cre)

| Events | % Gated |
|---|---|
| 8749 | 100.00 |
| 1 | 0.01 |

NAT1$^{-/-}$(neo/Cre)/T$^{CAG-EGFP}$

300 V(DC)

| Events | % Gated |
|---|---|
| 7880 | 100.00 |
| 210 | 2.66 |

500 V(DC)

| Events | % Gated |
|---|---|
| 7877 | 100.00 |
| 147 | 1.87 |

SEQUENCE LISTING

```
<160> NUMBER OF SEQ ID NOS: 50

<210> SEQ ID NO 1
<211> LENGTH: 1623
<212> TYPE: DNA
<213> ORGANISM: Mus musculus
<220> FEATURE:
<221> NAME/KEY: CDS
<222> LOCATION: (50)..(1369)

<400> SEQUENCE: 1
tgactgatct tgagtttgca taggcttcct gcggtgaaac gggtacact atg gcc tct      58
                                                      Met Ala Ser
                                                        1 ctg aag agg ttt cag acg ctc gtg ccc ctg gat cac aaa caa ggt acc      106
Leu Lys Arg Phe Gln Thr Leu Val Pro Leu Asp His Lys Gln Gly Thr
      5                  10                  15 tta ttt gaa att att gga gag ccc aag ttg ccc aag tgg ttc cat gtc      154
Leu Phe Glu Ile Ile Gly Glu Pro Lys Leu Pro Lys Trp Phe His Val
 20                  25                  30                  35 gaa tgc ctg gaa gat cca aaa aga ctg tac gtg gaa cct cgg cta ctg      202
Glu Cys Leu Glu Asp Pro Lys Arg Leu Tyr Val Glu Pro Arg Leu Leu
                  40                  45                  50 gaa atc atg ttt ggt aag gat gga gag cac atc cca cat ctt gaa tct      250
Glu Ile Met Phe Gly Lys Asp Gly Glu His Ile Pro His Leu Glu Ser
              55                  60                  65 atg ttg cac acc ctg ata cat gtg aac gtg tgg ggc cct gaa agg cga      298
Met Leu His Thr Leu Ile His Val Asn Val Trp Gly Pro Glu Arg Arg
          70                  75                  80 gct gag att tgg ata ttc gga ccg ccg cct ttc cga agg gac gtt gac      346
Ala Glu Ile Trp Ile Phe Gly Pro Pro Pro Phe Arg Arg Asp Val Asp
      85                  90                  95 cgg atg ctc act gat ctg gct cac tat tgc cgc atg aaa ctg atg gaa      394
Arg Met Leu Thr Asp Leu Ala His Tyr Cys Arg Met Lys Leu Met Glu
100                 105                 110                 115 ata gag gct ctg gag gct gga gtt gag cgt cgt cgt atg gcg gcc cat      442
Ile Glu Ala Leu Glu Ala Gly Val Glu Arg Arg Arg Met Ala Ala His
                 120                 125                 130 aag gct gcc acc cag cct gct ccc gtg aag gtc cgc gag gct gcc cct      490
Lys Ala Ala Thr Gln Pro Ala Pro Val Lys Val Arg Glu Ala Ala Pro
             135                 140                 145 cgg ccc gct tcc gtg aag gtc cct gag acg gcc acc cag cct gct ccc      538
Arg Pro Ala Ser Val Lys Val Pro Glu Thr Ala Thr Gln Pro Ala Pro
```

```
                 150                 155                 160
gtg aag gtc cgc gag gct gcc cct cag ccc gct ccg gtg cag gag gtc        586
Val Lys Val Arg Glu Ala Ala Pro Gln Pro Ala Pro Val Gln Glu Val
    165                 170                 175 cgc gag gct gcc cct cag cag gct tcc gtg cag gag gag gtc cgc gag        634
Arg Glu Ala Ala Pro Gln Gln Ala Ser Val Gln Glu Glu Val Arg Glu
180                 185                 190                 195 gct gcc acc gag cag gct ccc gtg cag gag gtc cgc gag gct gcc acc        682
Ala Ala Thr Glu Gln Ala Pro Val Gln Glu Val Arg Glu Ala Ala Thr
                200                 205                 210 gag cag gct ccc gtg cag gag gtc agc gag gct gcc acc gag cag gct        730
Glu Gln Ala Pro Val Gln Glu Val Ser Glu Ala Ala Thr Glu Gln Ala
            215                 220                 225 ccc gtg cag gag gtc aac gag gct gcc acc gag cag gct tcc gtg cag        778
Pro Val Gln Glu Val Asn Glu Ala Ala Thr Glu Gln Ala Ser Val Gln
        230                 235                 240 gcg gtc cgc gag gct gcc acc cgg ccg gct ccc ggg aag gtc cgc aag        826
Ala Val Arg Glu Ala Ala Thr Arg Pro Ala Pro Gly Lys Val Arg Lys
    245                 250                 255 gcg gcc acc cag ccg gct ccg gtg cag gtt tgc cag gag gcc acc cag        874
Ala Ala Thr Gln Pro Ala Pro Val Gln Val Cys Gln Glu Ala Thr Gln
260                 265                 270                 275 ttg gct ccc gtg aag gtc cgc gag gcg gcc acc cag ccg gct tcc ggg        922
Leu Ala Pro Val Lys Val Arg Glu Ala Ala Thr Gln Pro Ala Ser Gly
                280                 285                 290 aag gtc cgc gag gcg gcc acc cag ttg gct cct gtg aag gtc cgc aag        970
Lys Val Arg Glu Ala Ala Thr Gln Leu Ala Pro Val Lys Val Arg Lys
            295                 300                 305 gca gcc acc cag ttg gct cct gtg aag gtc cac gag gcg gcc acc cag       1018
Ala Ala Thr Gln Leu Ala Pro Val Lys Val His Glu Ala Ala Thr Gln
        310                 315                 320 ccg gct ccg ggg aag gtc agc gat gct gcc acg cag tcg gct tcg gtg       1066
Pro Ala Pro Gly Lys Val Ser Asp Ala Ala Thr Gln Ser Ala Ser Val
    325                 330                 335 cag gtt cgt gag gct gcc acg cag ctg tct ccc gtg gag gcc act gat       1114
Gln Val Arg Glu Ala Ala Thr Gln Leu Ser Pro Val Glu Ala Thr Asp
340                 345                 350                 355 act agc cag ttg gct cag gtg aag gct gat gaa gcc ttt gcc cag cac       1162
Thr Ser Gln Leu Ala Gln Val Lys Ala Asp Glu Ala Phe Ala Gln His
                360                 365                 370 act tca ggg gag gcc cac cag gtt gcc aat ggg cag tct ccc att gaa       1210
Thr Ser Gly Glu Ala His Gln Val Ala Asn Gly Gln Ser Pro Ile Glu
            375                 380                 385 gtc tgt gag act gcc acc ggg cag cat tct cta gat gtc tct agg gcc       1258
Val Cys Glu Thr Ala Thr Gly Gln His Ser Leu Asp Val Ser Arg Ala
        390                 395                 400 ttg tcc cag aag tgt cct gag gtt ttt gag tgg gag acc cag agt tgt       1306
Leu Ser Gln Lys Cys Pro Glu Val Phe Glu Trp Glu Thr Gln Ser Cys
    405                 410                 415 ttg gat ggc agc tat gtc ata gtt cag cct cca agg gat gcc tgg gaa       1354
Leu Asp Gly Ser Tyr Val Ile Val Gln Pro Pro Arg Asp Ala Trp Glu
420                 425                 430                 435 tca ttt atc ata tta taaatgcatc tctggtgtga gccaggatag atggtacacg       1409
Ser Phe Ile Ile Leu
                440 tctgcaaatc cagaacctaa aggcagggt tagcttgggc tgagtaaggc aatgatctta      1469 aacctcagcc tgcctaagac tcccttcatc tttctttctg gttttgccc taggaatcgg      1529 gaagaacaga gtagagctgt ttttgtttcc ccattgtgtt aaatgtttgc agacacaatt     1589
```

```
taaagtattc taataaaaaa aaaattgcat tccc                              1623
```

<210> SEQ ID NO 2
<211> LENGTH: 440
<212> TYPE: PRT
<213> ORGANISM: Mus musculus

<400> SEQUENCE: 2

```
Met Ala Ser Leu Lys Arg Phe Gln Thr Leu Val Pro Leu Asp His Lys
  1               5                  10                  15

Gln Gly Thr Leu Phe Glu Ile Ile Gly Glu Pro Lys Leu Pro Lys Trp
             20                  25                  30

Phe His Val Glu Cys Leu Glu Asp Pro Lys Arg Leu Tyr Val Glu Pro
         35                  40                  45

Arg Leu Leu Glu Ile Met Phe Gly Lys Asp Gly Glu His Ile Pro His
     50                  55                  60

Leu Glu Ser Met Leu His Thr Leu Ile His Val Asn Val Trp Gly Pro
 65                  70                  75                  80

Glu Arg Arg Ala Glu Ile Trp Ile Phe Gly Pro Pro Phe Arg Arg
                 85                  90                  95

Asp Val Asp Arg Met Leu Thr Asp Leu Ala His Tyr Cys Arg Met Lys
            100                 105                 110

Leu Met Glu Ile Glu Ala Leu Glu Ala Gly Val Glu Arg Arg Arg Met
        115                 120                 125

Ala Ala His Lys Ala Ala Thr Gln Pro Ala Pro Val Lys Val Arg Glu
    130                 135                 140

Ala Ala Pro Arg Pro Ala Ser Val Lys Val Pro Glu Thr Ala Thr Gln
145                 150                 155                 160

Pro Ala Pro Val Lys Val Arg Glu Ala Ala Pro Gln Pro Ala Pro Val
                165                 170                 175

Gln Glu Val Arg Glu Ala Ala Pro Gln Gln Ala Ser Val Gln Glu Glu
            180                 185                 190

Val Arg Glu Ala Ala Thr Glu Gln Ala Pro Val Gln Glu Val Arg Glu
        195                 200                 205

Ala Ala Thr Glu Gln Ala Pro Val Gln Glu Val Ser Glu Ala Ala Thr
    210                 215                 220

Glu Gln Ala Pro Val Gln Glu Val Asn Glu Ala Ala Thr Glu Gln Ala
225                 230                 235                 240

Ser Val Gln Ala Val Arg Glu Ala Ala Thr Arg Pro Ala Pro Gly Lys
                245                 250                 255

Val Arg Lys Ala Ala Thr Gln Pro Ala Pro Val Gln Val Cys Gln Glu
            260                 265                 270

Ala Thr Gln Leu Ala Pro Val Lys Val Arg Glu Ala Ala Thr Gln Pro
        275                 280                 285

Ala Ser Gly Lys Val Arg Glu Ala Ala Thr Gln Leu Ala Pro Val Lys
    290                 295                 300

Val Arg Lys Ala Ala Thr Gln Leu Ala Pro Val Lys Val His Glu Ala
305                 310                 315                 320

Ala Thr Gln Pro Ala Pro Gly Lys Val Ser Asp Ala Ala Thr Gln Ser
                325                 330                 335

Ala Ser Val Gln Val Arg Glu Ala Ala Thr Gln Leu Ser Pro Val Glu
            340                 345                 350

Ala Thr Asp Thr Ser Gln Leu Ala Gln Val Lys Ala Asp Glu Ala Phe
        355                 360                 365

Ala Gln His Thr Ser Gly Glu Ala His Gln Val Ala Asn Gly Gln Ser
```

-continued

```
                    370                 375                 380
Pro Ile Glu Val Cys Glu Thr Ala Thr Gly Gln His Ser Leu Asp Val
385                 390                 395                 400

Ser Arg Ala Leu Ser Gln Lys Cys Pro Glu Val Phe Glu Trp Glu Thr
                405                 410                 415

Gln Ser Cys Leu Asp Gly Ser Tyr Val Ile Val Gln Pro Pro Arg Asp
            420                 425                 430

Ala Trp Glu Ser Phe Ile Ile Leu
            435                 440

<210> SEQ ID NO 3
<211> LENGTH: 1063
<212> TYPE: DNA
<213> ORGANISM: Homo sapiens
<220> FEATURE:
<221> NAME/KEY: CDS
<222> LOCATION: (54)..(704)

<400> SEQUENCE: 3
tcggcctttg ggtttgctgt ggtgtccttg tctcctgcag gaccggccgc agc atg          56
                                                           Met
                                                             1 gac gct ccc agg cgg ttt ccg acg ctc gtg caa ctg atg cag cca aaa        104
Asp Ala Pro Arg Arg Phe Pro Thr Leu Val Gln Leu Met Gln Pro Lys
                5                  10                  15 gca atg cca gtg gag gtg ctc ggt cac ctc cct aag cgg ttc tcc tgg        152
Ala Met Pro Val Glu Val Leu Gly His Leu Pro Lys Arg Phe Ser Trp
             20                  25                  30 ttc cac tct gag ttc ctg aag aat ccg aag gta gtt cgc ctt gag gtt        200
Phe His Ser Glu Phe Leu Lys Asn Pro Lys Val Val Arg Leu Glu Val
         35                  40                  45 tgg ctg gtg gaa aag atc ttc ggc cgg gga gaa cgc atc ccg cac            248
Trp Leu Val Glu Lys Ile Phe Gly Arg Gly Gly Glu Arg Ile Pro His
 50                  55                  60                  65 gtc cag ggt atg tcc caa atc ttg att cac gtg aat cga ttg gac cct        296
Val Gln Gly Met Ser Gln Ile Leu Ile His Val Asn Arg Leu Asp Pro
                 70                  75                  80 aac ggc gag gct gag atc ttg gta ttt ggg agg cct tct tac cag gag        344
Asn Gly Glu Ala Glu Ile Leu Val Phe Gly Arg Pro Ser Tyr Gln Glu
             85                  90                  95 gac aca atc aag atg atc atg aac ctg gct gac tat cac cgc cag ctc        392
Asp Thr Ile Lys Met Ile Met Asn Leu Ala Asp Tyr His Arg Gln Leu
         100                 105                 110 cag gcg aaa ggc tca gga aag gcc ctc gcc cag gat gtc gcc act cag        440
Gln Ala Lys Gly Ser Gly Lys Ala Leu Ala Gln Asp Val Ala Thr Gln
     115                 120                 125 aag gcc gag acc cag cgg tct tca ata gaa gtc cgg gag gcc ggg acg        488
Lys Ala Glu Thr Gln Arg Ser Ser Ile Glu Val Arg Glu Ala Gly Thr
130                 135                 140                 145 cag cgt tcg gtg gag gtc cgg gag gcc ggg acc cag cgt tcg gtg gaa        536
Gln Arg Ser Val Glu Val Arg Glu Ala Gly Thr Gln Arg Ser Val Glu
                 150                 155                 160 gtc cag gag gtc ggg aca cag ggt tct ccg gtg gag gtg cag gag gcc        584
Val Gln Glu Val Gly Thr Gln Gly Ser Pro Val Glu Val Gln Glu Ala
             165                 170                 175 ggg acc cag cag tct ctc cag gct gcc aac aag tcg ggg acc cag cga        632
Gly Thr Gln Gln Ser Leu Gln Ala Ala Asn Lys Ser Gly Thr Gln Arg
         180                 185                 190 tcc ccc gaa gct gcc agc aag gca gtg acc cag cgg ttt cgc gag gat        680
Ser Pro Glu Ala Ala Ser Lys Ala Val Thr Gln Arg Phe Arg Glu Asp
     195                 200                 205
```

```
gcc cgg gac cca gtt act aga tta tgaaggcatc tcaggccctg gagccagagc    734
Ala Arg Asp Pro Val Thr Arg Leu
210                 215 cagtcagggg ttaaagtgaa agcccgtatt tccgcccaga agctggggtt ggggagagga    794
tgtggatttt ttgttttacc ctttctgttg catggttgca aacacaaact tgagttctaa    854
taaagaattg caaagtggaa gcccgccccc ccctccccc cgcctccct taagtccagg       914 aagctggggt ggcgaggaag gatgatgtgg attgttttg ttttacccct tttgttgaat     974
ggttgccaac ccaaacttga gttttaataa ataattgcct ttccaaaaaa aaaaaaaaa    1034 aaaaaaaaa aaaaaaaaa aaaaaaaa                                        1063
```

<210> SEQ ID NO 4
<211> LENGTH: 217
<212> TYPE: PRT
<213> ORGANISM: Homo sapiens

<400> SEQUENCE: 4

```
Met Asp Ala Pro Arg Arg Phe Pro Thr Leu Val Gln Leu Met Gln Pro
1               5                   10                  15

Lys Ala Met Pro Val Glu Val Leu Gly His Leu Pro Lys Arg Phe Ser
            20                  25                  30

Trp Phe His Ser Glu Phe Leu Lys Asn Pro Lys Val Val Arg Leu Glu
        35                  40                  45

Val Trp Leu Val Glu Lys Ile Phe Gly Arg Gly Glu Arg Ile Pro
    50                  55                  60

His Val Gln Gly Met Ser Gln Ile Leu Ile His Val Asn Arg Leu Asp
65                  70                  75                  80

Pro Asn Gly Glu Ala Glu Ile Leu Val Phe Gly Arg Pro Ser Tyr Gln
                85                  90                  95

Glu Asp Thr Ile Lys Met Ile Met Asn Leu Ala Asp Tyr His Arg Gln
            100                 105                 110

Leu Gln Ala Lys Gly Ser Gly Lys Ala Leu Ala Gln Asp Val Ala Thr
        115                 120                 125

Gln Lys Ala Glu Thr Gln Arg Ser Ser Ile Glu Val Arg Glu Ala Gly
    130                 135                 140

Thr Gln Arg Ser Val Glu Val Arg Glu Ala Gly Thr Gln Arg Ser Val
145                 150                 155                 160

Glu Val Gln Glu Val Gly Thr Gln Gly Ser Pro Val Glu Val Gln Glu
                165                 170                 175

Ala Gly Thr Gln Gln Ser Leu Gln Ala Ala Asn Lys Ser Gly Thr Gln
            180                 185                 190

Arg Ser Pro Glu Ala Ala Ser Lys Ala Val Thr Gln Arg Phe Arg Glu
        195                 200                 205

Asp Ala Arg Asp Pro Val Thr Arg Leu
    210                 215
```

<210> SEQ ID NO 5
<211> LENGTH: 591
<212> TYPE: DNA
<213> ORGANISM: Mus musculus
<220> FEATURE:
<221> NAME/KEY: CDS
<222> LOCATION: (59)..(412)

<400> SEQUENCE: 5

```
gccgtgcgtg gtggataagc ttgatctcgt cttccctgaa gtctggttcc ttggcagg      58
```

```
atg atg gtg acc ctc gtg acc cgt aaa gat atc ccc ccg tgg gtg aaa    106
Met Met Val Thr Leu Val Thr Arg Lys Asp Ile Pro Pro Trp Val Lys
 1               5                  10                  15 gtt cct gaa gac ctg aaa gat cca gaa gta ttc cag gtc cag tcg ctg    154
Val Pro Glu Asp Leu Lys Asp Pro Glu Val Phe Gln Val Gln Ser Leu
             20                  25                  30 gtg ctg aaa tat ctg ttt ggc cca cag gga tct cga atg tct cac atc    202
Val Leu Lys Tyr Leu Phe Gly Pro Gln Gly Ser Arg Met Ser His Ile
         35                  40                  45 gag cag gtg agc cag gcc atg ttt gag ctg aag aac ctg gaa tct ccc    250
Glu Gln Val Ser Gln Ala Met Phe Glu Leu Lys Asn Leu Glu Ser Pro
     50                  55                  60 gaa gaa ctt atc gag gtc ttc att tac ggc tct caa aac aac aag att    298
Glu Glu Leu Ile Glu Val Phe Ile Tyr Gly Ser Gln Asn Asn Lys Ile
 65                  70                  75                  80 cgg gct aaa tgg atg ctt cag tcc atg gct gag agg tac cac ctg cgc    346
Arg Ala Lys Trp Met Leu Gln Ser Met Ala Glu Arg Tyr His Leu Arg
                 85                  90                  95 cag caa aaa gga gtg ctg aag ctg gag gaa tcc atg aag acc ctg gag    394
Gln Gln Lys Gly Val Leu Lys Leu Glu Glu Ser Met Lys Thr Leu Glu
            100                 105                 110 cta ggc cag tgt atc gag tgaagccagt ttccagtcct tgtgtctccg           442
Leu Gly Gln Cys Ile Glu
        115 acctggatgc aggttaagct gtggccagtg tttggttctg gcgggatttt tagctttgtt   502 acatcctagc aagatattct ggatccctgc tgcgcattct gatgtgaatc ccaaggttac   562 cactctaaat aaaaaataaa attgaagtg                                    591

<210> SEQ ID NO 6
<211> LENGTH: 118
<212> TYPE: PRT
<213> ORGANISM: Mus musculus

<400> SEQUENCE: 6

Met Met Val Thr Leu Val Thr Arg Lys Asp Ile Pro Pro Trp Val Lys
 1               5                  10                  15

Val Pro Glu Asp Leu Lys Asp Pro Glu Val Phe Gln Val Gln Ser Leu
             20                  25                  30

Val Leu Lys Tyr Leu Phe Gly Pro Gln Gly Ser Arg Met Ser His Ile
         35                  40                  45

Glu Gln Val Ser Gln Ala Met Phe Glu Leu Lys Asn Leu Glu Ser Pro
     50                  55                  60

Glu Glu Leu Ile Glu Val Phe Ile Tyr Gly Ser Gln Asn Asn Lys Ile
 65                  70                  75                  80

Arg Ala Lys Trp Met Leu Gln Ser Met Ala Glu Arg Tyr His Leu Arg
                 85                  90                  95

Gln Gln Lys Gly Val Leu Lys Leu Glu Glu Ser Met Lys Thr Leu Glu
            100                 105                 110

Leu Gly Gln Cys Ile Glu
        115

<210> SEQ ID NO 7
<211> LENGTH: 640
<212> TYPE: DNA
<213> ORGANISM: Homo sapiens
<220> FEATURE:
<221> NAME/KEY: CDS
<222> LOCATION: (15)..(362)

<400> SEQUENCE: 7
```

```
ggcacgagga taag atg gga act ctc ccg gca cgt aga cat atc ccg ccg         50
              Met Gly Thr Leu Pro Ala Arg Arg His Ile Pro Pro
                1               5                  10 tgg gtg aaa gtt ccc gaa gac ctg aaa gat cca gag gtg ttc cag gtc         98
Trp Val Lys Val Pro Glu Asp Leu Lys Asp Pro Glu Val Phe Gln Val
        15                  20                  25 cag acg cgg ctg ctg aaa gcc att ttc ggc ccg gac gga tct cga atc        146
Gln Thr Arg Leu Leu Lys Ala Ile Phe Gly Pro Asp Gly Ser Arg Ile
    30                  35                  40 cct tac atc gag cag gtg agc aag gcc atg ctc gag ctg aag gct ctg        194
Pro Tyr Ile Glu Gln Val Ser Lys Ala Met Leu Glu Leu Lys Ala Leu
45                  50                  55                  60 gag tct tca gac ctc acc gag gtc gtg gtt tac ggc tcc tat ttg tac        242
Glu Ser Ser Asp Leu Thr Glu Val Val Val Tyr Gly Ser Tyr Leu Tyr
                65                  70                  75 aag ctc cgg acc aag tgg atg ctc cag tcc atg gct gag tgg cac cgc        290
Lys Leu Arg Thr Lys Trp Met Leu Gln Ser Met Ala Glu Trp His Arg
            80                  85                  90 cag cgc cag gag cga ggg atg ctc aaa ctt gcc gaa gcc atg aat gcc        338
Gln Arg Gln Glu Arg Gly Met Leu Lys Leu Ala Glu Ala Met Asn Ala
        95                 100                 105 ctc gaa cta ggc cct tgg atg aag tgaaccagtt tccagccaat gcaatgaagc        392
Leu Glu Leu Gly Pro Trp Met Lys
    110                 115 cgggttgcag agattaggtt gtggccagag ctagagtgat tccttaagct tgttttaaaa       452
tctgctccag cctaaagagt taagggaaaa ccatttgttc ccttaaagag ttaagggaaa       512
acccttggct ctgagtcttg ttgtgaatat ttctttgatg attgttaata aaaagtgttt       572 tttcttttt cccattttta aaataacaa taaagtttta aataagttga taaaaaaaaa         632
aaaaaaaa                                                                640

<210> SEQ ID NO 8
<211> LENGTH: 116
<212> TYPE: PRT
<213> ORGANISM: Homo sapiens

<400> SEQUENCE: 8

Met Gly Thr Leu Pro Ala Arg Arg His Ile Pro Pro Trp Val Lys Val
  1               5                  10                  15

Pro Glu Asp Leu Lys Asp Pro Glu Val Phe Gln Val Gln Thr Arg Leu
             20                  25                  30

Leu Lys Ala Ile Phe Gly Pro Asp Gly Ser Arg Ile Pro Tyr Ile Glu
         35                  40                  45

Gln Val Ser Lys Ala Met Leu Glu Leu Lys Ala Leu Glu Ser Ser Asp
     50                  55                  60

Leu Thr Glu Val Val Val Tyr Gly Ser Tyr Leu Tyr Lys Leu Arg Thr
 65                  70                  75                  80

Lys Trp Met Leu Gln Ser Met Ala Glu Trp His Arg Gln Arg Gln Glu
                 85                  90                  95

Arg Gly Met Leu Lys Leu Ala Glu Ala Met Asn Ala Leu Glu Leu Gly
            100                 105                 110

Pro Trp Met Lys
        115

<210> SEQ ID NO 9
<211> LENGTH: 1670
<212> TYPE: DNA
<213> ORGANISM: Mus musculus
```

```
<220> FEATURE:
<221> NAME/KEY: CDS
<222> LOCATION: (134)..(1567)

<400> SEQUENCE: 9
acttgcctgt ccaagatctg ttggaatctg cttctacaga agaccagctg aaacaaatag      60
cttcgtggga ctgagcacaa ctactagatt cttggacttc cgttcacagc tgccaattgt     120
tgggagtaca ata atg gag gag tcg gaa ttg gag att ttt aga agt aag        169
            Met Glu Glu Ser Glu Leu Glu Ile Phe Arg Ser Lys
              1               5                  10 ttt gtt aga ggc tca tct gtc acg aag cag cat gcc tgg cga aac cag       217
Phe Val Arg Gly Ser Ser Val Thr Lys Gln His Ala Trp Arg Asn Gln
         15                  20                  25 cac agc gag aag cgt tgc tct tcc tcc atc agt tct ata tcc ctg gac       265
His Ser Glu Lys Arg Cys Ser Ser Ser Ile Ser Ser Ile Ser Leu Asp
 30                  35                  40 aga atg cca tcg gaa atc ttg gtg aag ata ctt tct tac ttg gat gcg       313
Arg Met Pro Ser Glu Ile Leu Val Lys Ile Leu Ser Tyr Leu Asp Ala
 45                  50                  55                  60 gtg acc ttg gtg tgc att gga tgt gtg agc aga cgc ttt tat cat ttg       361
Val Thr Leu Val Cys Ile Gly Cys Val Ser Arg Arg Phe Tyr His Leu
                 65                  70                  75 gct gat gac aat ctt att tgg gtc agg aag tac gca gct gca ttt aga       409
Ala Asp Asp Asn Leu Ile Trp Val Arg Lys Tyr Ala Ala Ala Phe Arg
             80                  85                  90 tca aaa aga tca cgt tgg aaa gct act tca gtg gag gaa aca gcc aca       457
Ser Lys Arg Ser Arg Trp Lys Ala Thr Ser Val Glu Glu Thr Ala Thr
         95                 100                 105 agt ctg agc ttg ctg tca gtt tgg gat aaa gaa gat gga tac tgg aag       505
Ser Leu Ser Leu Leu Ser Val Trp Asp Lys Glu Asp Gly Tyr Trp Lys
110                 115                 120 aaa gaa tat att aca aag cag atc tca tct gtg aga gca gcc ctc acc       553
Lys Glu Tyr Ile Thr Lys Gln Ile Ser Ser Val Arg Ala Ala Leu Thr
125                 130                 135                 140 aac agc ctc agt cct gtc aaa cgc cgc aca agc ctt cct tcg aaa acc       601
Asn Ser Leu Ser Pro Val Lys Arg Arg Thr Ser Leu Pro Ser Lys Thr
                145                 150                 155 aaa gag tcc ctc aga ata tct ggc tta ggt tgg aca atc atc tta aga       649
Lys Glu Ser Leu Arg Ile Ser Gly Leu Gly Trp Thr Ile Ile Leu Arg
            160                 165                 170 gaa gcc agt ggc aaa gaa cac atc atg cag cat tcg aat ctt tcc gta       697
Glu Ala Ser Gly Lys Glu His Ile Met Gln His Ser Asn Leu Ser Val
        175                 180                 185 aat gac aac tct gtc act gtt ttt tgg cat gac aaa aat tgg cca cat       745
Asn Asp Asn Ser Val Thr Val Phe Trp His Asp Lys Asn Trp Pro His
    190                 195                 200 gta gac acg ttg tcc acc ctg gat ttg tat ggt gcc aca cca att ttt       793
Val Asp Thr Leu Ser Thr Leu Asp Leu Tyr Gly Ala Thr Pro Ile Phe
205                 210                 215                 220 atg gag cag tat aaa ggc cct aac aca agt tgt cca cga tgg ctg tct       841
Met Glu Gln Tyr Lys Gly Pro Asn Thr Ser Cys Pro Arg Trp Leu Ser
                225                 230                 235 tta att gaa aag tac gat ctg agt aat tta cgc aag tct gct atg att       889
Leu Ile Glu Lys Tyr Asp Leu Ser Asn Leu Arg Lys Ser Ala Met Ile
            240                 245                 250 ggc tgc gac aga cat gtt cgg gta ttc tgt gta aat cct ggc ctc ctg       937
Gly Cys Asp Arg His Val Arg Val Phe Cys Val Asn Pro Gly Leu Leu
        255                 260                 265 gtg ggg ctg tgg cag gag aat ggt gga cta gct ttt gtc atg gca aat       985
Val Gly Leu Trp Gln Glu Asn Gly Gly Leu Ala Phe Val Met Ala Asn
```

-continued

```
            270                 275                 280
att cat tcc cat ggc ctt ttc gag aga agc ata atg ggc tca gac act   1033
Ile His Ser His Gly Leu Phe Glu Arg Ser Ile Met Gly Ser Asp Thr
285                 290                 295                 300 att ccc tat aca ttg cct ccc gac act aca ttt gtg gat aac tac cca   1081
Ile Pro Tyr Thr Leu Pro Pro Asp Thr Thr Phe Val Asp Asn Tyr Pro
        305                 310                 315 gac tca atg acc ttt tat gga gat aaa ggc ttt cag ctg cat atc gac   1129
Asp Ser Met Thr Phe Tyr Gly Asp Lys Gly Phe Gln Leu His Ile Asp
320                 325                 330 att cat ggc agt aag act tac ttc ctg tgt agc acc ttc cac aat ctc   1177
Ile His Gly Ser Lys Thr Tyr Phe Leu Cys Ser Thr Phe His Asn Leu
        335                 340                 345 ttc tgc agg aga gcg ggc att aac aat gga tat gtg aag ttc ttg atg   1225
Phe Cys Arg Arg Ala Gly Ile Asn Asn Gly Tyr Val Lys Phe Leu Met
350                 355                 360 ata aac tta aaa aat aac aga gaa cac cta cct ctt gtt gga aaa gtt   1273
Ile Asn Leu Lys Asn Asn Arg Glu His Leu Pro Leu Val Gly Lys Val
365                 370                 375                 380 ggc ctt gaa tgg aga act gac tgt tta aat ggc cgt att gag agt tgc   1321
Gly Leu Glu Trp Arg Thr Asp Cys Leu Asn Gly Arg Ile Glu Ser Cys
                385                 390                 395 att gta gtg gat atg acc ttg ctg gat gag gac aag aag ccc atc tgg   1369
Ile Val Val Asp Met Thr Leu Leu Asp Glu Asp Lys Lys Pro Ile Trp
400                 405                 410 tat gtg agt tct cca gtg tgc ttg aga tct gcc tgc ctt cct gat ttc   1417
Tyr Val Ser Ser Pro Val Cys Leu Arg Ser Ala Cys Leu Pro Asp Phe
        415                 420                 425 ccg cag ccg gct tac tct ttc gag tac atg gac agc gta gga gga gtg   1465
Pro Gln Pro Ala Tyr Ser Phe Glu Tyr Met Asp Ser Val Gly Gly Val
430                 435                 440 tgc gca gac cta ggg tgg ttt gaa aat acc gat gaa tac ttc att gtc   1513
Cys Ala Asp Leu Gly Trp Phe Glu Asn Thr Asp Glu Tyr Phe Ile Val
445                 450                 455                 460 aga ctg gac att tac ctc agt gta gca aaa tta caa caa tgg ttt ggg   1561
Arg Leu Asp Ile Tyr Leu Ser Val Ala Lys Leu Gln Gln Trp Phe Gly
                465                 470                 475 agg caa taaatgctga gttagcagta gggagtcttg ttattagtaa gctgtttgtt   1617
Arg Gln
ttttacaact tgttttttat tgaaagttaa aataaagcat atttgtggta ttc        1670
```

<210> SEQ ID NO 10
<211> LENGTH: 478
<212> TYPE: PRT
<213> ORGANISM: Mus musculus

<400> SEQUENCE: 10

```
Met Glu Glu Ser Glu Leu Glu Ile Phe Arg Ser Lys Phe Val Arg Gly
1               5                   10                  15

Ser Ser Val Thr Lys Gln His Ala Trp Arg Asn Gln His Ser Glu Lys
            20                  25                  30

Arg Cys Ser Ser Ile Ser Ser Ile Ser Leu Asp Arg Met Pro Ser
        35                  40                  45

Glu Ile Leu Val Lys Ile Leu Ser Tyr Leu Asp Ala Val Thr Leu Val
50                  55                  60

Cys Ile Gly Cys Val Ser Arg Arg Phe Tyr His Leu Ala Asp Asp Asn
65                  70                  75                  80

Leu Ile Trp Val Arg Lys Tyr Ala Ala Ala Phe Arg Ser Lys Arg Ser
                85                  90                  95
```

Arg Trp Lys Ala Thr Ser Val Glu Glu Thr Ala Ser Leu Ser Leu
            100                 105                 110

Leu Ser Val Trp Asp Lys Glu Asp Gly Tyr Trp Lys Glu Tyr Ile
        115                 120                 125

Thr Lys Gln Ile Ser Ser Val Arg Ala Ala Leu Thr Asn Ser Leu Ser
130                 135                 140

Pro Val Lys Arg Thr Ser Leu Pro Ser Lys Thr Lys Glu Ser Leu
145                 150                 155                 160

Arg Ile Ser Gly Leu Gly Trp Thr Ile Ile Leu Arg Glu Ala Ser Gly
                165                 170                 175

Lys Glu His Ile Met Gln His Ser Asn Leu Ser Val Asn Asp Asn Ser
            180                 185                 190

Val Thr Val Phe Trp His Asp Lys Asn Trp Pro His Val Asp Thr Leu
        195                 200                 205

Ser Thr Leu Asp Leu Tyr Gly Ala Thr Pro Ile Phe Met Glu Gln Tyr
    210                 215                 220

Lys Gly Pro Asn Thr Ser Cys Pro Arg Trp Leu Ser Leu Ile Glu Lys
225                 230                 235                 240

Tyr Asp Leu Ser Asn Leu Arg Lys Ser Ala Met Ile Gly Cys Asp Arg
                245                 250                 255

His Val Arg Val Phe Cys Val Asn Pro Gly Leu Leu Val Gly Leu Trp
            260                 265                 270

Gln Glu Asn Gly Gly Leu Ala Phe Val Met Ala Asn Ile His Ser His
        275                 280                 285

Gly Leu Phe Glu Arg Ser Ile Met Gly Ser Asp Thr Ile Pro Tyr Thr
    290                 295                 300

Leu Pro Pro Asp Thr Thr Phe Val Asp Asn Tyr Pro Asp Ser Met Thr
305                 310                 315                 320

Phe Tyr Gly Asp Lys Gly Phe Gln Leu His Ile Asp His Ile His Gly Ser
                325                 330                 335

Lys Thr Tyr Phe Leu Cys Ser Thr Phe His Asn Leu Phe Cys Arg Arg
            340                 345                 350

Ala Gly Ile Asn Asn Gly Tyr Val Lys Phe Leu Met Ile Asn Leu Lys
        355                 360                 365

Asn Asn Arg Glu His Leu Pro Leu Val Gly Lys Val Gly Leu Glu Trp
    370                 375                 380

Arg Thr Asp Cys Leu Asn Gly Arg Ile Glu Ser Cys Ile Val Val Asp
385                 390                 395                 400

Met Thr Leu Leu Asp Glu Asp Lys Lys Pro Ile Trp Tyr Val Ser Ser
                405                 410                 415

Pro Val Cys Leu Arg Ser Ala Cys Leu Pro Asp Phe Pro Gln Pro Ala
            420                 425                 430

Tyr Ser Phe Glu Tyr Met Asp Ser Val Gly Val Cys Ala Asp Leu
        435                 440                 445

Gly Trp Phe Glu Asn Thr Asp Glu Tyr Phe Ile Val Arg Leu Asp Ile
    450                 455                 460

Tyr Leu Ser Val Ala Lys Leu Gln Gln Trp Phe Gly Arg Gln
465                 470                 475

<210> SEQ ID NO 11
<211> LENGTH: 1665
<212> TYPE: DNA
<213> ORGANISM: Homo sapiens
<220> FEATURE:
<221> NAME/KEY: CDS
<222> LOCATION: (21)..(1550)

<400> SEQUENCE: 11

```
agggtgaact ccttgtctct atg gcg act gga cgc ggt cgg atc ttg cag cag        53
                      Met Ala Thr Gly Arg Gly Arg Ile Leu Gln Gln
                        1               5                      10 cac tgg ctc ggc ctc cag acg ctg cgc ggg ccc agc agg ggc ggt ggc         101
His Trp Leu Gly Leu Gln Thr Leu Arg Gly Pro Ser Arg Gly Gly Gly
                 15                  20                  25 gcg gcc cgg ggg cgc gcc agg gcc ttt ggg tgc aga aag ggg cca ggg         149
Ala Ala Arg Gly Arg Ala Arg Ala Phe Gly Cys Arg Lys Gly Pro Gly
             30                  35                  40 gtc aag ctt tct gca ggc tct gct gcc ctg agg tgc cat gcc gga ggt         197
Val Lys Leu Ser Ala Gly Ser Ala Ala Leu Arg Cys His Ala Gly Gly
 45                  50                  55 gga cag cac tgg gag agc tct ttc tcc tgc tgt tct ggg ttc ctg gat         245
Gly Gln His Trp Glu Ser Ser Phe Ser Cys Cys Ser Gly Phe Leu Asp
 60                  65                  70                  75 gga atg cct tca gaa atc ttg ctg aag ata ttt tcc tac ttg gat gct         293
Gly Met Pro Ser Glu Ile Leu Leu Lys Ile Phe Ser Tyr Leu Asp Ala
                 80                  85                  90 gtg agc ctt ctg tgt act gga tgt gtg agc agg cgc ttt tat cat cta         341
Val Ser Leu Leu Cys Thr Gly Cys Val Ser Arg Arg Phe Tyr His Leu
             95                 100                 105 gcc aat gac aat ttt att tgg atc gga atc tac tca act gct ttt tca         389
Ala Asn Asp Asn Phe Ile Trp Ile Gly Ile Tyr Ser Thr Ala Phe Ser
         110                 115                 120 cct gca aga tca aat tgg aaa ttt aat tca gta gag aag ata gct atg         437
Pro Ala Arg Ser Asn Trp Lys Phe Asn Ser Val Glu Lys Ile Ala Met
125                 130                 135 tct atg agc ttt ctg tca gtt cag gat aaa gaa gct ggt tat tgg aag         485
Ser Met Ser Phe Leu Ser Val Gln Asp Lys Glu Ala Gly Tyr Trp Lys
140                 145                 150                 155 aaa gaa tat atc aca aaa caa ata gca tct gta aaa gcc gca cta gct         533
Lys Glu Tyr Ile Thr Lys Gln Ile Ala Ser Val Lys Ala Ala Leu Ala
                160                 165                 170 gac att ctc aaa cct gtc aac cct tac aca ggc ctt cca gtt aag acc         581
Asp Ile Leu Lys Pro Val Asn Pro Tyr Thr Gly Leu Pro Val Lys Thr
            175                 180                 185 aaa gag gcc ctc aga ata ttt ggt tta ggt tgg gca att ata ctg aaa         629
Lys Glu Ala Leu Arg Ile Phe Gly Leu Gly Trp Ala Ile Ile Leu Lys
        190                 195                 200 gaa aaa ggt gga aaa gaa tat atc atg gag cat gtt gat ctt tcc ata         677
Glu Lys Gly Gly Lys Glu Tyr Ile Met Glu His Val Asp Leu Ser Ile
205                 210                 215 aat gac aca tca gtt act gtt ata tgg tat ggc aaa aaa tgg cca tgc         725
Asn Asp Thr Ser Val Thr Val Ile Trp Tyr Gly Lys Lys Trp Pro Cys
220                 225                 230                 235 cta gca tca ttg tca acc tta gat tta tgt ggc atg aca cca gtt ttt         773
Leu Ala Ser Leu Ser Thr Leu Asp Leu Cys Gly Met Thr Pro Val Phe
                240                 245                 250 acc gac tgg tat aaa act ccc acc aaa cat aga ctc gga tgg cat tct         821
Thr Asp Trp Tyr Lys Thr Pro Thr Lys His Arg Leu Arg Trp His Ser
            255                 260                 265 tta att gca aag tac aat ctg agt cat ttg acc ata tct acc atg att         869
Leu Ile Ala Lys Tyr Asn Leu Ser His Leu Thr Ile Ser Thr Met Ile
        270                 275                 280 ggc tgt gac aga ctc att cgg atc ttc tgc ctg cac cct ggc ctc ctg         917
Gly Cys Asp Arg Leu Ile Arg Ile Phe Cys Leu His Pro Gly Leu Leu
285                 290                 295 gtg gga gtg tgg aag aag gag gaa gaa ctg gct ttt gtt atg gca aat         965
```

```
Val Gly Val Trp Lys Lys Glu Glu Leu Ala Phe Val Met Ala Asn
300             305                 310                 315 ctt cat ttt cat cac ctt gtg gag agg agc aca tta ggc tcg gct act    1013
Leu His Phe His His Leu Val Glu Arg Ser Thr Leu Gly Ser Ala Thr
            320                 325                 330 atc ccc tat gaa ctg cct cca cat agc ccc ttt ttg gat gat agc ccc    1061
Ile Pro Tyr Glu Leu Pro Pro His Ser Pro Phe Leu Asp Asp Ser Pro
                335                 340                 345 gag tat gga ctg cac ggc tac caa ctc cat gtt gat ctg cac agc ggt    1109
Glu Tyr Gly Leu His Gly Tyr Gln Leu His Val Asp Leu His Ser Gly
            350                 355                 360 ggg gtt ttc tac cta tgt ggt aca ttt cgc aat ctc ttc acc aag aga    1157
Gly Val Phe Tyr Leu Cys Gly Thr Phe Arg Asn Leu Phe Thr Lys Arg
365                 370                 375 gga aat att gaa aat gga cat gtg aag ctc att gtt ata cat tta aaa    1205
Gly Asn Ile Glu Asn Gly His Val Lys Leu Ile Val Ile His Leu Lys
380                 385                 390                 395 aat aac aga gaa cac cta cct ctt att gga aaa gtt ggc ctc tcg tgg    1253
Asn Asn Arg Glu His Leu Pro Leu Ile Gly Lys Val Gly Leu Ser Trp
            400                 405                 410 aaa act gat att ttt gat ggc tgt ata aag agt tgt tcc atg atg gac    1301
Lys Thr Asp Ile Phe Asp Gly Cys Ile Lys Ser Cys Ser Met Met Asp
            415                 420                 425 gta act ctt ttg gat gaa cat ggg aaa ccc ttt tgg tgt ttc agt tcc    1349
Val Thr Leu Leu Asp Glu His Gly Lys Pro Phe Trp Cys Phe Ser Ser
            430                 435                 440 ccg gtg tgc ctg aga tcg cct gcc aca ccc tct gac agc tct agc ttc    1397
Pro Val Cys Leu Arg Ser Pro Ala Thr Pro Ser Asp Ser Ser Ser Phe
445                 450                 455 ttg gga cag aca tac aac gtg gac tac gtt gat gcg gaa gga aga gtg    1445
Leu Gly Gln Thr Tyr Asn Val Asp Tyr Val Asp Ala Glu Gly Arg Val
460                 465                 470                 475 cac gtg gag ctg gtg tgg atc aga gag acc gaa gaa tac ctt att gtc    1493
His Val Glu Leu Val Trp Ile Arg Glu Thr Glu Glu Tyr Leu Ile Val
            480                 485                 490 aac ctg gtc ctt tat ctt agt atc gca aaa atc aac cat tgg ttt ggg    1541
Asn Leu Val Leu Tyr Leu Ser Ile Ala Lys Ile Asn His Trp Phe Gly
                495                 500                 505 act gaa tat tagcagtagg tggcaaatta ttgttgttat ttagttgttt            1590
Thr Glu Tyr
        510 attttgact ggctttgttc ttggtgttga aattaaaat aaagcaaatc tgcaaaaaaa    1650
aaaaaaaaaa aaaaa                                                   1665

<210> SEQ ID NO 12
<211> LENGTH: 510
<212> TYPE: PRT
<213> ORGANISM: Homo sapiens

<400> SEQUENCE: 12

Met Ala Thr Gly Arg Gly Arg Ile Leu Gln Gln His Trp Leu Gly Leu
1               5                   10                  15

Gln Thr Leu Arg Gly Pro Ser Arg Gly Gly Ala Ala Arg Gly Arg
            20                  25                  30

Ala Arg Ala Phe Gly Cys Arg Lys Gly Pro Gly Val Lys Leu Ser Ala
            35                  40                  45

Gly Ser Ala Ala Leu Arg Cys His Ala Gly Gly Gln His Trp Glu
50                  55                  60

Ser Ser Phe Ser Cys Cys Ser Gly Phe Leu Asp Gly Met Pro Ser Glu
```

```
                65                  70                  75                  80
Ile Leu Leu Lys Ile Phe Ser Tyr Leu Asp Ala Val Ser Leu Leu Cys
                    85                  90                  95

Thr Gly Cys Val Ser Arg Arg Phe Tyr His Leu Ala Asn Asp Asn Phe
                100                 105                 110

Ile Trp Ile Gly Ile Tyr Ser Thr Ala Phe Ser Pro Ala Arg Ser Asn
                115                 120                 125

Trp Lys Phe Asn Ser Val Glu Lys Ile Ala Met Ser Met Ser Phe Leu
                130                 135                 140

Ser Val Gln Asp Lys Glu Ala Gly Tyr Trp Lys Lys Glu Tyr Ile Thr
145                 150                 155                 160

Lys Gln Ile Ala Ser Val Lys Ala Ala Leu Ala Asp Ile Leu Lys Pro
                165                 170                 175

Val Asn Pro Tyr Thr Gly Leu Pro Val Lys Thr Lys Glu Ala Leu Arg
                180                 185                 190

Ile Phe Gly Leu Gly Trp Ala Ile Ile Leu Lys Glu Lys Gly Gly Lys
                195                 200                 205

Glu Tyr Ile Met Glu His Val Asp Leu Ser Ile Asn Asp Thr Ser Val
                210                 215                 220

Thr Val Ile Trp Tyr Gly Lys Lys Trp Pro Cys Leu Ala Ser Leu Ser
225                 230                 235                 240

Thr Leu Asp Leu Cys Gly Met Thr Pro Val Phe Thr Asp Trp Tyr Lys
                245                 250                 255

Thr Pro Thr Lys His Arg Leu Arg Trp His Ser Leu Ile Ala Lys Tyr
                260                 265                 270

Asn Leu Ser His Leu Thr Ile Ser Thr Met Ile Gly Cys Asp Arg Leu
                275                 280                 285

Ile Arg Ile Phe Cys Leu His Pro Gly Leu Leu Val Gly Val Trp Lys
                290                 295                 300

Lys Glu Glu Leu Ala Phe Val Met Ala Asn Leu His Phe His His
305                 310                 315                 320

Leu Val Glu Arg Ser Thr Leu Gly Ser Ala Thr Ile Pro Tyr Glu Leu
                325                 330                 335

Pro Pro His Ser Pro Phe Leu Asp Asp Ser Pro Glu Tyr Gly Leu His
                340                 345                 350

Gly Tyr Gln Leu His Val Asp Leu His Ser Gly Gly Val Phe Tyr Leu
                355                 360                 365

Cys Gly Thr Phe Arg Asn Leu Phe Thr Lys Arg Gly Asn Ile Glu Asn
                370                 375                 380

Gly His Val Lys Leu Ile Val Ile His Leu Lys Asn Asn Arg Glu His
385                 390                 395                 400

Leu Pro Leu Ile Gly Lys Val Gly Leu Ser Trp Lys Thr Asp Ile Phe
                405                 410                 415

Asp Gly Cys Ile Lys Ser Cys Ser Met Met Asp Val Thr Leu Leu Asp
                420                 425                 430

Glu His Gly Lys Pro Phe Trp Cys Phe Ser Ser Pro Val Cys Leu Arg
                435                 440                 445

Ser Pro Ala Thr Pro Ser Asp Ser Ser Ser Phe Leu Gly Gln Thr Tyr
                450                 455                 460

Asn Val Asp Tyr Val Asp Ala Glu Gly Arg Val His Val Glu Leu Val
465                 470                 475                 480

Trp Ile Arg Glu Thr Glu Glu Tyr Leu Ile Val Asn Leu Val Leu Tyr
                485                 490                 495
```

```
                                                               -continued

Leu Ser Ile Ala Lys Ile Asn His Trp Phe Gly Thr Glu Tyr
            500                 505                 510

<210> SEQ ID NO 13
<211> LENGTH: 2184
<212> TYPE: DNA
<213> ORGANISM: Mus musculus
<220> FEATURE:
<221> NAME/KEY: CDS
<222> LOCATION: (190)..(1104)

<400> SEQUENCE: 13
agaaaggctg atttggttgg tgtcttgctc tttctgtggg aaggctgcgg ctcacttcct      60
tccgacttct tgataatttt gcattagaca tttaactctt ctttctatga tctttccttc    120
tagacactga gttttttggt tgttgcctaa aaccttttca gaaatccctt ccctcgccat    180 cacactgac atg agt gtg ggt ctt cct ggt ccc cac agt ttg cct agt tct    231
           Met Ser Val Gly Leu Pro Gly Pro His Ser Leu Pro Ser Ser
             1               5                  10 gag gaa gca tcg aat tct ggg aac gcc tca tca atg cct gca gtt ttt      279
Glu Glu Ala Ser Asn Ser Gly Asn Ala Ser Ser Met Pro Ala Val Phe
 15                  20                  25                  30 cat ccc gag aac tat tct tgc tta caa ggg tct gct act gag atg ctc      327
His Pro Glu Asn Tyr Ser Cys Leu Gln Gly Ser Ala Thr Glu Met Leu
                 35                  40                  45 tgc aca gag gct gcc tct cct cgc cct tcc tct gaa gac ctg cct ctt      375
Cys Thr Glu Ala Ala Ser Pro Arg Pro Ser Ser Glu Asp Leu Pro Leu
             50                  55                  60 caa ggc agc cct gat tct tct acc agt ccc aaa caa aag ctc tca agt      423
Gln Gly Ser Pro Asp Ser Ser Thr Ser Pro Lys Gln Lys Leu Ser Ser
         65                  70                  75 cct gag gct gac aag ggc cct gag gag gag gag aac aag gtc ctt gcc      471
Pro Glu Ala Asp Lys Gly Pro Glu Glu Glu Glu Asn Lys Val Leu Ala
 80                  85                  90 agg aag cag aag atg cgg act gtg ttc tct cag gcc cag ctg tgt gca      519
Arg Lys Gln Lys Met Arg Thr Val Phe Ser Gln Ala Gln Leu Cys Ala
 95                 100                 105                 110 ctc aag gac agg ttt cag aag cag aag tac ctc agc ctc cag cag atg      567
Leu Lys Asp Arg Phe Gln Lys Gln Lys Tyr Leu Ser Leu Gln Gln Met
                115                 120                 125 caa gaa ctc tcc tcc att ctg aac ctg agc tat aag cag gtt aag acc      615
Gln Glu Leu Ser Ser Ile Leu Asn Leu Ser Tyr Lys Gln Val Lys Thr
            130                 135                 140 tgg ttt caa aac caa agg gtg aag tgc aag cgg tgg cag aaa aac cag      663
Trp Phe Gln Asn Gln Arg Val Lys Cys Lys Arg Trp Gln Lys Asn Gln
        145                 150                 155 tgg ttg aag act agc aat ggt ctg att cag aag ggc tca gca cca gtg      711
Trp Leu Lys Thr Ser Asn Gly Leu Ile Gln Lys Gly Ser Ala Pro Val
    160                 165                 170 gag tat ccc agc atc cat tgc agc tat ccc cag ggc tat ctg gtg aac      759
Glu Tyr Pro Ser Ile His Cys Ser Tyr Pro Gln Gly Tyr Leu Val Asn
175                 180                 185                 190 gca tct gga agc ctt tcc atg tgg ggc agc cag act tgg acc aac cca      807
Ala Ser Gly Ser Leu Ser Met Trp Gly Ser Gln Thr Trp Thr Asn Pro
                195                 200                 205 act tgg agc agc cag acc tgg acc aac cca act tgg aac aac cag acc      855
Thr Trp Ser Ser Gln Thr Trp Thr Asn Pro Thr Trp Asn Asn Gln Thr
            210                 215                 220 tgg acc aac cca act tgg agc agc cag gcc tgg acc gct cag tcc tgg      903
Trp Thr Asn Pro Thr Trp Ser Ser Gln Ala Trp Thr Ala Gln Ser Trp
        225                 230                 235
```

```
aac ggc cag cct tgg aat gct gct ccg ctc cat aac ttc ggg gag gac    951
Asn Gly Gln Pro Trp Asn Ala Ala Pro Leu His Asn Phe Gly Glu Asp
    240                 245                 250 ttt ctg cag cct tac gta cag ttg cag caa aac ttc tct gcc agt gat    999
Phe Leu Gln Pro Tyr Val Gln Leu Gln Gln Asn Phe Ser Ala Ser Asp
255                 260                 265                 270 ttg gag gtg aat ttg gaa gcc act agg gaa agc cat gcg cat ttt agc    1047
Leu Glu Val Asn Leu Glu Ala Thr Arg Glu Ser His Ala His Phe Ser
                275                 280                 285 acc cca caa gcc ttg gaa tta ttc ctg aac tac tct gtg act cca cca    1095
Thr Pro Gln Ala Leu Glu Leu Phe Leu Asn Tyr Ser Val Thr Pro Pro
            290                 295                 300 ggt gaa ata tgagacttac gcaacatctg ggcttaaagt cagggcaaag            1144
Gly Glu Ile
        305 ccaggttcct tccttcttcc aaatatttc atattttttt taaagattta tttattcatt    1204
atatgtaagt acactgtagc tgtcttcaga cactccagaa gagggcgtca gatcttgtta   1264
cgtatggttg tgagccacca tgtggttgct gggatttgaa ctcctgacct tcggaagagc   1324
agtcgggtgc tcttatccac tgagccatct caccagcccc tggtttattt ttttaattat   1384
tatttgcttt ttgtttatca agacagggtt tctctgcata gctctaattg tctttgaact   1444
agctctgcag accagcctgg ccttgaactc agagatctgc ccactatct ttgcctcctg    1504
aatgctggga ccaaggtgg cataccacca cacctggcat atatattgtt tatttctatt    1564
tctattttta ttggtgccag agcaaaccta ggcttagaa catgctgggc accaactcaa    1624
cttctgagct ctatttacaa cttggtgtgt tagtgtattt gtcttagttc tgaatttgtc   1684
ctttttttag tgttaactct aggctttgga gacagtgagg tgcatatact ctctccttcc   1744
caagaataag tgcttgaaca cccttaccca cgcccaccca cccatgctag tctttttct    1804
tagaagcgtg gtctggta tacactgtgt cattttgagg ggtgaggttt aaaagtatat    1864
acaaagtata acgatatggt ggctactctc gaggatgaga cagaaggacc aggagtttga   1924
gggtagctca gatatgcaat aagttcaagg ccaacctgta ctatgtttaa atagtaagac   1984
agcatctcga taaaataata aaactaaagt ctcaacaaaa taaaagcttt cacctattaa   2044
ggtgcttgct tgtccttgga gtccccaag agtaactgct atgttaatat ctgtagaaag    2104
atgtttatat ttgactgtac catgatgaac cgatgccagc tggactagtt taaacaaaat   2164
aaaacactaa ttttacctt                                                2184

<210> SEQ ID NO 14
<211> LENGTH: 305
<212> TYPE: PRT
<213> ORGANISM: Mus musculus

<400> SEQUENCE: 14

Met Ser Val Gly Leu Pro Gly Pro His Ser Leu Pro Ser Ser Glu Glu
 1               5                  10                  15

Ala Ser Asn Ser Gly Asn Ala Ser Ser Met Pro Ala Val Phe His Pro
            20                  25                  30

Glu Asn Tyr Ser Cys Leu Gln Gly Ser Ala Thr Glu Met Leu Cys Thr
        35                  40                  45

Glu Ala Ala Ser Pro Arg Pro Ser Ser Glu Asp Leu Pro Leu Gln Gly
    50                  55                  60

Ser Pro Asp Ser Ser Thr Ser Pro Lys Gln Lys Leu Ser Ser Pro Glu
65                  70                  75                  80

Ala Asp Lys Gly Pro Glu Glu Glu Glu Asn Lys Val Leu Ala Arg Lys
```

```
                85                  90                  95
Gln Lys Met Arg Thr Val Phe Ser Gln Ala Gln Leu Cys Ala Leu Lys
                100                 105                 110

Asp Arg Phe Gln Lys Gln Lys Tyr Leu Ser Leu Gln Gln Met Gln Glu
            115                 120                 125

Leu Ser Ser Ile Leu Asn Leu Ser Tyr Lys Gln Val Lys Thr Trp Phe
130                 135                 140

Gln Asn Gln Arg Val Lys Cys Lys Arg Trp Gln Lys Asn Gln Trp Leu
145                 150                 155                 160

Lys Thr Ser Asn Gly Leu Ile Gln Lys Gly Ser Ala Pro Val Glu Tyr
                165                 170                 175

Pro Ser Ile His Cys Ser Tyr Pro Gln Gly Tyr Leu Val Asn Ala Ser
            180                 185                 190

Gly Ser Leu Ser Met Trp Gly Ser Gln Thr Trp Thr Asn Pro Thr Trp
            195                 200                 205

Ser Ser Gln Thr Trp Thr Asn Pro Thr Trp Asn Gln Thr Trp Thr
210                 215                 220

Asn Pro Thr Trp Ser Ser Gln Ala Trp Thr Ala Gln Ser Trp Asn Gly
225                 230                 235                 240

Gln Pro Trp Asn Ala Ala Pro Leu His Asn Phe Gly Glu Asp Phe Leu
                245                 250                 255

Gln Pro Tyr Val Gln Leu Gln Asn Phe Ser Ala Ser Asp Leu Glu
            260                 265                 270

Val Asn Leu Glu Ala Thr Arg Glu Ser His Ala His Phe Ser Thr Pro
            275                 280                 285

Gln Ala Leu Glu Leu Phe Leu Asn Tyr Ser Val Thr Pro Pro Gly Glu
        290                 295                 300

Ile
305

<210> SEQ ID NO 15
<211> LENGTH: 2114
<212> TYPE: DNA
<213> ORGANISM: Homo sapiens
<220> FEATURE:
<221> NAME/KEY: CDS
<222> LOCATION: (217)..(1131)

<400> SEQUENCE: 15
attataaatc tagagactcc aggattttaa cgttctgctg gactgagctg gttgcctcat        60
gttattatgc aggcaactca ctttatccca atttcttgat acttttcctt ctggaggtcc       120
tatttctcta acatcttcca gaaaagtctt aaagctgcct taaccttttt tccagtccac       180
ctcttaaatt ttttcctcct cttcctctat actaac atg agt gtg gat cca gct        234
                                        Met Ser Val Asp Pro Ala
                                        1               5 tgt ccc caa agc ttg cct tgc ttt gaa gca tcc gac tgt aaa gaa tct        282
Cys Pro Gln Ser Leu Pro Cys Phe Glu Ala Ser Asp Cys Lys Glu Ser
            10                  15                  20 tca cct atg cct gtg att tgt ggg cct gaa gaa aac tat cca tcc ttg        330
Ser Pro Met Pro Val Ile Cys Gly Pro Glu Glu Asn Tyr Pro Ser Leu
        25                  30                  35 caa atg tct tct gct gag atg cct cac acg gag act gtc tct cct ctt        378
Gln Met Ser Ser Ala Glu Met Pro His Thr Glu Thr Val Ser Pro Leu
    40                  45                  50 ccc tcc tcc atg gat ctg ctt att cag gac agc cct gat tct tcc acc        426
Pro Ser Ser Met Asp Leu Leu Ile Gln Asp Ser Pro Asp Ser Ser Thr
55                  60                  65                  70
```

```
agt ccc aaa ggc aaa caa ccc act tct gca gag aat agt gtc gca aaa      474
Ser Pro Lys Gly Lys Gln Pro Thr Ser Ala Glu Asn Ser Val Ala Lys
             75                  80                  85 aag gaa gac aag gtc cca gtc aag aaa cag aag acc aga act gtg ttc      522
Lys Glu Asp Lys Val Pro Val Lys Lys Gln Lys Thr Arg Thr Val Phe
         90                  95                 100 tct tcc acc cag ctg tgt gta ctc aat gat aga ttt cag aga cag aaa      570
Ser Ser Thr Gln Leu Cys Val Leu Asn Asp Arg Phe Gln Arg Gln Lys
        105                 110                 115 tac ctc agc ctc cag cag atg caa gaa ctc tcc aac atc ctg aac ctc      618
Tyr Leu Ser Leu Gln Gln Met Gln Glu Leu Ser Asn Ile Leu Asn Leu
    120                 125                 130 agc tac aaa cag gtg aag acc tgg ttc cag aac cag aga atg aaa tct      666
Ser Tyr Lys Gln Val Lys Thr Trp Phe Gln Asn Gln Arg Met Lys Ser
135                 140                 145                 150 aag agg tgg cag aaa aac aac tgg ccg aag aat agc aat ggt gtg acg      714
Lys Arg Trp Gln Lys Asn Asn Trp Pro Lys Asn Ser Asn Gly Val Thr
                155                 160                 165 cag aag gcc tca gca cct acc tac ccc agc ctc tac tct tcc tac cac      762
Gln Lys Ala Ser Ala Pro Thr Tyr Pro Ser Leu Tyr Ser Ser Tyr His
            170                 175                 180 cag gga tgc ctg gtg aac ccg act ggg aac ctt cca atg tgg agc aac      810
Gln Gly Cys Leu Val Asn Pro Thr Gly Asn Leu Pro Met Trp Ser Asn
        185                 190                 195 cag acc tgg aac aat tca acc tgg agc aac cag acc cag aac atc cag      858
Gln Thr Trp Asn Asn Ser Thr Trp Ser Asn Gln Thr Gln Asn Ile Gln
    200                 205                 210 tcc tgg agc aac cac tcc tgg aac act cag acc tgg tgc acc caa tcc      906
Ser Trp Ser Asn His Ser Trp Asn Thr Gln Thr Trp Cys Thr Gln Ser
215                 220                 225                 230 tgg aac aat cag gcc tgg aac agt ccc ttc tat aac tgt gga gag gaa      954
Trp Asn Asn Gln Ala Trp Asn Ser Pro Phe Tyr Asn Cys Gly Glu Glu
                235                 240                 245 tct ctg cag tcc tgc atg cag ttc cag cca aat tct cct gcc agt gac     1002
Ser Leu Gln Ser Cys Met Gln Phe Gln Pro Asn Ser Pro Ala Ser Asp
            250                 255                 260 ttg gag gct gct ttg gaa gct gct ggg gaa ggc ctt aat gta ata cag     1050
Leu Glu Ala Ala Leu Glu Ala Ala Gly Glu Gly Leu Asn Val Ile Gln
        265                 270                 275 cag acc act agg tat ttt agt act cca caa acc atg gat tta ttc cta     1098
Gln Thr Thr Arg Tyr Phe Ser Thr Pro Gln Thr Met Asp Leu Phe Leu
    280                 285                 290 aac tac tcc atg aac atg caa cct gaa gac gtg tgaagatgag tgaaactgat   1151
Asn Tyr Ser Met Asn Met Gln Pro Glu Asp Val
295                 300                 305 attactcaat ttcagtctgg acactggctg aatccttcct ctcccctcct cccatccctc   1211
ataggatttt tcttgtttgg aaaccacgtg ttctggtttc catgatgcct atccagtcaa   1271
tctcatggag ggtggagtat ggttggagcc taatcagcga ggtttctttt tttttttttc   1331
ctattggatc ttcctggaga aaatactttt tttttttttt ttgagacgga gtcttgctct   1391
gtcgcccagg ctggagtgca gtggcgcggt cttggctcac tgcaagctcc gcctcccggg   1451
ttcacgccat tctcctgcct cagcctcccg agcagctggg actacaggcg cccgccacct   1511
cgcccggcta atatttttgta tttttagtag agacaggggtt tcactgtgtt agccaggatg   1571
gtctcgatct cctgaccttg tgatccgccc gcctcggcct ccctaacagc tgggattaca   1631
ggcgtgagcc accgcgccct gcctagaaaa gacattttaa taaccttggc tgctaaggac   1691
aacattgata gaagccgtct ctggctatag ataagtagat ctaatactag tttggatatc   1751
```

```
tttagggttt agaatctaac ctcaagaata agaaatacaa gtacgaattg gtgatgaaga      1811
tgtattcgta ttgtttggga ttgggaggct tgcttatttt ttttaaaact attgaggtaa      1871
agggttaagc tgtaacatac ttaattgatt tcttaccgtt tttggctctg ttttgctata      1931
tccnctaatt tgttggttgt gctaatcttt gtagaaagag gtcttgtatt tgctgcatcg      1991
taatgacatg agtactactt tagttggttt aagttcaaat gaatgaaaca aatattttc       2051 ctttagttga ttttaccctg atttcaccga gtgtttcgat gagtaaatat acagcttaaa     2111
cat                                                                   2114
```

<210> SEQ ID NO 16
<211> LENGTH: 305
<212> TYPE: PRT
<213> ORGANISM: Homo sapiens

<400> SEQUENCE: 16

```
Met Ser Val Asp Pro Ala Cys Pro Gln Ser Leu Pro Cys Phe Glu Ala
 1               5                  10                  15

Ser Asp Cys Lys Glu Ser Ser Pro Met Pro Val Ile Cys Gly Pro Glu
            20                  25                  30

Glu Asn Tyr Pro Ser Leu Gln Met Ser Ser Ala Glu Met Pro His Thr
        35                  40                  45

Glu Thr Val Ser Pro Leu Pro Ser Ser Met Asp Leu Leu Ile Gln Asp
    50                  55                  60

Ser Pro Asp Ser Ser Thr Ser Pro Lys Gly Lys Gln Pro Thr Ser Ala
65                  70                  75                  80

Glu Asn Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Met Gln Glu Leu
        115                 120                 125

Ser Asn Ile Leu Asn Leu Ser Tyr Lys Gln Val Lys Thr Trp Phe Gln
    130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300
```

Val
305

<210> SEQ ID NO 17
<211> LENGTH: 1078
<212> TYPE: DNA
<213> ORGANISM: Mus musculus
<220> FEATURE:
<221> NAME/KEY: CDS
<222> LOCATION: (178)..(858)

<400> SEQUENCE: 17

```
cagggggtcgg gcaggtggga gggggaagct cacatctccg ccctctgctg cctctggggg      60
tagggagcat cctaaccccc aactgtccgg tcagatccgc ctactgcccc tcatcagact     120
gctactcctg ggagcacagc acctgctctt tacacctctt ccttgagctg ctgggga        177 atg gct ttg cct aca aag tct agc atc ttg gac ctg agc tcc ggc acc       225
Met Ala Leu Pro Thr Lys Ser Ser Ile Leu Asp Leu Ser Ser Gly Thr
 1               5                  10                  15 cca tgc acc aga tct cca gag gaa agt cac gag gct tgg gca cag tgc       273
Pro Cys Thr Arg Ser Pro Glu Glu Ser His Glu Ala Trp Ala Gln Cys
             20                  25                  30 aaa gat gct ggc agg cag cta ccc gag tac aag gca gtg gtg gtg ggt       321
Lys Asp Ala Gly Arg Gln Leu Pro Glu Tyr Lys Ala Val Val Val Gly
         35                  40                  45 gca agt ggt gtt ggt aaa agt gct ctc acc atc cag atg act cac caa       369
Ala Ser Gly Val Gly Lys Ser Ala Leu Thr Ile Gln Met Thr His Gln
     50                  55                  60 tgc ttc gtg aaa gac cat gac ccc act atc caa gat tcc tac tgg aag       417
Cys Phe Val Lys Asp His Asp Pro Thr Ile Gln Asp Ser Tyr Trp Lys
 65                  70                  75                  80 gaa gtg gcc agg gac aac gga ggc tac att cta aat gtt ctg gat aca       465
Glu Val Ala Arg Asp Asn Gly Gly Tyr Ile Leu Asn Val Leu Asp Thr
                 85                  90                  95 tct ggg cag gat att cac cgg gct ctg cgt gac cag tgc ttg gca tct       513
Ser Gly Gln Asp Ile His Arg Ala Leu Arg Asp Gln Cys Leu Ala Ser
            100                 105                 110 ggt gat ggt gtg ctg ggc gtc ttt gct ctt gac gac ccc tcg tct ctg       561
Gly Asp Gly Val Leu Gly Val Phe Ala Leu Asp Asp Pro Ser Ser Leu
        115                 120                 125 gac cag ttg cag cag ata tgg tcc acc tgg acc cct cac cac aag cag       609
Asp Gln Leu Gln Gln Ile Trp Ser Thr Trp Thr Pro His His Lys Gln
    130                 135                 140 cct ctg gta cta gtg ggc aac aag tgt gac ctg gtg acc act gct gga       657
Pro Leu Val Leu Val Gly Asn Lys Cys Asp Leu Val Thr Thr Ala Gly
145                 150                 155                 160 gat gct cat gct gcc gca gcc ctc ctt gct cac aag ttg ggg gcc ccc       705
Asp Ala His Ala Ala Ala Ala Leu Leu Ala His Lys Leu Gly Ala Pro
                165                 170                 175 ttg gtg aag acc tca gcc aag acg cgg caa ggt gtg gag gaa gcc ttt       753
Leu Val Lys Thr Ser Ala Lys Thr Arg Gln Gly Val Glu Glu Ala Phe
            180                 185                 190 gcc ctg ctt gtc cat gag att cag agg gcc cag gag gct gtg gcc gaa       801
Ala Leu Leu Val His Glu Ile Gln Arg Ala Gln Glu Ala Val Ala Glu
        195                 200                 205 tca agc aag aag acc cga cac cag aaa gcc gtg tgt agc tgt ggc tgc       849
Ser Ser Lys Lys Thr Arg His Gln Lys Ala Val Cys Ser Cys Gly Cys
    210                 215                 220 tct gta gcc tgaagatctt tgtctagcaa attgacccct gtctcatgtc                898
Ser Val Ala
225
```

```
aaggtgacaa ttctcttgta ataagatctc cctctccgac caagttacca cagacatctt      958
tttattgtca tttggtgaga agttacgtgg taacatggga catccctcat tgactgtgtt     1018
ttatgaaact ctatgcaaaa ttaaataaat gttttcagga ttcaaagctt cctttatacc    1078

<210> SEQ ID NO 18
<211> LENGTH: 227
<212> TYPE: PRT
<213> ORGANISM: Mus musculus

<400> SEQUENCE: 18

Met Ala Leu Pro Thr Lys Ser Ser Ile Leu Asp Leu Ser Ser Gly Thr
  1               5                  10                  15

Pro Cys Thr Arg Ser Pro Glu Glu Ser His Glu Ala Trp Ala Gln Cys
                 20                  25                  30

Lys Asp Ala Gly Arg Gln Leu Pro Glu Tyr Lys Ala Val Val Val Gly
             35                  40                  45

Ala Ser Gly Val Gly Lys Ser Ala Leu Thr Ile Gln Met Thr His Gln
         50                  55                  60

Cys Phe Val Lys Asp His Asp Pro Thr Ile Gln Asp Ser Tyr Trp Lys
 65                  70                  75                  80

Glu Val Ala Arg Asp Asn Gly Gly Tyr Ile Leu Asn Val Leu Asp Thr
                 85                  90                  95

Ser Gly Gln Asp Ile His Arg Ala Leu Arg Asp Gln Cys Leu Ala Ser
            100                 105                 110

Gly Asp Gly Val Leu Gly Val Phe Ala Leu Asp Pro Ser Ser Leu
            115                 120                 125

Asp Gln Leu Gln Gln Ile Trp Ser Thr Trp Thr Pro His His Lys Gln
130                 135                 140

Pro Leu Val Leu Val Gly Asn Lys Cys Asp Leu Val Thr Thr Ala Gly
145                 150                 155                 160

Asp Ala His Ala Ala Ala Leu Leu Ala His Lys Leu Gly Ala Pro
                165                 170                 175

Leu Val Lys Thr Ser Ala Lys Thr Arg Gln Gly Val Glu Glu Ala Phe
            180                 185                 190

Ala Leu Leu Val His Glu Ile Gln Arg Ala Gln Glu Ala Val Ala Glu
        195                 200                 205

Ser Ser Lys Lys Thr Arg His Gln Lys Ala Val Cys Ser Cys Gly Cys
    210                 215                 220

Ser Val Ala
225

<210> SEQ ID NO 19
<211> LENGTH: 1266
<212> TYPE: DNA
<213> ORGANISM: Homo sapiens
<220> FEATURE:
<221> NAME/KEY: CDS
<222> LOCATION: (252)..(950)

<400> SEQUENCE: 19
cgtgaggagg gaaggagaga tgggggacg tgggacaggg agaaacaac ataaatcata       60 tatatatagc atgcaaattg gaaggtgatc agcacacaat aggcattcaa taaatgttga    120
aataatgaca ccccactgtc tccttgccct caaatggtct ccctaacgt atccctgtt      180 gtcttgcttc ttctcttccc acttgcagag cctgctgccc acgtctcttc cctgagctgc    240
ctgctggggt c atg gag ctg cca aca aag cct ggc acc ttc gac ctg ggc    290
            Met Glu Leu Pro Thr Lys Pro Gly Thr Phe Asp Leu Gly
```

```
ctg gcc aca tgg agc cct tcc ttc cag ggg gaa acc cac cgg gct cag    338
Leu Ala Thr Trp Ser Pro Ser Phe Gln Gly Glu Thr His Arg Ala Gln
 15                  20                  25 gca cgc cgc agg gat gtt ggc agg cag ctg cct gag tac aag gct gtg    386
Ala Arg Arg Arg Asp Val Gly Arg Gln Leu Pro Glu Tyr Lys Ala Val
 30                  35                  40                  45 gtg gtg ggc gcc agt ggc gtg ggc aag agt gcg ctg acc atc cag ctg    434
Val Val Gly Ala Ser Gly Val Gly Lys Ser Ala Leu Thr Ile Gln Leu
                 50                  55                  60 aac cac cag tgc ttc gtg gag gac cac gac ccc acc atc cag gat tcc    482
Asn His Gln Cys Phe Val Glu Asp His Asp Pro Thr Ile Gln Asp Ser
             65                  70                  75 tac tgg aag gag ttg acc ctg gac agt ggg gac tgc att ctg aat gtg    530
Tyr Trp Lys Glu Leu Thr Leu Asp Ser Gly Asp Cys Ile Leu Asn Val
         80                  85                  90 ctg gac aca gca ggg cag gcc atc cat agg gcc ctg cgt gac cag tgc    578
Leu Asp Thr Ala Gly Gln Ala Ile His Arg Ala Leu Arg Asp Gln Cys
     95                 100                 105 ctg gct gtc tgt gat ggt gtg ctg ggc gtc ttc gct ctc gat gac ccc    626
Leu Ala Val Cys Asp Gly Val Leu Gly Val Phe Ala Leu Asp Asp Pro
110                 115                 120                 125 tcg tct ctg atc cag ctg cag cag ata tgg gcc acc tgg ggc cct cac    674
Ser Ser Leu Ile Gln Leu Gln Gln Ile Trp Ala Thr Trp Gly Pro His
                130                 135                 140 ccc gcc cag ccc ctt gtc ctc gtg ggc aac aag tgt gac ctt gtg acc    722
Pro Ala Gln Pro Leu Val Leu Val Gly Asn Lys Cys Asp Leu Val Thr
            145                 150                 155 act gct gga gat gct cat gcc gct gct gca gcc ctc gca cac agc tgg    770
Thr Ala Gly Asp Ala His Ala Ala Ala Ala Leu Ala His Ser Trp
        160                 165                 170 ggg gcc cac ttc gtg gag acc tcg gcc aaa aca cgg caa ggc gtg gag    818
Gly Ala His Phe Val Glu Thr Ser Ala Lys Thr Arg Gln Gly Val Glu
    175                 180                 185 gag gcc ttt tcc ctg ctg gtc cat gag atc cag agg gtc cag gag gcc    866
Glu Ala Phe Ser Leu Leu Val His Glu Ile Gln Arg Val Gln Glu Ala
190                 195                 200                 205 atg gcg aag gag ccc atg gca agg tcc tgt agg gag aag acc cgg cac    914
Met Ala Lys Glu Pro Met Ala Arg Ser Cys Arg Glu Lys Thr Arg His
                210                 215                 220 cag aag gcc acc tgc cac tgt ggc tgc tct gtg gcc tgaaggtctt         960
Gln Lys Ala Thr Cys His Cys Gly Cys Ser Val Ala
            225                 230 ggccaagaaa tgtagacctt tccccaggcc agggtgattg ttcatttgac atgagacccc  1020
tgaggcaact agctttgagg gacacatcag gtatactagg gaaagatgga catctctctt  1080
gttttcactt ggtgaggggc tttttggtaa catgggagtg cctaatgttg cttttgttat  1140
gtcaagttga aagattttgt gcaaaattaa ataaatggtg ttttgggttt caaagctgcc  1200
tccatgccga gtgttgtgtg ggtgggagtg agactgggta gaatgttact tgagttgtga  1260
gaattc                                                            1266

<210> SEQ ID NO 20
<211> LENGTH: 233
<212> TYPE: PRT
<213> ORGANISM: Homo sapiens

<400> SEQUENCE: 20

Met Glu Leu Pro Thr Lys Pro Gly Thr Phe Asp Leu Gly Leu Ala Thr
 1               5                  10                  15
```

```
Trp Ser Pro Ser Phe Gln Gly Glu Thr His Arg Ala Gln Ala Arg Arg
             20                  25                  30

Arg Asp Val Gly Arg Gln Leu Pro Glu Tyr Lys Ala Val Val Val Gly
         35                  40                  45

Ala Ser Gly Val Gly Lys Ser Ala Leu Thr Ile Gln Leu Asn His Gln
 50                  55                  60

Cys Phe Val Glu Asp His Asp Pro Thr Ile Gln Asp Ser Tyr Trp Lys
 65                  70                  75                  80

Glu Leu Thr Leu Asp Ser Gly Asp Cys Ile Leu Asn Val Leu Asp Thr
                 85                  90                  95

Ala Gly Gln Ala Ile His Arg Ala Leu Arg Asp Gln Cys Leu Ala Val
            100                 105                 110

Cys Asp Gly Val Leu Gly Val Phe Ala Leu Asp Asp Pro Ser Ser Leu
        115                 120                 125

Ile Gln Leu Gln Gln Ile Trp Ala Thr Trp Gly Pro His Pro Ala Gln
130                 135                 140

Pro Leu Val Leu Val Gly Asn Lys Cys Asp Leu Val Thr Thr Ala Gly
145                 150                 155                 160

Asp Ala His Ala Ala Ala Ala Leu Ala His Ser Trp Gly Ala His
            165                 170                 175

Phe Val Glu Thr Ser Ala Lys Thr Arg Gln Gly Val Glu Glu Ala Phe
            180                 185                 190

Ser Leu Leu Val His Glu Ile Gln Arg Val Gln Glu Ala Met Ala Lys
        195                 200                 205

Glu Pro Met Ala Arg Ser Cys Arg Glu Lys Thr Arg His Gln Lys Ala
210                 215                 220

Thr Cys His Cys Gly Cys Ser Val Ala
225                 230

<210> SEQ ID NO 21
<211> LENGTH: 1063
<212> TYPE: DNA
<213> ORGANISM: Mus musculus
<220> FEATURE:
<221> NAME/KEY: CDS
<222> LOCATION: (177)..(872)

<400> SEQUENCE: 21
gatacaaatt cgaatgtagg tgctaggcgc gcttgtgtta gagtgtttgt taggggagac      60
tgatggaatc cacagtccaa tgagtacagg gcctgtcctc cgtgtggcag cttcacccgg     120
gagttgctgg cctggctgcc tacctgcttt cctgagatcc aggacttttt cccaga atg     179
                                                              Met
                                                                1 gct ttg ggt gac ctc ctg ctg tct gtc ctc tct gcc cag gaa atg aat     227
Ala Leu Gly Asp Leu Leu Leu Ser Val Leu Ser Ala Gln Glu Met Asn
        5                   10                  15 gcc ctt cgt ggc cag gtg ggc ggg gac gtc aat gtg gag atg gac gcc     275
Ala Leu Arg Gly Gln Val Gly Gly Asp Val Asn Val Glu Met Asp Ala
     20                  25                  30 gcc ccc ggt gtg gac ctg agc cgc atc ctg aac gag atg cgg gat cag     323
Ala Pro Gly Val Asp Leu Ser Arg Ile Leu Asn Glu Met Arg Asp Gln
 35                  40                  45 tat gag aag atg gcg gag aag aac cgc aag gat gct gag gaa tgg ttc     371
Tyr Glu Lys Met Ala Glu Lys Asn Arg Lys Asp Ala Glu Glu Trp Phe
 50                  55                  60                  65 ttc acc aag aca gag gag ctg aac cga gaa gtg gcc acc aac acg gag     419
Phe Thr Lys Thr Glu Glu Leu Asn Arg Glu Val Ala Thr Asn Thr Glu
```

| | | | | | | | | | | | | | | | | |
|---|---|---|---|---|---|---|---|---|---|---|---|---|---|---|---|---|
| | | | | 70 | | | | | 75 | | | | | 80 | | |
| gcc | ctg | cag | agc | agc | cgg | aca | gag | atc | acg | gag | ctc | cgc | cgc | tct | gtg | 467 |
| Ala | Leu | Gln | Ser | Ser | Arg | Thr | Glu | Ile | Thr | Glu | Leu | Arg | Arg | Ser | Val | |
| | | | | 85 | | | | | 90 | | | | | 95 | | |
| cag | aac | ctg | gag | att | gag | ctg | cag | tcc | cag | ctc | agc | atg | aaa | gca | tca | 515 |
| Gln | Asn | Leu | Glu | Ile | Glu | Leu | Gln | Ser | Gln | Leu | Ser | Met | Lys | Ala | Ser | |
| | | | | 100 | | | | | 105 | | | | | 110 | | |
| ctg | gag | aac | agc | ctg | gca | gag | aca | gag | gcg | cgc | tat | ggg | gcc | cag | ctg | 563 |
| Leu | Glu | Asn | Ser | Leu | Ala | Glu | Thr | Glu | Ala | Arg | Tyr | Gly | Ala | Gln | Leu | |
| | 115 | | | | | 120 | | | | | 125 | | | | | |
| gcg | cag | ctg | cag | ggc | ctc | att | agc | agt | gtg | gaa | cag | cag | ctg | tgt | gag | 611 |
| Ala | Gln | Leu | Gln | Gly | Leu | Ile | Ser | Ser | Val | Glu | Gln | Gln | Leu | Cys | Glu | |
| 130 | | | | | 135 | | | | | 140 | | | | | 145 | |
| ctg | cgt | tgt | gac | atg | gaa | agg | cag | aat | cat | gag | tac | cag | gtg | ctg | ctg | 659 |
| Leu | Arg | Cys | Asp | Met | Glu | Arg | Gln | Asn | His | Glu | Tyr | Gln | Val | Leu | Leu | |
| | | | | 150 | | | | | 155 | | | | | 160 | | |
| gat | gtg | aag | acc | cga | ctg | gag | cag | gag | atc | gcc | acc | tac | cgc | cgt | ctg | 707 |
| Asp | Val | Lys | Thr | Arg | Leu | Glu | Gln | Glu | Ile | Ala | Thr | Tyr | Arg | Arg | Leu | |
| | | | | 165 | | | | | 170 | | | | | 175 | | |
| ctg | gag | ggc | gag | gac | gcc | cac | ctg | gct | act | caa | tac | tcc | tca | tcc | ctg | 755 |
| Leu | Glu | Gly | Glu | Asp | Ala | His | Leu | Ala | Thr | Gln | Tyr | Ser | Ser | Ser | Leu | |
| | | | | 180 | | | | | 185 | | | | | 190 | | |
| gct | tcg | cag | ccc | tcc | cga | gaa | ggc | atg | gtg | acc | agc | cgc | cag | gtg | cgc | 803 |
| Ala | Ser | Gln | Pro | Ser | Arg | Glu | Gly | Met | Val | Thr | Ser | Arg | Gln | Val | Arg | |
| | 195 | | | | | 200 | | | | | 205 | | | | | |
| acc | att | gtg | gag | gaa | gtc | cag | gat | ggt | aag | gtg | ttt | tcc | tcc | aga | gag | 851 |
| Thr | Ile | Val | Glu | Glu | Val | Gln | Asp | Gly | Lys | Val | Phe | Ser | Ser | Arg | Glu | |
| 210 | | | | | 215 | | | | | 220 | | | | | 225 | |
| cag | gag | cac | cgc | tcc | acc | cac | tgaggcccct | | gtctgcgtat | | gatagcccag | | | | | 902 |
| Gln | Glu | His | Arg | Ser | Thr | His | | | | | | | | | | |
| | | | | 230 | | | | | | | | | | | | | gcccaggacc ttaggctgca gctccctgca tctactgcca agcctgaact cctatgagct 962 agctgttgcc ttctgtgttt gctttgtgct gcccccttaca gagaggcccc ttgggttgac 1022 cccagaaatt gctaataaag ctttgaagaa gtctgatcct t 1063

```
<210> SEQ ID NO 22
<211> LENGTH: 232
<212> TYPE: PRT
<213> ORGANISM: Mus musculus

<400> SEQUENCE: 22
```

| Met | Ala | Leu | Gly | Asp | Leu | Leu | Ser | Val | Leu | Ser | Ala | Gln | Glu | Met |
|---|---|---|---|---|---|---|---|---|---|---|---|---|---|---|
| 1 | | | | 5 | | | | | 10 | | | | | 15 |

| Asn | Ala | Leu | Arg | Gly | Gln | Val | Gly | Gly | Asp | Val | Asn | Val | Glu | Met | Asp |
|---|---|---|---|---|---|---|---|---|---|---|---|---|---|---|---|
| | | | 20 | | | | | 25 | | | | | 30 | | |

| Ala | Ala | Pro | Gly | Val | Asp | Leu | Ser | Arg | Ile | Leu | Asn | Glu | Met | Arg | Asp |
|---|---|---|---|---|---|---|---|---|---|---|---|---|---|---|---|
| | | 35 | | | | | 40 | | | | | 45 | | | |

| Gln | Tyr | Glu | Lys | Met | Ala | Glu | Lys | Asn | Arg | Lys | Asp | Ala | Glu | Glu | Trp |
|---|---|---|---|---|---|---|---|---|---|---|---|---|---|---|---|
| | 50 | | | | | 55 | | | | | 60 | | | | |

| Phe | Phe | Thr | Lys | Thr | Glu | Glu | Leu | Asn | Arg | Glu | Val | Ala | Thr | Asn | Thr |
|---|---|---|---|---|---|---|---|---|---|---|---|---|---|---|---|
| 65 | | | | | 70 | | | | | 75 | | | | | 80 |

| Glu | Ala | Leu | Gln | Ser | Ser | Arg | Thr | Glu | Ile | Thr | Glu | Leu | Arg | Arg | Ser |
|---|---|---|---|---|---|---|---|---|---|---|---|---|---|---|---|
| | | | | 85 | | | | | 90 | | | | | 95 | |

| Val | Gln | Asn | Leu | Glu | Ile | Glu | Leu | Gln | Ser | Gln | Leu | Ser | Met | Lys | Ala |
|---|---|---|---|---|---|---|---|---|---|---|---|---|---|---|---|
| | | | 100 | | | | | 105 | | | | | 110 | | |

| Ser | Leu | Glu | Asn | Ser | Leu | Ala | Glu | Thr | Glu | Ala | Arg | Tyr | Gly | Ala | Gln |
|---|---|---|---|---|---|---|---|---|---|---|---|---|---|---|---|
| | 115 | | | | | 120 | | | | | 125 | | | | |

```
Leu Ala Gln Leu Gln Gly Leu Ile Ser Ser Val Glu Gln Gln Leu Cys
            130                 135                 140

Glu Leu Arg Cys Asp Met Glu Arg Gln Asn His Glu Tyr Gln Val Leu
145                 150                 155                 160

Leu Asp Val Lys Thr Arg Leu Glu Gln Glu Ile Ala Thr Tyr Arg Arg
                165                 170                 175

Leu Leu Glu Gly Glu Asp Ala His Leu Ala Thr Gln Tyr Ser Ser Ser
            180                 185                 190

Leu Ala Ser Gln Pro Ser Arg Glu Gly Met Val Thr Ser Arg Gln Val
                195                 200                 205

Arg Thr Ile Val Glu Glu Val Gln Asp Gly Lys Val Phe Ser Ser Arg
            210                 215                 220

Glu Gln Glu His Arg Ser Thr His
225                 230

<210> SEQ ID NO 23
<211> LENGTH: 1670
<212> TYPE: DNA
<213> ORGANISM: Mus musculus
<220> FEATURE:
<221> NAME/KEY: CDS
<222> LOCATION: (139)..(1401)

<400> SEQUENCE: 23
gacaccctca accccatcat cccaggccct cataggctcc atccagcatt acgtcctcat    60
ccctacctac gggttctgac gaccctgctg tcacacccgc catcccttgg acgcagaccc   120
ttctagccga ttacatca atg ggt tcc cgg gag aca cct tct tct tgc tct     171
                    Met Gly Ser Arg Glu Thr Pro Ser Ser Cys Ser
                     1               5                      10 aag acc ctt gaa acc ttg gac ctg gag act tcc gac agc tct agc cct    219
Lys Thr Leu Glu Thr Leu Asp Leu Glu Thr Ser Asp Ser Ser Ser Pro
             15                  20                  25 gat gct gac agt cct ctg gaa gag caa tgg ctg aaa tcc tcc cca gcc    267
Asp Ala Asp Ser Pro Leu Glu Glu Gln Trp Leu Lys Ser Ser Pro Ala
         30                  35                  40 ctg aag gag gac agt gtg gat gtg gta ctg gaa gac tgc aaa gag cct    315
Leu Lys Glu Asp Ser Val Asp Val Val Leu Glu Asp Cys Lys Glu Pro
     45                  50                  55 ctg tcc ccc tcc tcg cct ccg aca ggc aga gag atg atc agg tac gaa    363
Leu Ser Pro Ser Ser Pro Pro Thr Gly Arg Glu Met Ile Arg Tyr Glu
 60                  65                  70                  75 gtc aaa gtg aac cga cgg agc att gaa gac atc tgc ctc tgc tgt gga    411
Val Lys Val Asn Arg Arg Ser Ile Glu Asp Ile Cys Leu Cys Cys Gly
                 80                  85                  90 act ctc cag gtg tac act cgg cac ccc ttg ttt gag gga ggg tta tgt    459
Thr Leu Gln Val Tyr Thr Arg His Pro Leu Phe Glu Gly Gly Leu Cys
             95                 100                 105 gcc cca tgt aag gat aag ttc ctg gag tcc ctc ttc ctg tat gat gat    507
Ala Pro Cys Lys Asp Lys Phe Leu Glu Ser Leu Phe Leu Tyr Asp Asp
         110                 115                 120 gat gga cac cag agt tac tgc acc atc tgc tgt tcc ggg ggt acc ctg    555
Asp Gly His Gln Ser Tyr Cys Thr Ile Cys Cys Ser Gly Gly Thr Leu
     125                 130                 135 ttc atc tgt gag agc ccc gac tgt acc aga tgc tac tgt ttc gag tgt    603
Phe Ile Cys Glu Ser Pro Asp Cys Thr Arg Cys Tyr Cys Phe Glu Cys
140                 145                 150                 155 gtg gac atc ctg gtg ggc ccc ggg acc tca gag agg atc aat gcc atg    651
Val Asp Ile Leu Val Gly Pro Gly Thr Ser Glu Arg Ile Asn Ala Met
                160                 165                 170
```

| | | |
|---|---|---|
| gcc tgc tgg gtt tgc ttc ctg tgc ctg ccc ttc tca cgg agt gga ctg<br>Ala Cys Trp Val Cys Phe Leu Cys Leu Pro Phe Ser Arg Ser Gly Leu<br>175 180 185 | | 699 |
| ctg cag agg cgc aag agg tgg cgg cac cag ctg aag gcc ttc cat gat<br>Leu Gln Arg Arg Lys Arg Trp Arg His Gln Leu Lys Ala Phe His Asp<br>190 195 200 | | 747 |
| caa gag gga gcg ggc cct atg gag ata tac aag aca gtg tct gca tgg<br>Gln Glu Gly Ala Gly Pro Met Glu Ile Tyr Lys Thr Val Ser Ala Trp<br>205 210 215 | | 795 |
| aag aga cag cca gtg cgg gta ctg agc ctt ttt aga aat att gat aaa<br>Lys Arg Gln Pro Val Arg Val Leu Ser Leu Phe Arg Asn Ile Asp Lys<br>220 225 230 235 | | 843 |
| gta cta aag agt ttg ggc ttt ttg gaa agc ggt tct ggt tct ggg gga<br>Val Leu Lys Ser Leu Gly Phe Leu Glu Ser Gly Ser Gly Ser Gly Gly<br>240 245 250 | | 891 |
| gga acg ctg aag tac gtg gaa gat gtc aca aat gtc gtg agg aga gac<br>Gly Thr Leu Lys Tyr Val Glu Asp Val Thr Asn Val Val Arg Arg Asp<br>255 260 265 | | 939 |
| gtg gag aaa tgg ggc ccc ttt gac ctg gtg tac ggc tcg acg cag ccc<br>Val Glu Lys Trp Gly Pro Phe Asp Leu Val Tyr Gly Ser Thr Gln Pro<br>270 275 280 | | 987 |
| cta ggc agc tct tgt gat cgc tgt ccc ggc tgg tac atg ttc cag ttc<br>Leu Gly Ser Ser Cys Asp Arg Cys Pro Gly Trp Tyr Met Phe Gln Phe<br>285 290 295 | | 1035 |
| cac cgg atc ctg cag tat gcg ctg cct cgc cag gag agt cag cgg ccc<br>His Arg Ile Leu Gln Tyr Ala Leu Pro Arg Gln Glu Ser Gln Arg Pro<br>300 305 310 315 | | 1083 |
| ttc ttc tgg ata ttc atg gac aat ctg ctg act gag gat gac caa<br>Phe Phe Trp Ile Phe Met Asp Asn Leu Leu Leu Thr Glu Asp Asp Gln<br>320 325 330 | | 1131 |
| gag aca act acc cgc ttc ctt cag aca gag gct gtg acc ctc cag gat<br>Glu Thr Thr Thr Arg Phe Leu Gln Thr Glu Ala Val Thr Leu Gln Asp<br>335 340 345 | | 1179 |
| gtc cgt ggc aga gac tac cag aat gct atg cgg gtg tgg agc aac att<br>Val Arg Gly Arg Asp Tyr Gln Asn Ala Met Arg Val Trp Ser Asn Ile<br>350 355 360 | | 1227 |
| cca ggg ctg aag agc aag cat gcg ccc ctg acc cca aag gaa gaa gag<br>Pro Gly Leu Lys Ser Lys His Ala Pro Leu Thr Pro Lys Glu Glu Glu<br>365 370 375 | | 1275 |
| tat ctg caa gcc caa gtc aga agc agg agc aag ctg gac gcc ccg aaa<br>Tyr Leu Gln Ala Gln Val Arg Ser Arg Ser Lys Leu Asp Ala Pro Lys<br>380 385 390 395 | | 1323 |
| gtt gac ctc ctg gtg aag aac tgc ctt ctc ccg ctg aga gag tac ttc<br>Val Asp Leu Leu Val Lys Asn Cys Leu Leu Pro Leu Arg Glu Tyr Phe<br>400 405 410 | | 1371 |
| aag tat ttt tct caa aac tca ctt cct ctt tagaaatgaa tcaccataag<br>Lys Tyr Phe Ser Gln Asn Ser Leu Pro Leu<br>415 420 | | 1421 |
| atgaaagtct ttcctagaac cagggcagat ttcttcctaa ggtctcttcc ctccacagtt | | 1481 |
| ttctctggtt tgctttcagg ccttcgggtt tctctcctgt ttgattgcca ggatgcctct | | 1541 |
| gtgcagctca ctttgcgggg tgggaggtgc ctacggctct gcacaagttc ccggtgggat | | 1601 |
| aacctgccat gtttctctga aactgtgtgt acctgttgtg aagttttca aatatatcat | | 1661 |
| aggattgtt | | 1670 |

<210> SEQ ID NO 24
<211> LENGTH: 421
<212> TYPE: PRT
<213> ORGANISM: Mus musculus

<400> SEQUENCE: 24

```
Met Gly Ser Arg Glu Thr Pro Ser Ser Cys Ser Lys Thr Leu Glu Thr
  1               5                  10                  15

Leu Asp Leu Glu Thr Ser Asp Ser Ser Pro Asp Ala Asp Ser Pro
                 20                  25                  30

Leu Glu Glu Gln Trp Leu Lys Ser Ser Pro Ala Leu Lys Glu Asp Ser
                 35                  40                  45

Val Asp Val Val Leu Glu Asp Cys Lys Glu Pro Leu Ser Pro Ser Ser
 50                  55                  60

Pro Pro Thr Gly Arg Glu Met Ile Arg Tyr Glu Val Lys Val Asn Arg
 65                  70                  75                  80

Arg Ser Ile Glu Asp Ile Cys Leu Cys Cys Gly Thr Leu Gln Val Tyr
                 85                  90                  95

Thr Arg His Pro Leu Phe Glu Gly Gly Leu Cys Ala Pro Cys Lys Asp
                100                 105                 110

Lys Phe Leu Glu Ser Leu Phe Leu Tyr Asp Asp Gly His Gln Ser
                115                 120                 125

Tyr Cys Thr Ile Cys Cys Ser Gly Gly Thr Leu Phe Ile Cys Glu Ser
130                 135                 140

Pro Asp Cys Thr Arg Cys Tyr Cys Phe Glu Cys Val Asp Ile Leu Val
145                 150                 155                 160

Gly Pro Gly Thr Ser Glu Arg Ile Asn Ala Met Ala Cys Trp Val Cys
                165                 170                 175

Phe Leu Cys Leu Pro Phe Ser Arg Ser Gly Leu Leu Gln Arg Arg Lys
                180                 185                 190

Arg Trp Arg His Gln Leu Lys Ala Phe His Asp Gln Glu Gly Ala Gly
                195                 200                 205

Pro Met Glu Ile Tyr Lys Thr Val Ser Ala Trp Lys Arg Gln Pro Val
210                 215                 220

Arg Val Leu Ser Leu Phe Arg Asn Ile Asp Lys Val Leu Lys Ser Leu
225                 230                 235                 240

Gly Phe Leu Glu Ser Gly Ser Gly Ser Gly Gly Thr Leu Lys Tyr
                245                 250                 255

Val Glu Asp Val Thr Asn Val Val Arg Arg Asp Val Glu Lys Trp Gly
                260                 265                 270

Pro Phe Asp Leu Val Tyr Gly Ser Thr Gln Pro Leu Gly Ser Ser Cys
                275                 280                 285

Asp Arg Cys Pro Gly Trp Tyr Met Phe Gln Phe His Arg Ile Leu Gln
                290                 295                 300

Tyr Ala Leu Pro Arg Gln Glu Ser Gln Arg Pro Phe Phe Trp Ile Phe
305                 310                 315                 320

Met Asp Asn Leu Leu Leu Thr Glu Asp Asp Gln Glu Thr Thr Thr Arg
                325                 330                 335

Phe Leu Gln Thr Glu Ala Val Thr Leu Gln Asp Val Arg Gly Arg Asp
                340                 345                 350

Tyr Gln Asn Ala Met Arg Val Trp Ser Asn Ile Pro Gly Leu Lys Ser
                355                 360                 365

Lys His Ala Pro Leu Thr Pro Lys Glu Glu Tyr Leu Gln Ala Gln
                370                 375                 380

Val Arg Ser Arg Ser Lys Leu Asp Ala Pro Lys Val Asp Leu Leu Val
385                 390                 395                 400

Lys Asn Cys Leu Leu Pro Leu Arg Glu Tyr Phe Lys Tyr Phe Ser Gln
                405                 410                 415
```

Asn Ser Leu Pro Leu
    420

<210> SEQ ID NO 25
<211> LENGTH: 1705
<212> TYPE: DNA
<213> ORGANISM: Homo sapiens
<220> FEATURE:
<221> NAME/KEY: CDS
<222> LOCATION: (485)..(1645)

<400> SEQUENCE: 25

```
cccatctcca cccctcccct gaacccccact ccccactgag gtccccaaac cccaccctc      60 actccaccct gagggcccca tcctctgaac cccaatcccc cagccccact gagctcttaa     120
ccctccccac ctgagggttc cctttccctg cccgtccccc agcttcctag ctccccaccc     180
caagtgaccc cccgcagctc ctcgcccctc ccactgcaaa ccggcactga agggctgccc     240 cgccccccgcc cctccccgcc ccgcgggac acgcccagat tctttgcccc catagcctgg     300
tgacctctgg ccaccgctg tcccaggtgg gcctggatcc ttccagctca ttctttgcct     360
gcgccgtccc tcgttccatg gcccagtcct cccgggac cctgagcctg aagcccgg       420 accactggaa ccttgaaccc accagctggc tgtacccgga gccgtggcag cagccctcat     480 cccc atg gcg gcc atc cca gcc ctg gac cca gag gcc gag ccc agc atg     529
     Met Ala Ala Ile Pro Ala Leu Asp Pro Glu Ala Glu Pro Ser Met
      1               5                  10                  15 gac gtg att ttg gtg gga tcc agt gag ctc tca agc tcc gtt tca ccc     577
Asp Val Ile Leu Val Gly Ser Ser Glu Leu Ser Ser Ser Val Ser Pro
             20                  25                  30 ggg aca ggc aga gat ctt att gca tat gaa gtc aag gct aac cag cga     625
Gly Thr Gly Arg Asp Leu Ile Ala Tyr Glu Val Lys Ala Asn Gln Arg
         35                  40                  45 aat ata gaa gac atc tgc atc tgc tgc gga agt ctc cag gtt cac aca     673
Asn Ile Glu Asp Ile Cys Ile Cys Cys Gly Ser Leu Gln Val His Thr
     50                  55                  60 cag cac cct ctg ttt gag gga ggg atc tgc gcc cca tgt aag gac aag     721
Gln His Pro Leu Phe Glu Gly Gly Ile Cys Ala Pro Cys Lys Asp Lys
 65                  70                  75 ttc ctg gat gcc ctc ttc ctg tac gac gat gac ggg tac caa tcc tac     769
Phe Leu Asp Ala Leu Phe Leu Tyr Asp Asp Asp Gly Tyr Gln Ser Tyr
 80                  85                  90                  95 tgc tcc atc tgc tgc tcc gga gag acg ctg ctc atc tgc gga aac cct     817
Cys Ser Ile Cys Cys Ser Gly Glu Thr Leu Leu Ile Cys Gly Asn Pro
                100                 105                 110 gat tgc acc cga tgc tac tgc ttc gag tgt gtg gat agc ctg gtc ggc     865
Asp Cys Thr Arg Cys Tyr Cys Phe Glu Cys Val Asp Ser Leu Val Gly
             115                 120                 125 ccc ggg acc tcg ggg aag gtg cac gcc atg agc aac tgg gtg tgc tac     913
Pro Gly Thr Ser Gly Lys Val His Ala Met Ser Asn Trp Val Cys Tyr
         130                 135                 140 ctg tgc ctg ccg tcc tcc cga agc ggg ctg ctg cag cgt cgg agg aag     961
Leu Cys Leu Pro Ser Ser Arg Ser Gly Leu Leu Gln Arg Arg Arg Lys
     145                 150                 155 tgg cgc agc cag ctc aag gcc ttc tac gac cga gag tcg gag aat ccc    1009
Trp Arg Ser Gln Leu Lys Ala Phe Tyr Asp Arg Glu Ser Glu Asn Pro
 160                 165                 170                 175 ctt gag atg ttc gaa acc gtg cct gtg tgg agg aga cag cca gtc cgg    1057
Leu Glu Met Phe Glu Thr Val Pro Val Trp Arg Arg Gln Pro Val Arg
                 180                 185                 190 gtg ctg tcc ctt ttt gaa gac atc aag aaa gag ctg acg agt ttg ggc    1105
Val Leu Ser Leu Phe Glu Asp Ile Lys Lys Glu Leu Thr Ser Leu Gly
```

```
                195                 200                 205
ttt ttg gaa agt ggt tct gac ccg gga caa ctg aag cat gtg gtt gat       1153
Phe Leu Glu Ser Gly Ser Asp Pro Gly Gln Leu Lys His Val Val Asp
            210                 215                 220 gtc aca gac aca gtg agg aag gat gtg gag gag tgg gga ccc ttc gat       1201
Val Thr Asp Thr Val Arg Lys Asp Val Glu Glu Trp Gly Pro Phe Asp
225                 230                 235 ctt gtg tac ggc gcc aca gct ccc ctg ggc cac acc tgt gac cgt cct       1249
Leu Val Tyr Gly Ala Thr Ala Pro Leu Gly His Thr Cys Asp Arg Pro
240                 245                 250                 255 ccc agc tgg tac ctg ttc cag ttc cac cgg ttc ctg cag tac gca cgg       1297
Pro Ser Trp Tyr Leu Phe Gln Phe His Arg Phe Leu Gln Tyr Ala Arg
            260                 265                 270 ccc aag cca ggc agc ccc agg ccc ttc ttc tgg atg ttc gtg gac aat       1345
Pro Lys Pro Gly Ser Pro Arg Pro Phe Phe Trp Met Phe Val Asp Asn
            275                 280                 285 ctg gtg ctg aac aag gaa gac ctg gac gtc gca tct cgc ttc ctg gag       1393
Leu Val Leu Asn Lys Glu Asp Leu Asp Val Ala Ser Arg Phe Leu Glu
            290                 295                 300 atg gag cca gtc acc atc cca gat gtc cac ggc gga tcc ttg cag aat       1441
Met Glu Pro Val Thr Ile Pro Asp Val His Gly Gly Ser Leu Gln Asn
305                 310                 315 gct gtc cgc gtg tgg agc aac atc cca gcc ata agg agc agc agg cac       1489
Ala Val Arg Val Trp Ser Asn Ile Pro Ala Ile Arg Ser Ser Arg His
320                 325                 330                 335 tgg gct ctg gtt tcg gaa gaa gaa ttg tcc ctg ctg gcc cag aac aag       1537
Trp Ala Leu Val Ser Glu Glu Glu Leu Ser Leu Leu Ala Gln Asn Lys
            340                 345                 350 cag agc tcg aag ctc gcg gcc aag tgg ccc acc aag ctg gtg aag aac       1585
Gln Ser Ser Lys Leu Ala Ala Lys Trp Pro Thr Lys Leu Val Lys Asn
            355                 360                 365 tgc ttt ctc ccc cta aga gaa tat ttc aag tat ttt tca aca gaa ctc       1633
Cys Phe Leu Pro Leu Arg Glu Tyr Phe Lys Tyr Phe Ser Thr Glu Leu
            370                 375                 380 act tcc tct tta taaatgagtc actatactgt gaagaaaaag acttttccta          1685
Thr Ser Ser Leu
    385 gaacaaaggc aactttcctc                                                 1705

<210> SEQ ID NO 26
<211> LENGTH: 387
<212> TYPE: PRT
<213> ORGANISM: Homo sapiens

<400> SEQUENCE: 26

Met Ala Ala Ile Pro Ala Leu Asp Pro Glu Ala Glu Pro Ser Met Asp
1               5                   10                  15

Val Ile Leu Val Gly Ser Ser Glu Leu Ser Ser Ser Val Ser Pro Gly
                20                  25                  30

Thr Gly Arg Asp Leu Ile Ala Tyr Glu Val Lys Ala Asn Gln Arg Asn
            35                  40                  45

Ile Glu Asp Ile Cys Ile Cys Cys Gly Ser Leu Gln Val His Thr Gln
        50                  55                  60

His Pro Leu Phe Glu Gly Gly Ile Cys Ala Pro Cys Lys Asp Lys Phe
65                  70                  75                  80

Leu Asp Ala Leu Phe Leu Tyr Asp Asp Gly Tyr Gln Ser Tyr Cys
                85                  90                  95

Ser Ile Cys Cys Ser Gly Glu Thr Leu Leu Ile Cys Gly Asn Pro Asp
                100                 105                 110
```

```
Cys Thr Arg Cys Tyr Cys Phe Glu Cys Val Asp Ser Leu Val Gly Pro
            115                 120                 125
Gly Thr Ser Gly Lys Val His Ala Met Ser Asn Trp Val Cys Tyr Leu
        130                 135                 140
Cys Leu Pro Ser Ser Arg Ser Gly Leu Leu Gln Arg Arg Lys Trp
145                 150                 155                 160
Arg Ser Gln Leu Lys Ala Phe Tyr Asp Arg Glu Ser Glu Asn Pro Leu
                165                 170                 175
Glu Met Phe Glu Thr Val Pro Val Trp Arg Arg Gln Pro Val Arg Val
            180                 185                 190
Leu Ser Leu Phe Glu Asp Ile Lys Lys Glu Leu Thr Ser Leu Gly Phe
        195                 200                 205
Leu Glu Ser Gly Ser Asp Pro Gly Gln Leu Lys His Val Val Asp Val
    210                 215                 220
Thr Asp Thr Val Arg Lys Asp Val Glu Trp Gly Pro Phe Asp Leu
225                 230                 235                 240
Val Tyr Gly Ala Thr Ala Pro Leu Gly His Thr Cys Asp Arg Pro Pro
                245                 250                 255
Ser Trp Tyr Leu Phe Gln Phe His Arg Phe Leu Gln Tyr Ala Arg Pro
            260                 265                 270
Lys Pro Gly Ser Pro Arg Pro Phe Phe Trp Met Phe Val Asp Asn Leu
        275                 280                 285
Val Leu Asn Lys Glu Asp Leu Asp Val Ala Ser Arg Phe Leu Glu Met
    290                 295                 300
Glu Pro Val Thr Ile Pro Asp Val His Gly Gly Ser Leu Gln Asn Ala
305                 310                 315                 320
Val Arg Val Trp Ser Asn Ile Pro Ala Ile Arg Ser Ser Arg His Trp
                325                 330                 335
Ala Leu Val Ser Glu Glu Leu Ser Leu Leu Ala Gln Asn Lys Gln
            340                 345                 350
Ser Ser Lys Leu Ala Ala Lys Trp Pro Thr Lys Leu Val Lys Asn Cys
        355                 360                 365
Phe Leu Pro Leu Arg Glu Tyr Phe Lys Tyr Phe Ser Thr Glu Leu Thr
    370                 375                 380
Ser Ser Leu
385

<210> SEQ ID NO 27
<211> LENGTH: 1560
<212> TYPE: DNA
<213> ORGANISM: Mus musculus
<220> FEATURE:
<221> NAME/KEY: CDS
<222> LOCATION: (147)..(1367)

<400> SEQUENCE: 27
ggtgcatgct aggggcttac gaaggctggt ggtgcagagg ctcccaggcc aggtctttt      60 gtcggtggtg agggacgctc actctcactc cgcgtgctgt ctccccgtct gtgtgctgtg    120
atctcctctg tgagagaagg gccagg atg ttc gag gtc ctg gtg ctg aag att    173
                            Met Phe Glu Val Leu Val Leu Lys Ile
                              1               5 gaa gat cca ggt tgc ttc tgg gta att ata aaa gga tgt agt cat ttt    221
Glu Asp Pro Gly Cys Phe Trp Val Ile Ile Lys Gly Cys Ser His Phe
 10              15                  20                  25 tta gaa caa gaa gtt gac tac caa aaa cta aac act gcc atg aat gac    269
Leu Glu Gln Glu Val Asp Tyr Gln Lys Leu Asn Thr Ala Met Asn Asp
```

```
                          30                  35                  40
ttc tat aac agc atg tgt cag gac gta gaa atg aaa cca tta atg ctg      317
Phe Tyr Asn Ser Met Cys Gln Asp Val Glu Met Lys Pro Leu Met Leu
                    45                  50                  55 gaa gaa ggg cag gtg tgt gtg gtg tac tgc cag gag ctg aag tgc tgg      365
Glu Glu Gly Gln Val Cys Val Val Tyr Cys Gln Glu Leu Lys Cys Trp
                60                  65                  70 tgc agg gct ctg att aag tcc atc atc tct tct gca gac cat tac ctg      413
Cys Arg Ala Leu Ile Lys Ser Ile Ile Ser Ser Ala Asp His Tyr Leu
            75                  80                  85 gca gag tgt ttc ctg gtc gat ttt gcc aag tat att cca gta aaa tct      461
Ala Glu Cys Phe Leu Val Asp Phe Ala Lys Tyr Ile Pro Val Lys Ser
        90                  95                  100                 105 aaa aac atc cga gtt gca gta gag tct ttt atg cag ctt cct tac aga      509
Lys Asn Ile Arg Val Ala Val Glu Ser Phe Met Gln Leu Pro Tyr Arg
                    110                 115                 120 gca aaa aaa ttc aga ctt tac ggt aca aag cct gtg aca ttg cac att      557
Ala Lys Lys Phe Arg Leu Tyr Gly Thr Lys Pro Val Thr Leu His Ile
                125                 130                 135 gac ttc tgt gaa gac aat gct gag att gta cct gcc aca aaa tgg gac      605
Asp Phe Cys Glu Asp Asn Ala Glu Ile Val Pro Ala Thr Lys Trp Asp
            140                 145                 150 agt gca gcc atc cag tac ttt cag aac ctt cta aga gca act acc caa      653
Ser Ala Ala Ile Gln Tyr Phe Gln Asn Leu Leu Arg Ala Thr Thr Gln
        155                 160                 165 gtg gaa gca aaa cta tgt gcg gtg gaa gaa gat act ttt gag gtt tac      701
Val Glu Ala Lys Leu Cys Ala Val Glu Glu Asp Thr Phe Glu Val Tyr
170                 175                 180                 185 ctt tat gca aca ata aaa aat gaa aaa gtt tgt gtt aat gat gac cta      749
Leu Tyr Ala Thr Ile Lys Asn Glu Lys Val Cys Val Asn Asp Asp Leu
                    190                 195                 200 gtt gca aag aat ttt gct tat tat gtg tca cca atg ggg aat aaa aac      797
Val Ala Lys Asn Phe Ala Tyr Tyr Val Ser Pro Met Gly Asn Lys Asn
                205                 210                 215 ctc aat cct ttg gag aaa ccc agg cag agt ctc aat tcg gtg acc tgc      845
Leu Asn Pro Leu Glu Lys Pro Arg Gln Ser Leu Asn Ser Val Thr Cys
            220                 225                 230 tcc agt aag ctc agc cca tca ctt act ctg tgg cca atg ctt cta caa      893
Ser Ser Lys Leu Ser Pro Ser Leu Thr Leu Trp Pro Met Leu Leu Gln
        235                 240                 245 gga aaa gac tat cac aga atg gaa aat aaa gct cta aac tat aag gat      941
Gly Lys Asp Tyr His Arg Met Glu Asn Lys Ala Leu Asn Tyr Lys Asp
250                 255                 260                 265 tcc ttg aca gac tcg cct aaa atg atg ctt gag aag cag cag cag agc      989
Ser Leu Thr Asp Ser Pro Lys Met Met Leu Glu Lys Gln Gln Gln Ser
                    270                 275                 280 ctc cct tta aag cac acg gag aag tgt act gaa tct tct gtg tac tgg      1037
Leu Pro Leu Lys His Thr Glu Lys Cys Thr Glu Ser Ser Val Tyr Trp
                285                 290                 295 cca acc aaa aga ggc ata acc ata tat gct gat cca gat gtt cca tca      1085
Pro Thr Lys Arg Gly Ile Thr Ile Tyr Ala Asp Pro Asp Val Pro Ser
            300                 305                 310 gta agt ggg tct agc cag agg ccg aat gag aag cca ctg cgg ttg act      1133
Val Ser Gly Ser Ser Gln Arg Pro Asn Glu Lys Pro Leu Arg Leu Thr
        315                 320                 325 gaa aag aaa gac tgt gac gag aag aac ggc tgt gta aaa tta ctg cag      1181
Glu Lys Lys Asp Cys Asp Glu Lys Asn Gly Cys Val Lys Leu Leu Gln
330                 335                 340                 345 ttt cta aat cct gat cct ttg aga gct gat ggg acc tca gac ctg cac      1229
Phe Leu Asn Pro Asp Pro Leu Arg Ala Asp Gly Thr Ser Asp Leu His
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     | 350 |     |     |     | 355 |     |     |     | 360 |     |     |     |     |      |
| cag | ttg | cag | aag | gtg | aag | ctg | ggc | aca | ctg | cag | cct | ggg | gtg | gtg | ctc  | 1277 |
| Gln | Leu | Gln | Lys | Val | Lys | Leu | Gly | Thr | Leu | Gln | Pro | Gly | Val | Val | Leu  |
|     |     | 365 |     |     |     | 370 |     |     |     | 375 |     |     |     |     |      |
| cgg | aac | agg | atc | gag | ccc | tgc | cta | acc | ctg | gag | aaa | tca | cct | ctg | tcg  | 1325 |
| Arg | Asn | Arg | Ile | Glu | Pro | Cys | Leu | Thr | Leu | Glu | Lys | Ser | Pro | Leu | Ser  |
|     |     | 380 |     |     |     | 385 |     |     |     | 390 |     |     |     |     |      |
| gca | gac | ctg | aag | aag | gtg | aac | atg | ttc | tta | aag | cca | gac | tcc |     |      | 1367 |
| Ala | Asp | Leu | Lys | Lys | Val | Asn | Met | Phe | Leu | Lys | Pro | Asp | Ser |     |      |
|     |     | 395 |     |     |     | 400 |     |     |     | 405 |     |     |     |     |      | tgacgacatg ccagccctttt ccaacacaga gtgttgcttt gttttgcttt gtctgttctg    1427 ttctaagagt gacggggatg aaatacaggg ctttgcgcgt cctgggcatg cattcatcac    1487 tgaaccatac cccaattcca taggaggatt ttaaataaac acttctaagg ctacattgca    1547 gaattcttgc tcc                                                        1560

<210> SEQ ID NO 28
<211> LENGTH: 407
<212> TYPE: PRT
<213> ORGANISM: Mus musculus

<400> SEQUENCE: 28

Met Phe Glu Val Leu Val Leu Lys Ile Glu Asp Pro Gly Cys Phe Trp
1               5                   10                  15

Val Ile Ile Lys Gly Cys Ser His Phe Leu Glu Gln Glu Val Asp Tyr
            20                  25                  30

Gln Lys Leu Asn Thr Ala Met Asn Asp Phe Tyr Asn Ser Met Cys Gln
        35                  40                  45

Asp Val Glu Met Lys Pro Leu Met Leu Glu Gly Gln Val Cys Val
    50                  55                  60

Val Tyr Cys Gln Glu Leu Lys Cys Trp Cys Arg Ala Leu Ile Lys Ser
65                  70                  75                  80

Ile Ile Ser Ser Ala Asp His Tyr Leu Ala Glu Cys Phe Leu Val Asp
                85                  90                  95

Phe Ala Lys Tyr Ile Pro Val Lys Ser Lys Asn Ile Arg Val Ala Val
            100                 105                 110

Glu Ser Phe Met Gln Leu Pro Tyr Arg Ala Lys Lys Phe Arg Leu Tyr
        115                 120                 125

Gly Thr Lys Pro Val Thr Leu His Ile Asp Phe Cys Glu Asp Asn Ala
    130                 135                 140

Glu Ile Val Pro Ala Thr Lys Trp Asp Ser Ala Ile Gln Tyr Phe
145                 150                 155                 160

Gln Asn Leu Leu Arg Ala Thr Thr Gln Val Glu Ala Lys Leu Cys Ala
                165                 170                 175

Val Glu Glu Asp Thr Phe Glu Val Tyr Leu Tyr Ala Thr Ile Lys Asn
            180                 185                 190

Glu Lys Val Cys Val Asn Asp Leu Val Ala Lys Asn Phe Ala Tyr
        195                 200                 205

Tyr Val Ser Pro Met Gly Asn Lys Asn Leu Asn Pro Leu Glu Lys Pro
    210                 215                 220

Arg Gln Ser Leu Asn Ser Val Thr Cys Ser Ser Lys Leu Ser Pro Ser
225                 230                 235                 240

Leu Thr Leu Trp Pro Met Leu Leu Gln Gly Lys Asp Tyr His Arg Met
                245                 250                 255

Glu Asn Lys Ala Leu Asn Tyr Lys Asp Ser Leu Thr Asp Ser Pro Lys
            260                 265                 270

```
Met Met Leu Glu Lys Gln Gln Gln Ser Leu Pro Leu Lys His Thr Glu
        275                 280                 285
Lys Cys Thr Glu Ser Ser Val Tyr Trp Pro Thr Lys Arg Gly Ile Thr
    290                 295                 300
Ile Tyr Ala Asp Pro Asp Val Pro Ser Val Ser Gly Ser Ser Gln Arg
305                 310                 315                 320
Pro Asn Glu Lys Pro Leu Arg Leu Thr Glu Lys Lys Asp Cys Asp Glu
                325                 330                 335
Lys Asn Gly Cys Val Lys Leu Leu Gln Phe Leu Asn Pro Asp Pro Leu
            340                 345                 350
Arg Ala Asp Gly Thr Ser Asp Leu His Gln Leu Gln Lys Val Lys Leu
        355                 360                 365
Gly Thr Leu Gln Pro Gly Val Val Leu Arg Asn Arg Ile Glu Pro Cys
    370                 375                 380
Leu Thr Leu Glu Lys Ser Pro Leu Ser Ala Asp Leu Lys Lys Val Asn
385                 390                 395                 400
Met Phe Leu Lys Pro Asp Ser
                405

<210> SEQ ID NO 29
<211> LENGTH: 1301
<212> TYPE: DNA
<213> ORGANISM: Homo sapiens
<220> FEATURE:
<221> NAME/KEY: CDS
<222> LOCATION: (97)..(1167)

<400> SEQUENCE: 29
ttacagattg aagatccagg ttgcttctgg gttattataa aagggtgtag tccctttta      60 gatcatgatg tcgattatca aaattaaat agtgcc atg aat gac ttc tac aac      114
                                     Met Asn Asp Phe Tyr Asn
                                       1               5 agc acg tgt caa gat ata gaa ata aaa ccc tta aca ttg gaa gaa gga     162
Ser Thr Cys Gln Asp Ile Glu Ile Lys Pro Leu Thr Leu Glu Glu Gly
               10                  15                  20 cag gtg tgt gtg gtc tat tgt gag gag cta aag tgc tgg tgc agg gcc     210
Gln Val Cys Val Val Tyr Cys Glu Glu Leu Lys Cys Trp Cys Arg Ala
     25                  30                  35 att gtc aaa tca att acg tct tcc gca gac cag tac ctg gca gaa tgt     258
Ile Val Lys Ser Ile Thr Ser Ser Ala Asp Gln Tyr Leu Ala Glu Cys
 40                  45                  50 ttc ctt gtg gac ttt gcc aag aac att cca gtc aaa tct aaa agc atc     306
Phe Leu Val Asp Phe Ala Lys Asn Ile Pro Val Lys Ser Lys Ser Ile
 55                  60                  65                  70 cga gtt gta gta gaa tcg ttt atg cag ctt ccc tat aga gca aaa aaa     354
Arg Val Val Val Glu Ser Phe Met Gln Leu Pro Tyr Arg Ala Lys Lys
                 75                  80                  85 ttc agc ctg tac tgc aca aag cct gtc aca tta cac att gac ttc tgc     402
Phe Ser Leu Tyr Cys Thr Lys Pro Val Thr Leu His Ile Asp Phe Cys
             90                  95                 100 cga gac agt act gac att gtg cct gcc aag aag tgg gac aat gca gct     450
Arg Asp Ser Thr Asp Ile Val Pro Ala Lys Lys Trp Asp Asn Ala Ala
        105                 110                 115 att cag tac ttt cag aac ctt ctg aaa gca act acc cag gtg gaa gcc     498
Ile Gln Tyr Phe Gln Asn Leu Leu Lys Ala Thr Thr Gln Val Glu Ala
    120                 125                 130 aga tta tgt gct gtg gaa gaa gat aca ttt gag gtt tac ctt tat gta     546
Arg Leu Cys Ala Val Glu Glu Asp Thr Phe Glu Val Tyr Leu Tyr Val
135                 140                 145                 150
```

| | | | | | | | | | | | | | | | | |
|---|---|---|---|---|---|---|---|---|---|---|---|---|---|---|---|---|
| act | ata | aaa | gat | gaa | aaa | gtt | tgt | gtt | aat | gat | gat | ctt | gtt | gca | aag | 594 |
| Thr | Ile | Lys | Asp | Glu | Lys | Val | Cys | Val | Asn | Asp | Asp | Leu | Val | Ala | Lys | |
| | | | | 155 | | | | | 160 | | | | | 165 | | |
| aac | tat | gct | tgt | tat | atg | tca | cct | aca | aag | aat | aaa | aac | ctt | gat | tat | 642 |
| Asn | Tyr | Ala | Cys | Tyr | Met | Ser | Pro | Thr | Lys | Asn | Lys | Asn | Leu | Asp | Tyr | |
| | | | 170 | | | | | 175 | | | | | 180 | | | |
| tta | gaa | aaa | cca | aga | ttg | aat | ata | aaa | tca | gca | ccc | tcc | ttc | aat | aaa | 690 |
| Leu | Glu | Lys | Pro | Arg | Leu | Asn | Ile | Lys | Ser | Ala | Pro | Ser | Phe | Asn | Lys | |
| | | 185 | | | | | 190 | | | | | 195 | | | | |
| ctc | aat | cca | gca | ctt | aca | ctc | tgg | cca | atg | ttt | ttg | caa | gga | aaa | gat | 738 |
| Leu | Asn | Pro | Ala | Leu | Thr | Leu | Trp | Pro | Met | Phe | Leu | Gln | Gly | Lys | Asp | |
| | 200 | | | | | 205 | | | | | 210 | | | | | |
| gtt | caa | gga | atg | gaa | gat | tca | cat | ggt | gta | aat | ttt | ccg | gca | caa | tct | 786 |
| Val | Gln | Gly | Met | Glu | Asp | Ser | His | Gly | Val | Asn | Phe | Pro | Ala | Gln | Ser | |
| 215 | | | | | 220 | | | | | 225 | | | | | 230 | |
| ctg | caa | cat | aca | tgg | tgc | aag | ggt | att | gtc | ggt | gac | ctc | agg | cca | aca | 834 |
| Leu | Gln | His | Thr | Trp | Cys | Lys | Gly | Ile | Val | Gly | Asp | Leu | Arg | Pro | Thr | |
| | | | 235 | | | | | 240 | | | | | 245 | | | |
| gcc | aca | gca | cag | gac | aaa | gct | gta | aaa | tgt | aat | atg | gat | tca | ttg | aga | 882 |
| Ala | Thr | Ala | Gln | Asp | Lys | Ala | Val | Lys | Cys | Asn | Met | Asp | Ser | Leu | Arg | |
| | | 250 | | | | | 255 | | | | | 260 | | | | |
| gat | tca | cct | aaa | gac | aaa | tct | gaa | aag | aaa | cac | cat | tgc | atc | tct | tta | 930 |
| Asp | Ser | Pro | Lys | Asp | Lys | Ser | Glu | Lys | Lys | His | His | Cys | Ile | Ser | Leu | |
| | 265 | | | | | 270 | | | | | 275 | | | | | |
| aaa | gat | aca | aat | aag | cgt | gtt | gaa | tcc | tca | gtg | tac | tgg | cca | gca | aaa | 978 |
| Lys | Asp | Thr | Asn | Lys | Arg | Val | Glu | Ser | Ser | Val | Tyr | Trp | Pro | Ala | Lys | |
| 280 | | | | | 285 | | | | | 290 | | | | | | |
| aga | ggc | ata | acc | ata | tat | gct | gat | cca | gat | gta | cca | gaa | gca | agt | gct | 1026 |
| Arg | Gly | Ile | Thr | Ile | Tyr | Ala | Asp | Pro | Asp | Val | Pro | Glu | Ala | Ser | Ala | |
| 295 | | | | 300 | | | | | 305 | | | | | 310 | | |
| tta | agt | cag | aag | tca | aat | gag | aaa | cct | ctt | aga | ttg | act | gag | aag | aaa | 1074 |
| Leu | Ser | Gln | Lys | Ser | Asn | Glu | Lys | Pro | Leu | Arg | Leu | Thr | Glu | Lys | Lys | |
| | | | 315 | | | | | 320 | | | | | 325 | | | |
| gaa | tat | gat | gag | aag | aat | agc | tgt | gtg | aaa | tta | ctg | cag | ttt | tta | aat | 1122 |
| Glu | Tyr | Asp | Glu | Lys | Asn | Ser | Cys | Val | Lys | Leu | Leu | Gln | Phe | Leu | Asn | |
| | | 330 | | | | | 335 | | | | | 340 | | | | |
| cct | gat | cct | ttg | aga | gct | gac | gga | atc | tct | gat | ctc | cag | cag | act | | 1167 |
| Pro | Asp | Pro | Leu | Arg | Ala | Asp | Gly | Ile | Ser | Asp | Leu | Gln | Gln | Thr | | |
| | 345 | | | | | 350 | | | | | 355 | | | | | | tgagattaga agagaaactc cttagatggg ggacttaacc tgaagacatc cttttagaaa   1227 cgatcgaatg gattgttgct tctgagaaat tgttccttgt tttttggata ataaacgatc   1287 ttcctttgg taaa   1301

<210> SEQ ID NO 30
<211> LENGTH: 357
<212> TYPE: PRT
<213> ORGANISM: Homo sapiens

<400> SEQUENCE: 30

Met Asn Asp Phe Tyr Asn Ser Thr Cys Gln Asp Ile Glu Ile Lys Pro
1               5                   10                  15

Leu Thr Leu Glu Glu Gly Gln Val Cys Val Tyr Cys Glu Glu Leu
            20                  25                  30

Lys Cys Trp Cys Arg Ala Ile Val Lys Ser Ile Thr Ser Ser Ala Asp
        35                  40                  45

Gln Tyr Leu Ala Glu Cys Phe Leu Val Asp Phe Ala Lys Asn Ile Pro
    50                  55                  60

Val Lys Ser Lys Ser Ile Arg Val Val Glu Ser Phe Met Gln Leu

-continued

```
              65                  70                  75                  80
Pro Tyr Arg Ala Lys Lys Phe Ser Leu Tyr Cys Thr Lys Pro Val Thr
                    85                  90                  95

Leu His Ile Asp Phe Cys Arg Asp Ser Thr Asp Ile Val Pro Ala Lys
            100                 105                 110

Lys Trp Asp Asn Ala Ala Ile Gln Tyr Phe Gln Asn Leu Leu Lys Ala
        115                 120                 125

Thr Thr Gln Val Glu Ala Arg Leu Cys Ala Val Glu Glu Asp Thr Phe
130                 135                 140

Glu Val Tyr Leu Tyr Val Thr Ile Lys Asp Glu Lys Val Cys Val Asn
145                 150                 155                 160

Asp Asp Leu Val Ala Lys Asn Tyr Ala Cys Tyr Met Ser Pro Thr Lys
                165                 170                 175

Asn Lys Asn Leu Asp Tyr Leu Glu Lys Pro Arg Leu Asn Ile Lys Ser
            180                 185                 190

Ala Pro Ser Phe Asn Lys Leu Asn Pro Ala Leu Thr Leu Trp Pro Met
        195                 200                 205

Phe Leu Gln Gly Lys Asp Val Gln Gly Met Glu Asp Ser His Gly Val
210                 215                 220

Asn Phe Pro Ala Gln Ser Leu Gln His Thr Trp Cys Lys Gly Ile Val
225                 230                 235                 240

Gly Asp Leu Arg Pro Thr Ala Thr Ala Gln Asp Lys Ala Val Lys Cys
                245                 250                 255

Asn Met Asp Ser Leu Arg Asp Ser Pro Lys Asp Lys Ser Glu Lys Lys
            260                 265                 270

His His Cys Ile Ser Leu Lys Asp Thr Asn Lys Arg Val Glu Ser Ser
        275                 280                 285

Val Tyr Trp Pro Ala Lys Arg Gly Ile Thr Ile Tyr Ala Asp Pro Asp
290                 295                 300

Val Pro Glu Ala Ser Ala Leu Ser Gln Lys Ser Asn Glu Lys Pro Leu
305                 310                 315                 320

Arg Leu Thr Glu Lys Lys Glu Tyr Asp Glu Lys Asn Ser Cys Val Lys
                325                 330                 335

Leu Leu Gln Phe Leu Asn Pro Asp Pro Leu Arg Ala Asp Gly Ile Ser
            340                 345                 350

Asp Leu Gln Gln Thr
        355

<210> SEQ ID NO 31
<211> LENGTH: 1280
<212> TYPE: DNA
<213> ORGANISM: Mus musculus
<220> FEATURE:
<221> NAME/KEY: CDS
<222> LOCATION: (122)..(1219)

<400> SEQUENCE: 31 tgagggctg agaagagagc aattcacact tgattagctc ccaggctcct gaattgagca      60
gaggaggcta gaccgctgag ctgcgcaccc cagaggctgc tctaccctgg ctcagacgac     120 c atg cag cct tat caa cgg ctt ctg gcg ctt ggc ttc ctt ctg tta acc     169
  Met Gln Pro Tyr Gln Arg Leu Leu Ala Leu Gly Phe Leu Leu Leu Thr
  1               5                  10                  15 ctg ccc tgg ggc cag aca tcc gag ttt caa gac tct gac ctt ttg cag     217
Leu Pro Trp Gly Gln Thr Ser Glu Phe Gln Asp Ser Asp Leu Leu Gln
            20                  25                  30 ttt ctg gga tta gag aaa gcg cct tca cct cac agg ttc caa cct gtg     265
```

-continued

```
            Phe Leu Gly Leu Glu Lys Ala Pro Ser Pro His Arg Phe Gln Pro Val
                     35                  40                  45 cct cgc gtc tta agg aaa atc atc cgg gct cga gaa gcc gct gca gcc       313
Pro Arg Val Leu Arg Lys Ile Ile Arg Ala Arg Glu Ala Ala Ala Ala
 50                  55                  60 agt ggg gcc tcg cag gac tta tgc tac gtg aag gag ctg ggt gtt cgt       361
Ser Gly Ala Ser Gln Asp Leu Cys Tyr Val Lys Glu Leu Gly Val Arg
 65                  70                  75                  80 ggg aac ctg ctt cag ctt ctc cca gac cag ggt ttt ttc ctt aat aca       409
Gly Asn Leu Leu Gln Leu Leu Pro Asp Gln Gly Phe Phe Leu Asn Thr
                     85                  90                  95 cag aaa cct ttc caa gat ggc tcc tgt ctc cag aag gtc ctc tat ttt       457
Gln Lys Pro Phe Gln Asp Gly Ser Cys Leu Gln Lys Val Leu Tyr Phe
                100                 105                 110 aac ttg tct gcc atc aaa gaa aag gca aag ttg acc atg gcc cag ctg       505
Asn Leu Ser Ala Ile Lys Glu Lys Ala Lys Leu Thr Met Ala Gln Leu
            115                 120                 125 act cta gac ttg ggg ccc agg tcc tac tat aac ctg cga cca gag ctg       553
Thr Leu Asp Leu Gly Pro Arg Ser Tyr Tyr Asn Leu Arg Pro Glu Leu
130                 135                 140 gtg gtt gct ctg tct gtg gtt cag gac cgg ggc gtg tgg ggg cga tcc       601
Val Val Ala Leu Ser Val Val Gln Asp Arg Gly Val Trp Gly Arg Ser
145                 150                 155                 160 cac cct aag gtg ggc aga ttg ctt ttt ctg cgg tct gtc cct ggg cct       649
His Pro Lys Val Gly Arg Leu Leu Phe Leu Arg Ser Val Pro Gly Pro
                165                 170                 175 caa ggt cag ctc cag ttc aac ctg cag ggt gcg ctt aag gat tgg agc       697
Gln Gly Gln Leu Gln Phe Asn Leu Gln Gly Ala Leu Lys Asp Trp Ser
                180                 185                 190 agc aac cga ctg aag aat ttg gac tta cac tta gag att ttg gtc aaa       745
Ser Asn Arg Leu Lys Asn Leu Asp Leu His Leu Glu Ile Leu Val Lys
            195                 200                 205 gag gac aga tac tcc agg gta act gtc cag ccc gag aac ccc tgt gac       793
Glu Asp Arg Tyr Ser Arg Val Thr Val Gln Pro Glu Asn Pro Cys Asp
210                 215                 220 ccg ctg ctc cgc tct cta cat gcc tcg ctg ctg gta acc ctc aat           841
Pro Leu Leu Arg Ser Leu His Ala Ser Leu Leu Val Thr Leu Asn
225                 230                 235                 240 cct aaa cac tgt cat cct tct tcc aga aaa agg agg gcg gcc atc tct       889
Pro Lys His Cys His Pro Ser Ser Arg Lys Arg Arg Ala Ala Ile Ser
                245                 250                 255 gtc ccc aag ggt ttc tgt agg aac ttc tgc cac cgt cat cag ctg ttc       937
Val Pro Lys Gly Phe Cys Arg Asn Phe Cys His Arg His Gln Leu Phe
                260                 265                 270 atc aac ttc cag gac ctg ggt tgg cac aag tgg gtc atc gcc cct aag       985
Ile Asn Phe Gln Asp Leu Gly Trp His Lys Trp Val Ile Ala Pro Lys
            275                 280                 285 ggg ttc atg gca aat tac tgt cat gga gag tgc ccc ttc tca atg acc      1033
Gly Phe Met Ala Asn Tyr Cys His Gly Glu Cys Pro Phe Ser Met Thr
290                 295                 300 acg tat tta aat agt tcc aat tat gct ttc atg cag gct ctg atg cat      1081
Thr Tyr Leu Asn Ser Ser Asn Tyr Ala Phe Met Gln Ala Leu Met His
305                 310                 315                 320 atg gct gac ccc aag gtc ccc aag gct gtc tgt gtc ccc acc aag ctc      1129
Met Ala Asp Pro Lys Val Pro Lys Ala Val Cys Val Pro Thr Lys Leu
                325                 330                 335 tcg ccc atc tcc atg ctc tat cag gat agt gat aag aac gtc att ctc      1177
Ser Pro Ile Ser Met Leu Tyr Gln Asp Ser Asp Lys Asn Val Ile Leu
                340                 345                 350 cga cat tat gaa gac atg gta gtc gat gag tgt ggg tgt ggg              1219
Arg His Tyr Glu Asp Met Val Val Asp Glu Cys Gly Cys Gly
```

```
Arg His Tyr Glu Asp Met Val Val Asp Glu Cys Gly Cys Gly
        355                 360                 365 tagtctcggg actaggctag gagtgtgctt agggtaaatc ctttaataaa actaccaccc     1279
c                                                                    1280

<210> SEQ ID NO 32
<211> LENGTH: 366
<212> TYPE: PRT
<213> ORGANISM: Mus musculus

<400> SEQUENCE: 32

Met Gln Pro Tyr Gln Arg Leu Leu Ala Leu Gly Phe Leu Leu Leu Thr
 1               5                  10                  15

Leu Pro Trp Gly Gln Thr Ser Glu Phe Gln Asp Ser Asp Leu Leu Gln
                20                  25                  30

Phe Leu Gly Leu Glu Lys Ala Pro Ser Pro His Arg Phe Gln Pro Val
            35                  40                  45

Pro Arg Val Leu Arg Lys Ile Ile Arg Ala Arg Glu Ala Ala Ala Ala
     50                  55                  60

Ser Gly Ala Ser Gln Asp Leu Cys Tyr Val Lys Glu Leu Gly Val Arg
 65                  70                  75                  80

Gly Asn Leu Leu Gln Leu Pro Asp Gln Gly Phe Phe Leu Asn Thr
                85                  90                  95

Gln Lys Pro Phe Gln Asp Gly Ser Cys Leu Gln Lys Val Leu Tyr Phe
                100                 105                 110

Asn Leu Ser Ala Ile Lys Glu Lys Ala Lys Leu Thr Met Ala Gln Leu
            115                 120                 125

Thr Leu Asp Leu Gly Pro Arg Ser Tyr Tyr Asn Leu Arg Pro Glu Leu
        130                 135                 140

Val Val Ala Leu Ser Val Val Gln Asp Arg Gly Val Trp Gly Arg Ser
145                 150                 155                 160

His Pro Lys Val Gly Arg Leu Leu Phe Leu Arg Ser Val Pro Gly Pro
                165                 170                 175

Gln Gly Gln Leu Gln Phe Asn Leu Gln Gly Ala Leu Lys Asp Trp Ser
            180                 185                 190

Ser Asn Arg Leu Lys Asn Leu Asp Leu His Leu Glu Ile Leu Val Lys
        195                 200                 205

Glu Asp Arg Tyr Ser Arg Val Thr Val Gln Pro Glu Asn Pro Cys Asp
    210                 215                 220

Pro Leu Leu Arg Ser Leu His Ala Ser Leu Leu Val Val Thr Leu Asn
225                 230                 235                 240

Pro Lys His Cys His Pro Ser Ser Arg Lys Arg Arg Ala Ala Ile Ser
                245                 250                 255

Val Pro Lys Gly Phe Cys Arg Asn Phe Cys His Arg His Gln Leu Phe
            260                 265                 270

Ile Asn Phe Gln Asp Leu Gly Trp His Lys Trp Val Ile Ala Pro Lys
        275                 280                 285

Gly Phe Met Ala Asn Tyr Cys His Gly Glu Cys Pro Phe Ser Met Thr
    290                 295                 300

Thr Tyr Leu Asn Ser Ser Asn Tyr Ala Phe Met Gln Ala Leu Met His
305                 310                 315                 320

Met Ala Asp Pro Lys Val Pro Lys Ala Val Cys Val Pro Thr Lys Leu
                325                 330                 335

Ser Pro Ile Ser Met Leu Tyr Gln Asp Ser Asp Lys Asn Val Ile Leu
            340                 345                 350
```

```
Arg His Tyr Glu Asp Met Val Val Asp Glu Cys Gly Cys Gly
        355                 360                 365

<210> SEQ ID NO 33
<211> LENGTH: 1224
<212> TYPE: DNA
<213> ORGANISM: Homo sapiens
<220> FEATURE:
<221> NAME/KEY: CDS
<222> LOCATION: (37)..(1128)

<400> SEQUENCE: 33
ggagctctcc ccggtctgac agccactcca gaggcc atg ctt cgt ttc ttg cca         54
                                       Met Leu Arg Phe Leu Pro
                                        1               5 gat ttg gct ttc agc ttc ctg tta att ctg gct ttg ggc cag gca gtc        102
Asp Leu Ala Phe Ser Phe Leu Leu Ile Leu Ala Leu Gly Gln Ala Val
            10                  15                  20 caa ttt caa gaa tat gtc ttt ctc caa ttt ctg ggc tta gat aag gcg        150
Gln Phe Gln Glu Tyr Val Phe Leu Gln Phe Leu Gly Leu Asp Lys Ala
        25                  30                  35 cct tca ccc cag aag ttc caa cct gtg cct tat atc ttg aag aaa att        198
Pro Ser Pro Gln Lys Phe Gln Pro Val Pro Tyr Ile Leu Lys Lys Ile
 40                  45                  50 ttc cag gat cgc gag gca gca gcg acc act ggg gtc tcc cga gac tta        246
Phe Gln Asp Arg Glu Ala Ala Ala Thr Thr Gly Val Ser Arg Asp Leu
 55                  60                  65                  70 tgc tac gta aag gag ctg ggc gtc cgc ggg aat gta ctt cgc ttt ctc        294
Cys Tyr Val Lys Glu Leu Gly Val Arg Gly Asn Val Leu Arg Phe Leu
                 75                  80                  85 cca gac caa ggt ttc ttt ctt tac cca aag aaa att tcc caa gct tcc        342
Pro Asp Gln Gly Phe Phe Leu Tyr Pro Lys Lys Ile Ser Gln Ala Ser
            90                  95                 100 tcc tgc ctg cag aag ctc ctc tac ttt aac ctg tct gcc atc aaa gaa        390
Ser Cys Leu Gln Lys Leu Leu Tyr Phe Asn Leu Ser Ala Ile Lys Glu
        105                 110                 115 agg gaa cag ttg aca ttg gcc cag ctg ggc ctg gac ttg ggg ccc aat        438
Arg Glu Gln Leu Thr Leu Ala Gln Leu Gly Leu Asp Leu Gly Pro Asn
120                 125                 130 tct tac tat aac ctg gga cca gag ctg gaa ctg gct ctg ttc ctg gtt        486
Ser Tyr Tyr Asn Leu Gly Pro Glu Leu Glu Leu Ala Leu Phe Leu Val
135                 140                 145                 150 cag gag cct cat gtg tgg ggc cag acc acc cct aag cca ggt aaa atg        534
Gln Glu Pro His Val Trp Gly Gln Thr Thr Pro Lys Pro Gly Lys Met
                155                 160                 165 ttt gtg ttg cgg tca gtc cca tgg cca caa ggt gct gtt cac ttc aac        582
Phe Val Leu Arg Ser Val Pro Trp Pro Gln Gly Ala Val His Phe Asn
            170                 175                 180 ctg ctg gat gta gct aag gat tgg aat gac aac ccc cgg aaa aat ttc        630
Leu Leu Asp Val Ala Lys Asp Trp Asn Asp Asn Pro Arg Lys Asn Phe
        185                 190                 195 ggg tta ttc ctg gag ata ctg gtc aaa gaa gat aga gac tca ggg gtg        678
Gly Leu Phe Leu Glu Ile Leu Val Lys Glu Asp Arg Asp Ser Gly Val
    200                 205                 210 aat ttt cag cct gaa gac acc tgt gcc aga cta aga tgc tcc ctt cat        726
Asn Phe Gln Pro Glu Asp Thr Cys Ala Arg Leu Arg Cys Ser Leu His
215                 220                 225                 230 gct tcc ctg ctg gtg gtg act ctc aac cct gat cag tgc cac cct tct        774
Ala Ser Leu Leu Val Val Thr Leu Asn Pro Asp Gln Cys His Pro Ser
                235                 240                 245 cgg aaa agg aga gca gcc atc cct gtc ccc aag ctt tct tgt aag aac        822
```

```
Arg Lys Arg Arg Ala Ile Pro Val Pro Lys Leu Ser Cys Lys Asn
            250                 255                 260 ctc tgc cac cgt cac cag cta ttc att aac ttc cgg gac ctg ggt tgg      870
Leu Cys His Arg His Gln Leu Phe Ile Asn Phe Arg Asp Leu Gly Trp
            265                 270                 275 cac aag tgg atc att gcc ccc aag ggg ttc atg gca aat tac tgc cat      918
His Lys Trp Ile Ile Ala Pro Lys Gly Phe Met Ala Asn Tyr Cys His
            280                 285                 290 gga gag tgt ccc ttc tca ctg acc atc tct ctc aac agc tcc aat tat      966
Gly Glu Cys Pro Phe Ser Leu Thr Ile Ser Leu Asn Ser Ser Asn Tyr
295                 300                 305                 310 gct ttc atg caa gcc ctg atg cat gcc gtt gac cca gag atc ccc cag     1014
Ala Phe Met Gln Ala Leu Met His Ala Val Asp Pro Glu Ile Pro Gln
                315                 320                 325 gct gtg tgt atc ccc acc aag ctg tct ccc att tcc atg ctc tac cag     1062
Ala Val Cys Ile Pro Thr Lys Leu Ser Pro Ile Ser Met Leu Tyr Gln
                330                 335                 340 gac aat aat gac aat gtc att cta cga cat tat gaa gac atg gta gtc     1110
Asp Asn Asn Asp Asn Val Ile Leu Arg His Tyr Glu Asp Met Val Val
            345                 350                 355 gat gaa tgt ggg tgt ggg taggatgtca gaaatgggaa tagaaggagt             1158
Asp Glu Cys Gly Cys Gly
            360 gttcttaggg taaatctttt aataaaacta cctatctggt ttatgaccac ttagatcgaa   1218 atgtca                                                              1224

<210> SEQ ID NO 34
<211> LENGTH: 364
<212> TYPE: PRT
<213> ORGANISM: Homo sapiens

<400> SEQUENCE: 34

Met Leu Arg Phe Leu Pro Asp Leu Ala Phe Ser Phe Leu Leu Ile Leu
 1               5                  10                  15

Ala Leu Gly Gln Ala Val Gln Phe Gln Glu Tyr Val Phe Leu Gln Phe
            20                  25                  30

Leu Gly Leu Asp Lys Ala Pro Ser Pro Gln Lys Phe Gln Pro Val Pro
        35                  40                  45

Tyr Ile Leu Lys Lys Ile Phe Gln Asp Arg Glu Ala Ala Ala Thr Thr
    50                  55                  60

Gly Val Ser Arg Asp Leu Cys Tyr Val Lys Glu Leu Gly Val Arg Gly
65                  70                  75                  80

Asn Val Leu Arg Phe Leu Pro Asp Gln Gly Phe Phe Leu Tyr Pro Lys
                85                  90                  95

Lys Ile Ser Gln Ala Ser Ser Cys Leu Gln Lys Leu Leu Tyr Phe Asn
            100                 105                 110

Leu Ser Ala Ile Lys Glu Arg Glu Gln Leu Thr Leu Ala Gln Leu Gly
        115                 120                 125

Leu Asp Leu Gly Pro Asn Ser Tyr Tyr Asn Leu Gly Pro Glu Leu Glu
    130                 135                 140

Leu Ala Leu Phe Leu Val Gln Glu Pro His Val Trp Gly Gln Thr Thr
145                 150                 155                 160

Pro Lys Pro Gly Lys Met Phe Val Leu Arg Ser Val Pro Trp Pro Gln
                165                 170                 175

Gly Ala Val His Phe Asn Leu Leu Asp Val Ala Lys Asp Trp Asn Asp
            180                 185                 190

Asn Pro Arg Lys Asn Phe Gly Leu Phe Leu Glu Ile Leu Val Lys Glu
```

```
                   195                 200                 205
Asp Arg Asp Ser Gly Val Asn Phe Gln Pro Glu Asp Thr Cys Ala Arg
        210                 215                 220

Leu Arg Cys Ser Leu His Ala Ser Leu Leu Val Val Thr Leu Asn Pro
225                 230                 235                 240

Asp Gln Cys His Pro Ser Arg Lys Arg Arg Ala Ala Ile Pro Val Pro
                    245                 250                 255

Lys Leu Ser Cys Lys Asn Leu Cys His Arg His Gln Leu Phe Ile Asn
            260                 265                 270

Phe Arg Asp Leu Gly Trp His Lys Trp Ile Ile Ala Pro Lys Gly Phe
        275                 280                 285

Met Ala Asn Tyr Cys His Gly Glu Cys Pro Phe Ser Leu Thr Ile Ser
    290                 295                 300

Leu Asn Ser Ser Asn Tyr Ala Phe Met Gln Ala Leu Met His Ala Val
305                 310                 315                 320

Asp Pro Glu Ile Pro Gln Ala Val Cys Ile Pro Thr Lys Leu Ser Pro
                    325                 330                 335

Ile Ser Met Leu Tyr Gln Asp Asn Asn Asp Asn Val Ile Leu Arg His
            340                 345                 350

Tyr Glu Asp Met Val Val Asp Glu Cys Gly Cys Gly
        355                 360

<210> SEQ ID NO 35
<211> LENGTH: 1248
<212> TYPE: DNA
<213> ORGANISM: Mus musculus
<220> FEATURE:
<221> NAME/KEY: CDS
<222> LOCATION: (32)..(1003)

<400> SEQUENCE: 35
agtggatccc ccgggctgca ggaattccgg g atg gat cct cga acc tgg cta         52
                                   Met Asp Pro Arg Thr Trp Leu
                                     1               5 agc ttc caa ggg cct cca ggt ggg cct gga atc gga cca ggc tca gag       100
Ser Phe Gln Gly Pro Pro Gly Gly Pro Gly Ile Gly Pro Gly Ser Glu
         10                  15                  20 gta ttg ggg atc tcc cca tgt ccg ccc gca tac gag ttc tgc gga ggg       148
Val Leu Gly Ile Ser Pro Cys Pro Pro Ala Tyr Glu Phe Cys Gly Gly
 25                  30                  35 atg gca tac tgt gga cct cag gtt ggt ctg ggc cta gtc ccc caa gtt       196
Met Ala Tyr Cys Gly Pro Gln Val Gly Leu Gly Leu Val Pro Gln Val
 40                  45                  50                  55 ggc gtg gag act ttg cag cct gag ggc cag gca gga gca cga gtg gaa       244
Gly Val Glu Thr Leu Gln Pro Glu Gly Gln Ala Gly Ala Arg Val Glu
                 60                  65                  70 agc aac tca gag gga acc tcc tct gag ccc tgt gcc gac cgc ccc aat       292
Ser Asn Ser Glu Gly Thr Ser Ser Glu Pro Cys Ala Asp Arg Pro Asn
             75                  80                  85 gcc gtg aag ttg gag aag gtg gaa cca act ccc gag gag tcc cag gac       340
Ala Val Lys Leu Glu Lys Val Glu Pro Thr Pro Glu Glu Ser Gln Asp
         90                  95                 100 atg aaa gcc ctg cag aag gag cta gaa cag ttt gcc aag ctg ctg aag       388
Met Lys Ala Leu Gln Lys Glu Leu Glu Gln Phe Ala Lys Leu Leu Lys
105                 110                 115 cag aag agg atc acc ttg ggg tac acc cag gcc gac gtg ggg ctc acc       436
Gln Lys Arg Ile Thr Leu Gly Tyr Thr Gln Ala Asp Val Gly Leu Thr
120                 125                 130                 135 ctg ggc gtt ctc ttt gga aag gtg ttc agc cag acc acc atc tgt cgc       484
```

-continued

| | | | | | | | | | | | | |
|---|---|---|---|---|---|---|---|---|---|---|---|---|
|Leu|Gly|Val|Leu 140|Phe|Gly|Lys|Val|Phe 145|Ser|Gln|Thr|Thr Ile Cys Arg 150|

| | | | | | | | | | | | | | |
|---|---|---|---|---|---|---|---|---|---|---|---|---|---|
|ttc|gag|gcc|ttg|cag|ctc|agc|ctt|aag|aac|atg|tgt|aag|ctg cgg ccc|532|
|Phe|Glu|Ala|Leu 155|Gln|Leu|Ser|Leu|Lys 160|Asn|Met|Cys|Lys 165|Leu Arg Pro| ctg ctg gag aag tgg gtg gag gaa gcc gac aac aat gag aac ctt cag   580
Leu Leu Glu Lys Trp Val Glu Glu Ala Asp Asn Asn Glu Asn Leu Gln
        170                 175                 180 gag ata tgc aaa tcg gag acc ctg gtg cag gcc cgg aag aga aag cga   628
Glu Ile Cys Lys Ser Glu Thr Leu Val Gln Ala Arg Lys Arg Lys Arg
    185                 190                 195 act agc att gag aac cgt gtg agg tgg agt ctg gag acc atg ttt ctg   676
Thr Ser Ile Glu Asn Arg Val Arg Trp Ser Leu Glu Thr Met Phe Leu
200                 205                 210                 215 aag tgc ccg aag ccc tcc cta cag cag atc act cac atc gcc aat cag   724
Lys Cys Pro Lys Pro Ser Leu Gln Gln Ile Thr His Ile Ala Asn Gln
                220                 225                 230 ctt ggg cta gag aag gat gtg gtt cga gta tgg ttc tgt aac cgg cgc   772
Leu Gly Leu Glu Lys Asp Val Val Arg Val Trp Phe Cys Asn Arg Arg
            235                 240                 245 cag aag ggc aaa aga tca agt att gag tat tcc caa cga gaa gag tat   820
Gln Lys Gly Lys Arg Ser Ser Ile Glu Tyr Ser Gln Arg Glu Glu Tyr
        250                 255                 260 gag gct aca ggg aca cct ttc cca ggg ggg gct gta tcc ttt cct ctg   868
Glu Ala Thr Gly Thr Pro Phe Pro Gly Gly Ala Val Ser Phe Pro Leu
    265                 270                 275 ccc cca ggt ccc cac ttt ggc acc cca ggc tat gga agc ccc cac ttc   916
Pro Pro Gly Pro His Phe Gly Thr Pro Gly Tyr Gly Ser Pro His Phe
280                 285                 290                 295 acc aca ctc tac tca gtc cct ttt cct gag ggc gag gcc ttt ccc tct   964
Thr Thr Leu Tyr Ser Val Pro Phe Pro Glu Gly Glu Ala Phe Pro Ser
                300                 305                 310 gtt ccc gtc act gct ctg ggc tct ccc atg cat tca aac tgaggcacca   1013
Val Pro Val Thr Ala Leu Gly Ser Pro Met His Ser Asn
            315                 320 gccctccctg gggatgctgt gagccaaggc aagggaggta gacaagagaa cctggagctt   1073 tgggggttaaa ttcttttact gaggagggat taaaagcaca acaggggtgg ggggtgggat   1133
ggggaaagaa gctcagtgat gctgttgatc aggagcctgg cctgtctgtc actcatcatt   1193
ttgttcttaa ataaagactg ggacacacag taaaaaaaaa aaaaaaaaac tcgag   1248

<210> SEQ ID NO 36
<211> LENGTH: 324
<212> TYPE: PRT
<213> ORGANISM: Mus musculus

<400> SEQUENCE: 36

Met Asp Pro Arg Thr Trp Leu Ser Phe Gln Gly Pro Pro Gly Gly Pro
1               5                   10                  15

Gly Ile Gly Pro Gly Ser Glu Val Leu Gly Ile Ser Pro Cys Pro Pro
            20                  25                  30

Ala Tyr Glu Phe Cys Gly Gly Met Ala Tyr Cys Gly Pro Gln Val Gly
        35                  40                  45

Leu Gly Leu Val Pro Gln Val Gly Val Glu Thr Leu Gln Pro Glu Gly
    50                  55                  60

Gln Ala Gly Ala Arg Val Glu Ser Asn Ser Glu Gly Thr Ser Ser Glu
65                  70                  75                  80

Pro Cys Ala Asp Arg Pro Asn Ala Val Lys Leu Glu Lys Val Glu Pro
                85                  90                  95

```
Thr Pro Glu Glu Ser Gln Asp Met Lys Ala Leu Gln Lys Glu Leu Glu
            100                 105                 110

Gln Phe Ala Lys Leu Leu Lys Gln Lys Arg Ile Thr Leu Gly Tyr Thr
        115                 120                 125

Gln Ala Asp Val Gly Leu Thr Leu Gly Val Leu Phe Gly Lys Val Phe
    130                 135                 140

Ser Gln Thr Thr Ile Cys Arg Phe Glu Ala Leu Gln Leu Ser Leu Lys
145                 150                 155                 160

Asn Met Cys Lys Leu Arg Pro Leu Leu Glu Lys Trp Val Glu Glu Ala
                165                 170                 175

Asp Asn Asn Glu Asn Leu Gln Glu Ile Cys Lys Ser Glu Thr Leu Val
            180                 185                 190

Gln Ala Arg Lys Arg Lys Arg Thr Ser Ile Glu Asn Arg Val Arg Trp
        195                 200                 205

Ser Leu Glu Thr Met Phe Leu Lys Cys Pro Lys Pro Ser Leu Gln Gln
    210                 215                 220

Ile Thr His Ile Ala Asn Gln Leu Gly Leu Glu Lys Asp Val Val Arg
225                 230                 235                 240

Val Trp Phe Cys Asn Arg Arg Gln Lys Gly Lys Arg Ser Ser Ile Glu
                245                 250                 255

Tyr Ser Gln Arg Glu Glu Tyr Glu Ala Thr Gly Thr Pro Phe Pro Gly
            260                 265                 270

Gly Ala Val Ser Phe Pro Leu Pro Pro Gly Pro His Phe Gly Thr Pro
        275                 280                 285

Gly Tyr Gly Ser Pro His Phe Thr Thr Leu Tyr Ser Val Pro Phe Pro
    290                 295                 300

Glu Gly Glu Ala Phe Pro Ser Val Pro Val Thr Ala Leu Gly Ser Pro
305                 310                 315                 320

Met His Ser Asn

<210> SEQ ID NO 37
<211> LENGTH: 1371
<212> TYPE: DNA
<213> ORGANISM: Homo sapiens
<220> FEATURE:
<221> NAME/KEY: CDS
<222> LOCATION: (43)..(1122)

<400> SEQUENCE: 37
ctcatttcac caggccccg gcttggggcg ccttccttcc cc atg gcg gga cac        54
                                              Met Ala Gly His
                                                1 ctg gct tcg gat ttc gcc ttc tcg ccc cct cca ggt ggt gga ggt gat    102
Leu Ala Ser Asp Phe Ala Phe Ser Pro Pro Pro Gly Gly Gly Gly Asp
  5                  10                  15                  20 ggg cca ggg ggg ccg gag ccg ggc tgg gtt gat cct cgg acc tgg cta    150
Gly Pro Gly Gly Pro Glu Pro Gly Trp Val Asp Pro Arg Thr Trp Leu
                 25                  30                  35 agc ttc caa ggc cct cct gga ggg cca gga atc ggg ccg ggg gtt ggg    198
Ser Phe Gln Gly Pro Pro Gly Gly Pro Gly Ile Gly Pro Gly Val Gly
             40                  45                  50 cca ggc tct gag gtg tgg ggg att ccc cca tgc ccc ccg ccg tat gag    246
Pro Gly Ser Glu Val Trp Gly Ile Pro Pro Cys Pro Pro Pro Tyr Glu
         55                  60                  65 ttc tgt ggg ggg atg gcg tac tgt ggg ccc cag gtt gga gtg ggg cta    294
Phe Cys Gly Gly Met Ala Tyr Cys Gly Pro Gln Val Gly Val Gly Leu
     70                  75                  80
```

| | |
|---|---|
| gtg ccc caa ggc ggc ttg gag acc tct cag cct gag ggc gaa gca gga<br>Val Pro Gln Gly Gly Leu Glu Thr Ser Gln Pro Glu Gly Glu Ala Gly<br>85                    90                    95                    100 | 342 |
| gtc ggg gtg gag agc aac tcc gat ggg gcc tcc ccg gag ccc tgc acc<br>Val Gly Val Glu Ser Asn Ser Asp Gly Ala Ser Pro Glu Pro Cys Thr<br>                    105                    110                    115 | 390 |
| gtc acc cct ggt gcc gtg aag ctg gag aag gag aag ctg gag caa aac<br>Val Thr Pro Gly Ala Val Lys Leu Glu Lys Glu Lys Leu Glu Gln Asn<br>              120                    125                    130 | 438 |
| ccg gag gag tcc cag gac atc aaa gct ctg cag aaa gaa ctc gag caa<br>Pro Glu Glu Ser Gln Asp Ile Lys Ala Leu Gln Lys Glu Leu Glu Gln<br>            135                    140                    145 | 486 |
| ttt gcc aag ctc ctg aag cag aag agg atc acc ctg gga tat aca cag<br>Phe Ala Lys Leu Leu Lys Gln Lys Arg Ile Thr Leu Gly Tyr Thr Gln<br>150                    155                    160 | 534 |
| gcc gat gtg ggg ctc acc ctg ggg gtt cta ttt ggg aag gta ttc agc<br>Ala Asp Val Gly Leu Thr Leu Gly Val Leu Phe Gly Lys Val Phe Ser<br>165                    170                    175                    180 | 582 |
| caa acg acc atc tgc cgc ttt gag gct ctg cag ctt agc ttc aag aac<br>Gln Thr Thr Ile Cys Arg Phe Glu Ala Leu Gln Leu Ser Phe Lys Asn<br>                    185                    190                    195 | 630 |
| atg tgt aag ctg cgg ccc ttg ctg cag aag tgg gtg gag gaa gct gac<br>Met Cys Lys Leu Arg Pro Leu Leu Gln Lys Trp Val Glu Glu Ala Asp<br>            200                    205                    210 | 678 |
| aac aat gaa aat ctt cag gag ata tgc aaa gca gaa acc ctc gtg cag<br>Asn Asn Glu Asn Leu Gln Glu Ile Cys Lys Ala Glu Thr Leu Val Gln<br>              215                    220                    225 | 726 |
| gcc cga aag aga aag cga acc agt atc gag aac cga gtg aga ggc aac<br>Ala Arg Lys Arg Lys Arg Thr Ser Ile Glu Asn Arg Val Arg Gly Asn<br>230                    235                    240 | 774 |
| ctg gag aat ttg ttc ctg cag tgc ccg aaa ccc aca ctg cag cag atc<br>Leu Glu Asn Leu Phe Leu Gln Cys Pro Lys Pro Thr Leu Gln Gln Ile<br>245                    250                    255                    260 | 822 |
| agc cac atc gcc cag cag ctt ggg ctc gag aag gat gtg gtc cga gtg<br>Ser His Ile Ala Gln Gln Leu Gly Leu Glu Lys Asp Val Val Arg Val<br>                    265                    270                    275 | 870 |
| tgg ttc tgt aac cgg cgc cag aag ggc aag cga tca agc agc gac tat<br>Trp Phe Cys Asn Arg Arg Gln Lys Gly Lys Arg Ser Ser Ser Asp Tyr<br>            280                    285                    290 | 918 |
| gca caa cga gag gat ttt gag gct gct ggg tct cct ttc tca ggg gga<br>Ala Gln Arg Glu Asp Phe Glu Ala Ala Gly Ser Pro Phe Ser Gly Gly<br>              295                    300                    305 | 966 |
| cca gtg tcc ttt cct ctg gcc cca ggg ccc cat ttt ggt acc cca ggc<br>Pro Val Ser Phe Pro Leu Ala Pro Gly Pro His Phe Gly Thr Pro Gly<br>310                    315                    320 | 1014 |
| tat ggg agc cct cac ttc act gca ctg tac tcc tcg gtc cct ttc cct<br>Tyr Gly Ser Pro His Phe Thr Ala Leu Tyr Ser Ser Val Pro Phe Pro<br>325                    330                    335                    340 | 1062 |
| gag ggg gaa gcc ttt ccc cct gtc tct gtc acc act ctg ggc tct ccc<br>Glu Gly Glu Ala Phe Pro Pro Val Ser Val Thr Thr Leu Gly Ser Pro<br>                    345                    350                    355 | 1110 |
| atg cat tca aac tgaggtgcct gcccttctag gaatggggga caggggagg<br>Met His Ser Asn<br>            360 | 1162 |
| ggaggagcta gggaaagaaa acctggagtt tgtgccaggg tttttggatt aagttcttca | 1222 |
| ttcactaagg aaggaattgg gaacacaaag ggtgggggca ggggagtttg gggcaactgg | 1282 |
| ttggagggaa ggtgaagttc aatgatgctc ttgattttaa tcccacatca tgtatcactt | 1342 |
| ttttcttaaa taaagaagct tgggacaca | 1371 |

```
<210> SEQ ID NO 38
<211> LENGTH: 360
<212> TYPE: PRT
<213> ORGANISM: Homo sapiens

<400> SEQUENCE: 38

Met Ala Gly His Leu Ala Ser Asp Phe Ala Phe Ser Pro Pro Pro Gly
  1               5                  10                  15

Gly Gly Gly Asp Gly Pro Gly Gly Pro Glu Pro Gly Trp Val Asp Pro
             20                  25                  30

Arg Thr Trp Leu Ser Phe Gln Gly Pro Pro Gly Gly Pro Gly Ile Gly
             35                  40                  45

Pro Gly Val Gly Pro Gly Ser Glu Val Trp Gly Ile Pro Pro Cys Pro
 50                  55                  60

Pro Pro Tyr Glu Phe Cys Gly Gly Met Ala Tyr Cys Gly Pro Gln Val
 65                  70                  75                  80

Gly Val Gly Leu Val Pro Gln Gly Gly Leu Glu Thr Ser Gln Pro Glu
                 85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 39
<211> LENGTH: 24
```

```
<212> TYPE: DNA
<213> ORGANISM: Artificial Sequence
<220> FEATURE:
<223> OTHER INFORMATION: Description of Artificial Sequence:primer

<400> SEQUENCE: 39
agggtctgct actgagatgc tctg                                          24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 40
aggcaggtct tcagaggaag ggcg                                          24

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 41
cgggctgtag acctgtctgc attctg                                        26

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 42
ggtccttctg tctcatcctc gagagt                                        26

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 43
accaaggtca ccgcatccaa                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 44
cttcaccaag atttccgatg                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 45
gaatggtgga ctagcttttg                                               20
```

```
<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 46
tgccatgaat gtcgatatgc ag                                          22

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 47
ccgcggaaag tcaagagatt gggtgg                                      26

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 48
gcggccgcct ttacgggtca cgagggtcac                                  30

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 49
tgtggccagt gtttggttct ggcggg                                      26

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 50
ctcgaggact cgccattcta gccaag                                      26
```

SCREENING METHOD FOR SOMATIC CELL NUCLEAR REPROGRAMMING SUBSTANCE AFFECTING ECAT2 AND ECAT3

TECHNICAL FIELD

The present invention relates to a new screening method for a substance that reprograms somatic cell nucleus. More specifically, the present invention relates to a method of efficiently identifying a substance that induces the conversion of somatic cells to ES-like cells (a substance that induces somatic cell nuclear reprogramming) by monitoring the conversion to ES-like cells by the expression of a marker gene utilizing an ECAT gene. The present invention also relates to a method of efficiently selecting ES-like cells by monitoring the conversion to ES-like cells by the expression of a marker gene utilizing an ECAT gene. Furthermore, the present invention still also relates to a method of efficiently selecting a substance for the maintenance of undifferentiated state and pluripotency of ES cells by monitoring the maintenance of undifferentiated state and pluripotency of ES cells (maintenance of ES cell properties) by the expression of a marker gene utilizing an ECAT gene.

BACKGROUND ART

Embryonic stem cells (ES cells) are stem cells established from an inner cell mass of mammalian blastocyst, and can be infinitely grown while maintaining their potential for differentiating into all types of cells (pluripotency). Focusing on this characteristic, there is expectation for stem cell therapy, which comprises treating a patient with myocardial infarction or Parkinson's disease by transplanting myocardial cells or nerve cells produced in large amounts from ES cells. However, ES cells involve the critical ethical issue of utilizing and sacrificing human fertilized eggs. On the other hand, tissue stem cells such as neural stem cells, hematopoietic stem cells, and mesenchymal stem cells are present in individual tissues of a living body. Tissue stem cells do not involve the ethical issue because of the non-use of a fertilized egg, and avoid graft rejection because of the possible use of cells from the patient. However, tissue stem cells are difficult to isolate and the growth potential and differentiation potential thereof are much poorer than those of ES cells. If somatic cells such as tissue stem cells and differentiated cells can be converted to cells similar to ES cells having high growth potential and pluripotency by any means, the resulting ES-like cells would be ideal stem cells for clinical application. Specifically, it is hoped, for example, that somatic cells collected from a patient will be stimulated with a nuclear reprogramming factor (a factor for inducing nuclear reprogramming) to convert to ES-like cells, which ES-like cells will be clinically applied as stem cells. However, there is no system enabling the efficient search of such a nuclear reprogramming factor.

The term ECAT gene (ES cell associated transcript gene) generically refers to a series of genes specifically expressed in totipotent cells such as ES cells. A reported ECAT gene is the transcription factor Oct3 (also called Oct4 or POU5f1; hereinafter referred to as Oct3/4) gene. Although a similar gene has been reported in humans (hOct3/4 gene; Takeda et al., Nucleic Acids Research, 20:4613-4620 (1992)), there is no report of demonstrating the ES-cell-specific expression of the hOct-3/4 gene.

In recent years, our group has found nine genes specifically expressed in ES cells on the basis of computerized analysis utilizing an EST database and Northern blot analysis, and designating them as ECAT1 gene, ECAT2 gene, ECAT3 gene, ECAT4 gene, ECAT5 gene, the ECAT gene 6 gene, ECAT7 gene, ECAT8 gene, and ECAT9 gene (International Patent Publication No. WO 02/097090). Of these, ECAT4 is a factor also called Nanog, and has been shown to be an essential factor for the maintenance of the totipotency (pluripotency) of ES cells (Mitsui, K., et al., Cell, 113: 631-642 (2003)). ECAT5 is a factor also called ERas, and has been shown to promote the growth of ES cells (Takahashi, K., et al., Nature, 423: 541-545 (2003)).

ECAT3 is a kind of F-box-containing protein, namely Fbx15, and is considered to be a ubiquitin ligase because it has the F-box. As a result of an analysis of the expression control region of the ECAT3 gene, ECAT3 was shown to undergo cooperative expression control by the two ES-cell-specific transcription factors Oct4 and Sox2 (Tokuzawa, Y., et al., Molecular and Cellular Biology, 23(8): 2699-2708 (2003)).

As a result of an analysis of a knock-in mouse resulting from knocking in β geo (the fusion gene of the β galactosidase and neomycin resistance genes) to the coding region of the ECAT3 gene, performed to examine the function of ECAT3, no evident abnormalities were observed in the mouse, nor was there any evident abnormality in the growth or differentiation potential of homozygous mutant ES cells. Based on this finding, the ECAT3 gene is considered not to be an essential factor for the maintenance and growth of ES cells (Tokuzawa, Y., et al., Molecular and Cellular Biology, 23(8): 2699-2708 (2003)).

DISCLOSURE OF THE INVENTION

It is an object of the present invention to provide a system for efficiently selecting ES-like cells utilizing an ECAT gene, and a screening method for a somatic cell (tissue stem cell, differentiated cell) nuclear reprogramming substance utilizing the same system. It is another object of the present invention to provide a screening method for a substance for the maintenance of undifferentiated state and pluripotency of ES cells utilizing an ECAT gene.

As described above, if somatic cells can be converted to cells similar to ES cells having high growth potential and pluripotency by any means, the resulting ES-like cells would be ideal stem cells for clinical application. The present inventor diligently investigated in search for a method enabling efficient screening for a substance that induces such conversion to ES-like cells (somatic cell nuclear reprogramming substance).

The present inventor first prepared somatic cells wherein a marker gene is present at a position permitting expression control by the expression control region of an ECAT gene. Specifically, somatic cells (lymphocytes) were prepared from a knock-in mouse wherein the β geo gene, which is a marker gene, was knocked in to the ECAT3 gene. These somatic cells were cultured under culture conditions for ES cell and selected using G418; all these cells died, with absolutely no drug resistant colony obtained. On the other hand, the aforementioned somatic cells were fused with normal ES cells, cultured under culture conditions for ES cell, and selected using G418; surviving cells emerged. As a result of an analysis of these surviving cells, they were found to express ECAT4 and Oct3/4, and hence to be ES-like cells having ES cell properties. From these experimental results, it was shown that the ES-like cells emerged due to the reprogramming of the nuclei of the somatic cells by fusion of the somatic cells and ES cells, and that the somatic cells became drug resistant due to the expression of β geo in place of the ECAT3 gene.

As described above, somatic cells comprising a gene wherein a marker gene is present at a position permitting expression control by the expression control region of the ECAT3 gene express the marker gene only when converted to ES-like cells. Hence, it is possible to easily monitor the conversion to ES-like cells by the expression of a marker gene such as a drug resistance gene. Utilizing this property, a nuclear reprogramming factor that induces the conversion of somatic cells to ES-like cells can be efficiently screened with the expression of a marker gene such as a drug resistance gene as an index. Likewise, it is possible to efficiently select ES-like cells with the expression of the aforementioned marker gene as an index.

The present inventor and others further found that not only ECAT3 but also other ECATs such as ECAT2 and ECAT5 could e utilized for the aforementioned screening and selection of ES-like cells. Because all ECAT genes (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene) are known to be specifically expressed in ES cells, all ECATs can be used for the aforementioned screening. In particular, provided that an ECAT gene is destroyed by a technique such as knock-in, ECAT2 and ECAT3, which are not essential for the maintenance and growth of ES cells, are highly effectively utilized.

Furthermore, the aforementioned system for "easily monitoring the conversion to ES-like cells by the expression of a marker gene such as a drug resistance gene" can also be applied to screening for a substance for the maintenance of undifferentiated state and pluripotency of ES cells. Mouse ES cells permit the maintenance of undifferentiated state and pluripotency using a cytokine LIF. Furthermore, in the case of a large number of cells, mouse ES cells can be maintained using a serum-free medium supplemented with LIF without the use of feeder cells. However, at low densities, serum or feeder cells are essential. This indicates that an ES cell maintenance factor other than LIF is contained in serum and the secretion products of feeder cells. Although some of human ES cells can maintain their undifferentiated state and pluripotency on mouse feeder cells, not all cells can be maintained to remain undifferentiated. Furthermore, unlike in mouse ES cells, LIF is ineffective in human ES cells. This also suggests that feeder cells may secrete a factor for the maintenance of undifferentiated state and pluripotency of ES cells other than LIF, and also suggests the necessity of an additional factor differing from any secretion product of the feeder cells. When human ES cells are clinically applied, it is essential to culture them without the use of animal serum or feeder cells, and there is a demand for the identification of a factor for the maintenance of undifferentiated state and pluripotency of ES cells, but no method of efficient identification has been found.

According to the aforementioned system of the present invention, it is possible to easily monitor the ES cell state by the expression of a marker gene such as a drug resistance gene; therefore, it is possible to easily screen for a substance (candidate) for the maintenance of undifferentiated state and pluripotency of ES cells by, for example, adding a test substance under culture conditions not allowing the maintenance of the ES cell state, and determining the presence or absence of cells expressing the marker gene.

The present invention was developed based on these findings.

Accordingly, the present invention provides the following:
(1) a screening method for a somatic cell nuclear reprogramming substance, which comprises the following steps (a) and (b):
(a) a step for bringing into contact with each other a somatic cell comprising a gene wherein a marker gene is present at a position permitting expression control by the expression control region of an ECAT gene, and a test substance,
(b) a step following the aforementioned step (a), for determining the presence or absence of the emergence of cells expressing the marker gene, and selecting a test substance allowing the emergence of the cells as a somatic cell nuclear reprogramming substance candidate,
(2) the screening method described in (1) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,
(3) the screening method described in (1) or (2) above, wherein the marker gene is a drug resistance gene, a fluorescent protein gene, a luminescent enzyme gene, a chromogenic enzyme gene or a gene comprising a combination thereof,
(4) the screening method described in any of (1) to (3) above, wherein the somatic cell is a somatic cell comprising a gene resulting from knocking in the marker gene to the ECAT gene,
(5) the screening method described in (4) above, wherein the somatic cell is a somatic cell homozygously comprising the gene resulting from knocking in the marker gene to the ECAT gene,
(6) the screening method described in (4) or (5) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,
(7) the screening method described in (1) above, which comprises the following steps (a) and (b):
(a) a step for bringing into contact with each other a somatic cell comprising a gene resulting from knocking in a gene comprising a drug resistance gene to the ECAT2 gene, and a test substance,
(b) a step following the aforementioned step (a), for determining the presence or absence of surviving cells in a selection medium, and selecting a test substance allowing the emergence of the surviving cells as a somatic cell nuclear reprogramming substance candidate,
(8) the screening method described in (1) above, which comprises the following steps (a) and (b):
(a) a step for bringing into contact with each other a somatic cell comprising a gene resulting from knocking in a gene comprising a drug resistance gene to the ECAT3 gene, and a test substance,
(b) a step following the aforementioned step (a), for determining the presence or absence of surviving cells in a selection medium, and selecting a test substance allowing the emergence of the surviving cells as a somatic cell nuclear reprogramming substance candidate,
(9) the screening method described in (1) above, which comprises the following steps (a) and (b):
(a) a step for bringing into contact with each other a somatic cell comprising a gene resulting from knocking in a gene comprising a drug resistance gene to the ECAT5 gene, and a test substance,
(b) a step following the aforementioned step (a), for determining the presence or absence of surviving cells in a selection medium, and selecting a test substance allowing the emergence of the surviving cells as a somatic cell nuclear reprogramming substance candidate,
(10) the screening method described in (1) above, which comprises the following steps (a) and (b):
(a) a step for bringing into contact with each other a somatic cell comprising genes resulting from knocking in a gene comprising a drug resistance gene to each of the ECAT2 gene and ECAT3 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate,

(11) the screening method described in (10) above, wherein the different drug resistance genes have been knocked in to ECAT2 gene and the ECAT3 gene,

(12) the screening method described in any of (7) to (11) above, wherein the somatic cell is a somatic cell homozygously comprising a gene resulting from knocking in a gene comprising a drug resistance gene to an ECAT gene,

(13) the screening method described in (1) above, which comprises the following steps (a) and (b):

(a) a step for bringing into contact with each other a somatic cell comprising a gene resulting from knocking in a gene comprising a drug resistance gene to the ECAT4 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate,

(14) the screening method described in (13) above, wherein the somatic cell is a somatic cell heterozygously comprising a gene resulting from knocking in a gene comprising a drug resistance gene to the ECAT4 gene,

(15) the screening method described in (13) above, which comprises the following steps (a) and (b):

(a) a step for supplying ECAT4 to a somatic cell comprising a gene resulting from knocking in a gene comprising a drug resistance gene to the ECAT4 gene, and bringing it into contact with a test substance, (b) a step following the aforementioned step (a), for determining the presence or absence of surviving cells in a selection medium, and selecting a test substance allowing the emergence of the surviving cells as a somatic cell nuclear reprogramming substance candidate,

(16) the screening method described in (15) above, wherein the somatic cell is a somatic cell homozygously comprising a gene resulting from knocking in a gene comprising a drug resistance gene to the ECAT4 gene,

(17) a nuclear reprogramming substance selected using the screening method described in any of (1) to (16) above,

(18) the nuclear reprogramming substance described in (17) above, which is a gene or protein derived from ES cells,

(19) the nuclear reprogramming substance described in (18) above, wherein the ES cell is an ES cell with the NAT1 gene destroyed,

(20) a substance derived from ES cells with the NAT1 gene destroyed,

(21) the substance described in (20) above, which is a cDNA library, a protein library, or a cell extract,

(22) a use of a knock-in mouse comprising a gene resulting from knocking in a marker gene to an ECAT gene as a source of the somatic cell used in the screening method described in any of (1) to (16) above,

(23) the use described in (22) above, wherein the knock-in mouse is a knock-in mouse homozygously comprising a gene resulting from knocking in a marker gene to an ECAT gene,

(24) the use described in (22) or (23) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(25) the use described in any of (22) to (24) above, wherein the marker gene is a drug resistance gene, a fluorescent protein gene, a luminescent enzyme gene, a chromogenic enzyme gene or a gene comprising a combination thereof,

(26) a somatic cell comprising a gene wherein a marker gene is present at a position permitting expression control by the expression control region of an ECAT gene,

(27) the somatic cell described in (26) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(28) the somatic cell described in (26) or (27) above, wherein the marker gene is a drug resistance gene, a fluorescent protein gene, a luminescent enzyme gene, a chromogenic enzyme gene or a gene comprising a combination thereof,

(29) the somatic cell described in any of (26) to (28) above, which comprises a gene resulting from knocking in a marker gene to an ECAT gene,

(30) the somatic cell described in (29) above, which homozygously comprises a gene resulting from knocking in a marker gene to an ECAT gene,

(31) the somatic cell described in (30) above, which is a differentiated ES cell homozygously comprising a gene resulting from knocking in a marker gene to the ECAT4 gene,

(32) the somatic cell described in (31) above, into which ECAT4 has been supplied,

(33) a selection method for ES-like cells, which comprises the following steps (a) and (b):

(a) a step for bringing into contact with each other a somatic cell comprising a gene wherein a marker gene is present at a position permitting expression control by the expression control region of an ECAT gene, and a somatic cell nuclear reprogramming substance, (b) a step following the aforementioned step (a), for selecting cells expressing the marker gene as ES-like cells,

(34) the selection method described in (33) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(35) the selection method described in (33) or (34) above, wherein the marker gene is a drug resistance gene, a fluorescent protein gene, a luminescent enzyme gene, a chromogenic enzyme gene or a gene comprising a combination thereof,

(36) the selection method described in (33) above, which comprises the following steps (a) and (b):

(a) a step for bringing into contact with each other a somatic cell comprising a gene wherein a drug resistance gene is present at a position permitting expression control by the expression control region of the ECAT2 gene, and a somatic cell nuclear reprogramming substance, (b) a step following the aforementioned step (a), for selecting surviving cells in a selection medium as ES-like cells,

(37) the selection method described in (33) above, which comprises the following steps (a) and (b):

(a) a step for bringing into contact with each other a somatic cell comprising a gene wherein a drug resistance gene is present at a position permitting expression control by the expression control region of the ECAT3 gene, and a somatic cell nuclear reprogramming substance, (b) a step following the aforementioned step (a), for selecting surviving cells in a selection medium as ES-like cells,

(38) the selection method described in (33) above, which comprises the following steps (a) and (b):
(a) a step for bringing into contact with each other a somatic cell comprising a gene wherein a drug resistance gene is present at a position permitting expression control by the expression control region of the ECAT5 gene, and a somatic cell nuclear reprogramming substance,
(b) a step following the aforementioned step (a), for selecting surviving cells in a selection medium as ES-like cells,

(39) the selection method described in (33) above, which comprises the following steps (a) and (b):
(a) a step for bringing into contact with each other a somatic cell comprising genes wherein a drug resistance gene is present at a position permitting expression control by the expression control region of each of the ECAT2 gene and the ECAT3 gene, and a somatic cell nuclear reprogramming substance,
(b) a step following the aforementioned step (a), for selecting surviving cells in a selection medium as ES-like cells,

(40) the selection method described in (39) above, wherein mutually different drug resistance genes are present at the positions permitting expression control by the expression control regions of the ECAT2 gene and the ECAT3 gene,

(41) the selection method described in (33) above, which comprises the following steps (a) and (b):
(a) a step for bringing into contact with each other a somatic cell comprising a gene wherein a drug resistance gene is present at a position permitting expression control by the expression control region of the ECAT4 gene, and a somatic cell nuclear reprogramming substance,
(b) a step following the aforementioned step (a), for selecting surviving cells in a selection medium as ES-like cells,

(42) the selection method described in any of (33) to (41) above, wherein the somatic cell is a somatic cell comprising a vector incorporating a marker gene at a position permitting expression control by the expression control region of an ECAT gene,

(43) the selection method described in (42) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(44) a use of the somatic cell described in any of (26) to (32) above in the screening method described in any of (1) to (16) above or the selection method described in any of (33) to (43) above,

(45) a cell expressing the marker gene or surviving cell that as emerged in the screening method described in any of (1) to (16) above, or an ES-like cells selected in the selection method described in any of (33) to (43) above,

(46) a screening method for a substance for the maintenance of undifferentiated state and pluripotency of ES cells, which comprises the following steps (a) and (b):
(a) a step for bringing an ES cell comprising a gene wherein a marker gene is present at a position permitting expression control by the expression control region of an ECAT gene into contact with a test substance in a medium not allowing the maintenance of undifferentiated state and pluripotency of ES cells,
(b) a step following the aforementioned step (a), for determining the presence or absence of cells expressing the marker gene, and selecting a test substance allowing the occurrence of the cells as a candidate substance for the maintenance of undifferentiated state and pluripotency of ES cells,

(47) the screening method described in (46) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(48) the screening method described in (46) or (47) above, wherein the marker gene is a drug resistance gene, a fluorescent protein gene, a luminescent enzyme gene, a chromogenic enzyme gene or a gene comprising a combination thereof,

(49) the screening method described in any of (46) to (48) above, wherein the ES cell is an ES cell comprising a gene resulting from knocking in a marker gene to an ECAT gene,

(50) the screening method described in (49) above, wherein the ES cell is an ES cell homozygously comprising a gene resulting from knocking in a marker gene to an ECAT gene,

(51) the screening method described in (49) or (50) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(52) the screening method described in (46) above, which comprises the following steps (a) and (b):
(a) a step for bringing an ES cell comprising a gene resulting from knocking in a gene comprising a drug resistance gene to the ECAT2 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(53) the screening method described in (46) above, which comprises the following steps (a) and (b):
(a) a step for bringing an ES cell comprising a gene resulting from knocking in a gene comprising a drug resistance gene to the ECAT3 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(54) the screening method described in (46) above, which comprises the following steps (a) and (b):
(a) a step for bringing an ES cell comprising a gene resulting from knocking in a gene comprising a drug resistance gene to the ECAT5 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(55) the screening method described in (46) above, which comprises the following steps (a) and (b):
(a) a step for bringing an ES cell comprising genes resulting from knocking in a gene comprising a drug resistance gene to each of the ECAT2 gene and the ECAT3 gene into contact with a test substance in a medium not allowing the maintenance of undifferentiated state and pluripotency of ES cells, (b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(56) the screening method described in (55) above, wherein the different drug resistance genes have been knocked in to ECAT2 gene and the ECAT3 gene,

(57) the screening method described in any of (52) to (56) above, wherein the ES cell is an ES cell homozygously comprising a gene resulting from knocking in a gene comprising a drug resistance gene to an ECAT gene,

(58) the screening method described in (46) above, which comprises the following steps (a) and (b):

(a) a step for bringing an ES cell comprising a gene resulting from knocking in a gene comprising a drug resistance gene to the ECAT4 gene into contact with a test substance in a medium not allowing the maintenance of undifferentiated state and pluripotency of ES cells, (b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,

(59) the screening method described in (58) above, wherein the ES cell is an ES cell heterozygously comprising a gene resulting from knocking in a gene comprising a drug resistance gene to the ECAT4 gene,

(60) a substance for the maintenance of undifferentiated state and pluripotency of ES cells selected using the screening method described in any of (46) to (59) above,

(61) the substance for the maintenance of undifferentiated state and pluripotency of ES cells described in (60) above, which is a secretion product of feeder cells,

(62) the substance for the maintenance of undifferentiated state and pluripotency of ES cells described in (60) above, which is a serum-derived component,

(63) a use of a knock-in mouse comprising a gene resulting from knocking in a marker gene to an ECAT gene as a source of the ES cell used in the screening method described in any of (46) to (59) above,

(64) the use described in (63) above, wherein the knock-in mouse is a knock-in mouse homozygously comprising a gene resulting from knocking in a marker gene to an ECAT gene,

(65) the use described in (63) or (64) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(66) the use described in any of (63) to (65) above, wherein the marker gene is a drug resistance gene, a fluorescent protein gene, a luminescent enzyme gene, a chromogenic enzyme gene or a gene comprising a combination thereof,

(67) an ES cell comprising a gene wherein a marker gene is present at a position permitting expression control by the expression control region of an ECAT gene,

(68) the ES cell described in (67) above, wherein the ECAT gene is one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene,

(69) the ES cell described in (67) or (68) above, wherein the marker gene is a drug resistance gene, a fluorescent protein gene, a luminescent enzyme gene, a chromogenic enzyme gene or a gene comprising a combination thereof,

(70) the ES cell described in any of (67) to (69) above, which comprises a gene resulting from knocking in a marker gene to an ECAT gene,

(71) the ES cell described in (70) above, which homozygously comprises a gene resulting from knocking in a marker gene to an ECAT gene, and

(72) a use of the ES cell described in any of (67) to (71) above in the screening method described in any of (46) to (59) above.

BEST MODE FOR EMBODYING THE INVENTION

Figure 1:
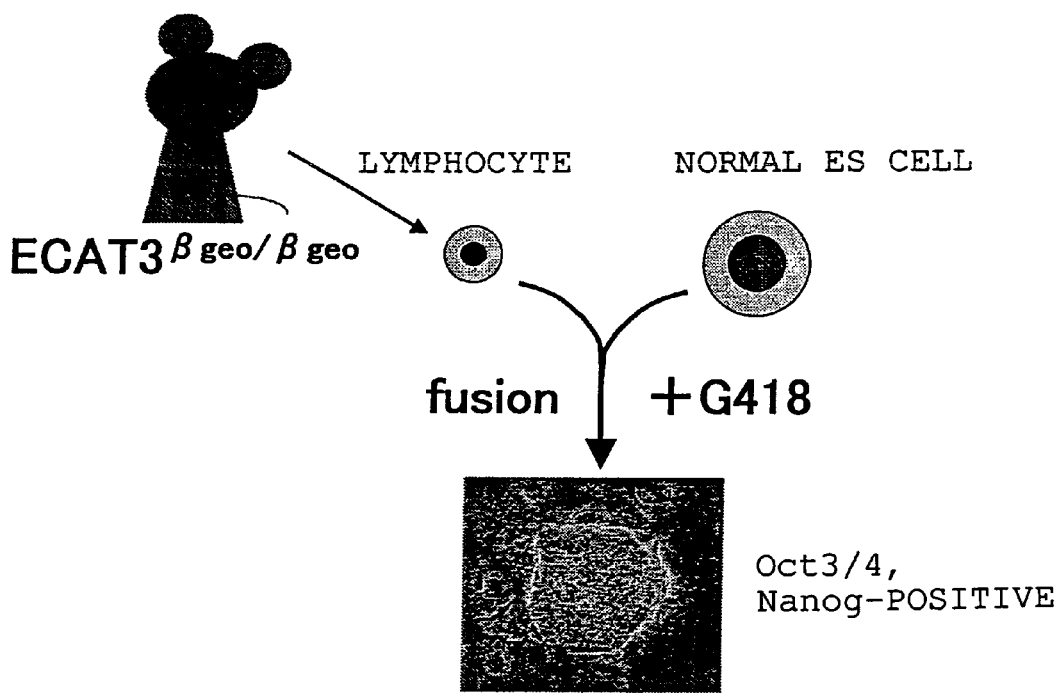
FIG. 1 is a drawing showing an outline of Example 1. It is shown that fusion of lymphocytes isolated from an ECAT3$^{\beta geo/\beta geo}$ mouse and normal ES cells, and selection with G418 resulted in the emergence of ES-like cells positive for Oct3/4 and Nanog (ECAT4).

Abbreviations for amino acids, (poly)peptides, (poly)nucleotides and the like used in the present description are based on the IUPAC-IUB rules [IUPAC-IUB Communication on Biological Nomenclature, Eur. J. Biochem., 138:9 (1984)], "Guideline for the Preparation of Descriptions etc. Including Base Sequences or Amino Acid Sequences" (edited by the Japan Patent Office), or abbreviations in common use in relevant fields.

"The ECAT gene (ES cell associated transcript gene)", as used herein generically refers to a series of genes specifically expressed in totipotent cells such as ES cells. Specifically, the ECAT1 gene, ECAT2 gene, ECAT3 gene, ECAT4 gene, ECAT5 gene, ECAT6 gene, ECAT7 gene, ECAT8 gene, ECAT9 gene, and Oct3/4 gene can be mentioned (International Patent Publication No. WO 02/097090). The term ECAT gene as used herein sometimes refers not only to the cDNA (mRNA) of ECAT, but also to the genomic DNA of ECAT, depending on the technical contents.

The mouse and human types of base sequences and amino acid sequences of these ECAT cDNAs are described in International Patent Publication No. WO 02/097090. They are shown by the following sequence identification numbers in the sequence listing of the present description.

TABLE 1

| ECAT gene | Mouse type base sequence | Mouse type amino acid sequence | Human type base sequence | Human type amino acid sequence |
|---|---|---|---|---|
| ECAT1 | SEQ ID NO: 1 | SEQ ID NO: 2 | SEQ ID NO: 3 | SEQ ID NO: 4 |
| ECAT2 | SEQ ID NO: 5 | SEQ ID NO: 6 | SEQ ID NO: 7 | SEQ ID NO: 8 |
| ECAT3 | SEQ ID NO: 9 | SEQ ID NO: 10 | SEQ ID NO: 11 | SEQ ID NO: 12 |
| ECAT4 | SEQ ID NO: 13 | SEQ ID NO: 14 | SEQ ID NO: 15 | SEQ ID NO: 16 |
| ECAT5 | SEQ ID NO: 17 | SEQ ID NO: 18 | SEQ ID NO: 19 | SEQ ID NO: 20 |
| ECAT6 | SEQ ID NO: 21 | SEQ ID NO: 22 | | |
| ECAT7 | SEQ ID NO: 23 | SEQ ID NO: 24 | SEQ ID NO: 25 | SEQ ID NO: 26 |
| ECAT8 | SEQ ID NO: 27 | SEQ ID NO: 28 | SEQ ID NO: 29 | SEQ ID NO: 30 |
| ECAT9 | SEQ ID NO: 31 | SEQ ID NO: 32 | SEQ ID NO: 33 | SEQ ID NO: 34 |
| Oct3/4 | SEQ ID NO: 35 | SEQ ID NO: 36 | SEQ ID NO: 37 | SEQ ID NO: 38 |

In the category of "ECAT genes" (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene), not only the genes comprising any of the base sequences shown by the aforementioned sequence identification numbers, but also the genes comprising any base sequence similar to these base sequences, are included, as long as they are specifically expressed in ES cells.

"The gene comprising a similar base sequence" as used herein refers to a gene comprising a base sequence resulting from the deletion, substitution or addition of one or more bases in any of the base sequences shown by the aforementioned sequence identification numbers and a gene comprising a base sequence having a high homology to any of the base sequences shown by the aforementioned sequence identification numbers can be mentioned.

"A gene comprising a base sequence having a high homology" as used herein means a gene that hybridizes with each ECAT gene under stringent conditions; specifically, a gene comprising a base sequence having a homology of 70% or more, preferably 80% or more, more preferably 90% or more, and particularly preferably 95% or more, to the base sequence shown by any of the aforementioned sequence identification numbers can be mentioned. Stringent conditions as mentioned herein can be adjusted by changing the temperatures, salt concentrations and the like during the hybridization reaction and washing as appropriate, and are set according to desired homology; for example, conditions involving a salt concentration of 6×SSC and a temperature of 65° C. can be mentioned.

In the category of "ECAT" (ECAT1, ECAT2, ECAT3, ECAT4, ECAT5, ECAT6, ECAT7, ECAT8, ECAT9 and Oct3/4), not only the proteins comprising any of the amino acid sequences shown by the aforementioned sequence identification numbers, but also the proteins comprising any amino acid sequence similar to these amino acid sequences, are included, as long as they are specifically expressed in ES cells.

"A protein comprising a similar amino acid sequence" as mentioned herein refers to a protein encoded by a gene comprising the aforementioned similar base sequence.

The screening method of the present invention is a method of efficiently identifying a somatic cell nuclear reprogramming substance (a substance that induces the conversion to ES-like cells) by using somatic cells wherein a marker gene is present at a position permitting expression control by the expression control region of an ECAT gene as the cells for screening, bringing a test substance into contact with the cells, and monitoring the conversion of the somatic cells to ES-like cells by the presence or absence of the emergence of cells expressing the marker gene. The present method is specifically described below.

(1) The Screening Method of the Present Invention for Somatic Cell Nuclear Reprogramming Substance The present invention provides a screening method for a somatic cell nuclear reprogramming substance, which comprises the following steps (a) and (b):

(a) a step for bringing into contact with each other a somatic cell comprising a gene wherein a marker gene is present at a position permitting expression control by the expression control region of an ECAT gene and a test substance, (b) a step following the aforementioned step (a), for determining the presence or absence of the emergence of cells expressing the marker gene, and selecting a test substance allowing the emergence of the cells as a somatic cell nuclear reprogramming substance candidate, Specifically, as the aforementioned "ECAT gene", one or more genes selected from among the ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene can be mentioned. The "one or more" as mentioned herein specifically refers to one or a combination of two to three ECAT genes, with preference given to one ECAT gene or a combination of two ECAT genes. Specifically, the ECAT2 gene, the ECAT3 gene, or a combination of the ECAT2 gene and the ECAT3 gene can be mentioned as examples.

Although the aforementioned ECAT gene may be an ECAT gene derived from any species such as mouse, rat, human, or monkey, with preference given to an ECAT gene derived from mouse or human.

The aforementioned "marker gene" refers to any gene that enables cell sorting and selection by introducing the marker gene into cells. Specifically, a drug resistance gene, a fluorescent protein gene, a luminescent enzyme gene, a chromogenic enzyme gene or a gene comprising a combination thereof can be mentioned.

Specifically, as the drug resistance gene, the neomycin resistance gene (neo), tetracycline resistance gene (tet), kanamycin resistance gene, zeocin resistance gene (zeo), hygromycin resistance gene (hygro) and the like can be mentioned. When cells are cultured using a medium comprising each drug (referred to as a selection medium), only those cells incorporating and expressing the drug resistance gene survive. Therefore, by culturing cells using a selection medium, it is possible to easily select cells comprising a drug resistance gene.

Specifically, as the fluorescent protein gene, the GFP (green fluorescent protein) gene, YFP (yellow fluorescent protein) gene, RFP (red fluorescent protein) gene, aequorin gene and the like can be mentioned. Cells expressing these fluorescent protein genes can be detected using a fluorescence microscope. The cells can also be selected by separation and selection using a cell sorter and the like on the basis of differences in fluorescence intensity, or by subjecting the cells to limiting dilution to obtain a cell density of not more than one cell per well, then culturing and growing the cells, and detecting cells (wells) producing fluorescence under a fluorescence microscope. Furthermore, it is also possible to allow colonies to form on a soft agar medium and the like, and to select colonies under a fluorescence microscope and the like.

Specifically, as the luminescent enzyme gene, the luciferase gene and the like can be mentioned. Cells expressing these luminescent enzyme genes can be detected by measuring the amount of luminescence using a luminescence photometer with the addition of a luminescent substrate. The cells can also be selected by subjecting the cells to limiting dilution to obtain a cell density of not more than one cell per well, then culturing and growing the cells, collecting a portion of the cells from each well, and measuring the presence or absence of luminescence with the addition of a luminescent substrate using a luminescence photometer.

Specifically, as the chromogenic enzyme gene, the β galactosidase gene, β glucuronidase gene, alkaline phosphatase gene, or secreted alkaline phosphatase SEAP gene and the like can be mentioned. Cells expressing these chromogenic enzyme genes can be detected by examining for chromogenic in the presence of a chromogenic substrate. The cells can also be selected by subjecting the cells to limiting dilution to obtain a cell density of not more than one cell per well, then culturing and growing the cells, collecting a portion of the cells from each well, and adding a chromogenic substrate to examine for chromogenic.

Specifically, as the gene comprising a combination of these marker genes, the β geo gene, which is the fusion gene of the neomycin resistance gene (neo) and the β galactosidase gene (β-gal), can be mentioned.

All the above-described marker genes are well known to those skilled in the art; vectors harboring such a marker gene are commercially available from Invitrogen, Inc., Amersham Biosciences, Inc., Promega, Inc., MBL (Medical & Biological Laboratories Co., Ltd.) and the like.

Of the aforementioned marker genes, a drug resistance gene or a gene comprising the drug resistance gene is particularly preferable because of the ease of cell selection.

"Somatic cells" as mentioned above means any cells except cells that maintain undifferentiated state and pluripotency, such as normal ES cells. Specifically, as examples, (1) tissue stem cells (somatic stem cells) such as neural stem cells, hematopoietic stem cells, mesenchymal stem cells, and spermatogonial stem cells, (2) tissue progenitor cells, (3) differentiated cells such as lymphocytes, epithelial cells, myocytes, and fibroblasts, (4) cells obtained by depriving ES cells of their undifferentiated state and pluripotency by any technique, (5) cells that are fusion cells of somatic cells and ES cells, and that do not have an undifferentiated state and pluripotency, and the like can be mentioned.

"The ES-like cells" resulting from conversion of somatic cells by a nuclear reprogramming substance means cells having ES cell properties, that is, cells having undifferentiated state and pluripotency.

In the screening method of the present invention, somatic cells comprising a gene wherein a marker gene is present at a position permitting expression control by the expression control region of an ECAT gene are used as the cells for screening.

The "expression control region" as mentioned herein refers to a region for regulating the expression (transcription) of a gene, meaning a region comprising "a promoter region" or "promoter and enhancer regions".

There are various known methods of allowing a marker gene to be present at a position permitting expression control by the expression control region of an ECAT gene; the marker gene may be allowed to be present using any method well known to those skilled in the art. There are roughly two cases:

(1-1) a case where a marker gene is allowed to be present utilizing an individual (mouse), and (1-2) a case where a marker gene is allowed to be present in a cellular level without utilizing an individual. A detailed description is given below.

(1-1) Method of Allowing a Marker Gene to be Present Utilizing an Individual (Mouse)

When a marker gene is allowed to be present utilizing an individual (mouse), the marker gene is allowed to be present at a position on the genome for expression control by the expression control region of an ECAT gene. In this case, the ECAT gene present in the individual may be present in an expressible form, and may be present in a destroyed form.

The expression control region of a gene is normally present upstream of exon 1. Therefore, to ensure that a marker gene undergoes expression control by the expression control region of an ECAT gene, it is desirable that the marker gene be present downstream of the exon 1 initiation site of the ECAT gene. In this case, the marker gene may be present at any position, as long as it is downstream of the exon 1 initiation site.

(1-1-a) Cases where the ECAT Gene is Destroyed

Although any method well known to those skilled in the art may be used to destroy the ECAT gene, the most commonly used technique comprises targeted-destroying the ECAT gene by homologous recombination using a vector that harbors a marker gene, and that causes homologous recombination at an optionally chosen position in the ECAT gene (hereinafter referred to as targeting vector), to allow the marker gene to be present instead at that position. Thus destroying an ECAT gene and allowing a marker gene to be present at that position is referred to as "knocking in a marker gene to an ECAT gene".

Although there are various known methods of so knocking in a marker gene, the promoter trap method is suitably used out of them. The promoter trap method comprises inserting a targeting vector not harboring a promoter into a genome by homologous recombination, and allowing the expression of a marker gene by an endogenous promoter (the ECAT gene promoter) if homologous recombination has occurred accurately. Specific examples of the method of allowing a marker gene to be present at a position permitting expression control by the expression control region of an ECAT gene by the promoter trap method are given below.

First, the genome sequence of an ECAT gene required for targeting is determined. The genome sequence can be sequenced utilizing already publicly known sequence information, if available in, for example, the public database Mouse Genome Resources (http://www.ncbi.nlm.nih.gov/genome/guide/mouse/) and the like. If no sequence information is available, by screening a genome library available to those skilled in the art by PCR and the like using one of the ECAT genes shown by SEQ ID NO:1, 3, 5, 7, 9, 11, 13, 15, 17, 19, 21, 23, 25, 27, 29, 31, 33, 35 or 37 as a primer, it is possible to isolate a genomic clone comprising the genome region of desired ECAT gene, and to determine the genome base sequence. As examples of the genome library used here, the mouse BAC (bacterial artificial chromosome) library (Invitrogen), the PAC (P1-derived artificial chromosome) library (Invitrogen) and the like can be mentioned.

Next, on the basis of the genomic DNA sequence of the ECAT gene identified above, the genome region of the ECAT gene to be replaced by the marker gene is determined (hereinafter referred to as ECAT genome region A). The 5'-side region (5'-arm) and the 3'-side region (3'-arm) flanking this ECAT genome region A are amplified by performing PCR with genomic DNA as the template and the like. Here, as the genomic DNA serving as the template, the genomic DNA of a mouse BAC clone comprising an ECAT gene and the like can be mentioned. A primer for the PCR can be designed on the basis of the sequence of the aforementioned genomic DNA of the ECAT gene. The amplified 5'-arm and 3'-arm are inserted into respective sides flanking the marker gene cassette of the targeting vector for promoter trap. As examples of the targeting vector for promoter trap used here, pBSSK(−)-IRES-β geo, which comprises the IRES (internal ribosome entry site)-β geo (the fusion gene of the β galactosidase and neomycin resistance genes) cassette (Mountford P. et al., Proc. Natl. Sci. USA, 91:4303-4307 (1994)), a similar vector comprising the IRES-Hygro (hygromycin resistance gene) cassette and the like can be mentioned. Here, the IRES-Hygro cassette can be prepared by replacing the β geo portion of the aforementioned IRES-β geo cassette with Hygro (Invitrogen) and the like.

Next, the prepared targeting vector is linearized by digestion with restriction endonuclease, and this is introduced into ES cells by electroporation and the like.

As examples of the ES cells used for the introduction, ES cells such as RF8 cells (Meiner, V. et al., Proc. Natl. Acad. Sci. USA, 93: 14041-14046 (1996)), JI cells (Li, E. et al., Cell, 69:915-926 (1992)), CGR8 cells (Nichols, J. et al., Development, 110:1341-1348 (1990)), MG1.19 cells (Gassmann, M. et al., Proc. Natl. Acad. Sci., USA, 92:1292-1296 (1995)), and commercially available mouse ES cells 129SV (No. R-CMTI-1-15, R-CMTI-1A), mouse ES cells C57/BL6 (No. R-CMTI-2A), and mouse ES cells DBA-1 (No. R-CMTI-3A) (all available from Dainippon Pharmaceutical Co., Ltd.) and the like can be mentioned.

Introduction of the targeting vector to ES cells is performed by electroporation (see Meiner, V. et al., Proc. Natl. Acad. Sci. USA, 93: 14041-14046 (1996) and the like), the calcium phosphate method, the DEAE-dextran method, the electroporation method, the method using a lipid for transfection (Lipofectamine, Lipofectin; Invitrogen) and the like. Subsequently, ES cells incorporating the targeting vector are selected on the basis of the characteristics of the marker gene used (for example, drug resistance gene). The accurate occurrence of homologous recombination in the ES cells selected can be confirmed by Southern blot using a portion of the ECAT gene as the probe and the like. Thus, ES cells heterozygously comprising a gene resulting from knocking in a marker gene to the ECAT gene on the genome can be prepared.

For culturing ES cells, any medium known to those skilled in the art may be used. In the case of RF8 cells, for example, a medium of the composition: 15% FBS, 0.1 mM Non Essential Amino Acids (GIBCO BRL), 2 mM L-glutamine, 50 U/ml penicillin-streptomycin, 0.11 mM 2-ME (GIBCO BRL)/Dulbecco's Modified Eagle Medium (DMEM), and the like can be mentioned. A commercially available prepared medium (for example, No. R-ES-101 from Dainippon Pharmaceutical Co., Ltd. and the like) can also be used.

When feeder cells are used in the cultivation of ES cells, the feeder cells used may be fibroblasts prepared from a mouse embryo by a conventional method or cells of an STO cell line derived from a fibroblast (Meiner, V. et al., Proc. Natl. Acad. Sci. USA, 93: 14041-14046 (1996)), and may be a commercial product. As examples of the commercial product, feeder cells such as PMEF-N, PMEF-NL, PMEF-H, and PMEF-HL (all available from Dainippon Pharmaceutical Co., Ltd.) can be mentioned. It is desirable that the feeder cells be used for culturing the ES cells after their growth is stopped by mitomycin C treatment.

When the aforementioned feeder cells are not used in the cultivation of ES cells, the cultivation can be performed with the addition of an LIF (Leukemia Inhibitory Factor). As the LIF, mouse recombinant LIF, rat recombinant LIF (Nippon Chemi-Con Corporation and the like) and the like are used.

Next, ES cells comprising the aforementioned targeting vector are introduced into a mouse to prepare a knockout mouse (marker gene knock-in mouse). The method of preparing the marker gene knock-in mouse is well known to those skilled in the art. Specifically, a chimeric mouse is prepared by injecting the aforementioned ES cells to mouse (for example, C57BL/6 and the like) blastocysts, and transplanting the blastocysts into the uterus of a female mouse made to become pseudopregnant (ICR and the like). Subsequently, a heterozygous mutant mouse wherein a marker gene has been heterozygously knocked in is prepared by mating the chimeric mouse and an ordinary mouse (C57BL/6 and the like). By mating such heterozygous mutant mice, a homozygous mutant mouse wherein the marker gene has been homozygously knocked in is obtained.

The somatic cells used in the screening of the present invention may be somatic cells isolated from the aforementioned heterozygous mutant mouse, and may be somatic cells isolated from a homozygous mutant mouse. However, if an ECAT gene essential for the maintenance of the ES cell has been knocked out, it is necessary to use a somatic cell derived from a heterozygous mutant mouse in order to enable the step for converting somatic cells to ES-like cells and the maintenance of ES-like cells in the screening of the present invention. As an example of the ECAT gene essential for the maintenance of the ES cell, the ECAT4 gene (Mitsui, K., et al., Cell, 113: 631-642 (2003)) can be mentioned. On the other hand, when an ECAT gene not essential for the maintenance of the ES cells is knocked out, a somatic cell derived from a heterozygous mutant mouse may be used, and a somatic cell derived from a homozygous mutant mouse may be used. As the ECAT gene not essential for the maintenance of the ES cell, the ECAT2 gene, the ECAT3 gene, and the ECAT5 gene can be mentioned. That is, as shown in the literature (Tokuzawa, Y., et al., Molecular and Cellular Biology, 23(8): 2699-2708 (2003)) for the ECAT3 gene, as shown in the literature (Takahashi, K., et al., Nature, 423: 541-545 (2003)) for the ECAT5 gene, and as demonstrated for the first time in an Example below for the ECAT2 gene, these ECATs are factors that do not influence the maintenance of ES cells. Of these ECATs, the ECAT2 gene and the ECAT3 gene do not influence not only the maintenance but also the growth of ES cells; therefore, when a somatic cell derived from a homozygous mutant mouse is used, it is preferable to utilize a somatic cell derived from a homozygous mutant knock-in mouse wherein a marker gene has been knocked in to the ECAT2 gene or the ECAT3 gene.

Because the marker gene expression level is doubled by homozygously comprising a gene resulting from knocking in a marker gene to an ECAT gene, compared with the heterozygous case, this is advantageous in that the selection of cells expressing the marker is made accurate and easy. From this viewpoint, the ECAT2 gene and the ECAT3 gene are very useful targets.

Furthermore, by mating homozygous mutant mice of different ECAT genes, a double knock-in mouse can be prepared. For example, by mating a homozygous mutant mouse of the ECAT2 gene and a homozygous mutant mouse of the ECAT3 gene, a double knock-in mouse wherein both the ECAT2 gene and the ECAT3 gene have been replaced with a marker gene can be prepared. In this case, it is preferable that mutually different marker genes have been knocked in to each ECAT gene. In this case, because double selection with two different marker genes (for example, the neomycin resistance gene and the hygromycin resistance gene) is possible, the possibility of selecting false-positive ES-like cells in the screening of the present invention decreases, so that the likelihood of successful screening can be dramatically improved.

Specifically, somatic cells derived from a double knock-in mouse wherein the ECAT2 gene and the ECAT3 gene have been replaced with a marker gene, a double knock-in mouse wherein the ECAT2 gene and the ECAT4 gene have been replaced with a marker gene, a double knock-in mouse wherein the ECAT2 gene and the ECAT5 gene have been replaced with a marker gene, a double knock-in mouse wherein the ECAT3 gene and the ECAT4 gene have been replaced with a marker gene, a double knock-in mouse wherein the ECAT3 gene and the ECAT5 gene have been replaced with a marker gene, or a double knock-in mouse wherein the ECAT4 gene and the ECAT5 gene have been replaced with a marker gene, can be mentioned as examples. Preferably, a somatic cell derived from a double knock-in mouse wherein the ECAT2 gene and the ECAT3 gene have been homozygously replaced with a marker gene, can be mentioned.

(1-1-b) Cases where the ECAT Gene is Not Destroyed

As the technique for allowing a marker gene to be present at a position permitting expression control by the expression control region of the ECAT gene without destroying the ECAT gene, a technique utilizing a transgenic non-human animal prepared by introducing the BAC vector or PAC vector, wherein a marker gene is present at a position permitting expression control by the expression control region of the ECAT gene, and the like to an individual such as a mouse or rat can be mentioned. A description is given below for the BAC vector.

The BAC clone comprising the expression control region of an ECAT gene used here can be isolated and identified on the basis of the sequence information on the ECAT gene, as stated in (1-1-a) above. Replacement of a portion of the ECAT gene with a marker gene in the BAC clone comprising the ECAT gene can easily be performed using, for example, Red/ET Recombination (Gene Bridges). The expression control region of each ECAT gene is normally present upstream of the exon 1 of the ECAT gene. Therefore, to ensure that a marker gene undergoes expression control by the expression control region of the ECAT gene, it is desirable that the marker gene be present downstream of the exon 1 of the ECAT gene. In this case, the marker gene may be present at any position on the ECAT gene, as long as it is downstream of exon 1.

Methods of preparing a transgenic animal incorporating the thus-prepared BAC vector wherein a marker gene is present at a position permitting expression control by the expression control region of an ECAT gene (hereinafter also referred to as the BAC vector comprising a marker gene) are well known; the transgenic animal can be prepared on the basis of, for example, extra issue of Jikken Igaku "Shin Idenshi Kogaku Handbook, 3rd revised edition" (Yodosha Co., Ltd., 1999) and the like. A description of how to prepare a transgenic animal is given below for a mouse.

The method of introducing a gene into a mouse fertilized egg is not subject to limitation; the introduction is possible by the microinjection method, the electroporation method and the like. After the introduction, the egg obtained is cultured and transplanted to the oviduct of a pseudo-dam mouse, after which the recipient mouse is grown, and a desired pup mouse is selected from among the pup mice born. This selection can be performed by, for example, examining the DNA derived from the pup mouse for the presence or absence of the introduced gene by the dot blot hybridization method or the PCR method.

The aforementioned pup mouse and a wild mouse are mated to prepare a hetero-transgenic mouse (a mouse heterozygously comprising the introduced gene). By mating heterozygous mice, a transgenic mouse homozygously comprising the BAC vector comprising a marker gene can be obtained.

The somatic cells used in the screening of the present invention may be somatic cells isolated from the aforementioned hetero-transgenic mouse, and may be somatic cells isolated from a homo-transgenic mouse. Because the ECAT gene itself is expressed in this transgenic mouse, unlike in the case of the aforementioned knock-in mouse, it is unnecessary to take into consideration whether or not the ECAT gene used is essential to the maintenance of ES cells. Therefore, the somatic cells can be equally used for all ECAT genes (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene), and because the marker gene expression level is high, it is preferable to utilize a transgenic mouse homozygously comprising a marker gene.

Furthermore, a double transgenic mouse can be prepared by mating transgenic mice of different ECAT genes. In this case, the individual transgenic mice mated preferably comprise mutually different marker genes. In this case, because double selection with two different marker genes (for example, neomycin resistance gene and hygromycin resistance gene) is possible, the possibility of selecting false-positive ES-like cells in the screening of the present invention decreases, so that the likelihood of successful screening can be dramatically improved.

The somatic cells isolated from the above-described knock-in mouse or transgenic mouse may be any cells wherein the marker gene is not expressed (or is expressed at low expression levels). Specifically, cells other than totipotent cells such as ES cells can be mentioned; for example, (1) tissue stem cells (somatic stem cells) such as neural stem cells, hematopoietic stem cells, mesenchymal stem cells, and spermatogonial stem cells, (2) tissue progenitor cells, or (3) differentiated cells such as lymphocytes, epithelial cells, myocytes, fibroblasts can be mentioned. The cells can be isolated by a technique well known to those skilled in the art.

When ES cells have been isolated, they should be used after being deprived of their undifferentiated state and pluripotency by any technique (described below).

As described above, it becomes possible to easily prepare somatic cells from any tissue by maintaining somatic cells wherein a marker gene has been knocked in to an ECAT gene, or somatic cells incorporating a marker gene, at individual (mouse) levels, the aforementioned technique is a highly preferable method of supplying somatic cells.

(1-2) Method of Allowing a Marker Gene to be Present at Cellular Levels Without Utilizing an Individual There are various known methods of allowing a marker gene to be present at a position permitting expression control by the expression control region of an ECAT gene in cells without utilizing an individual; the marker gene may be allowed to be present using any method well known to those skilled in the art. Generally, a method of introducing a vector harboring a marker gene into cells can be mentioned.

The cells used for the transfection may be somatic cells or ES cells. The somatic cells used here may be somatic cells derived from any species such as mouse, human, or monkey. The somatic cells may be primary culture cells or an established line of cells; specifically, primary culture cells such as mouse embryoric fibroblasts (MEF), bone marrow derived mesenchymal stem cells, or spermatogonial stem cells, and established lines of cells like NIH3T3 and the like can be mentioned. As the ES cells, human or simian ES cells, as well as the mouse ES cells mentioned above, can be used. Here, as the human ES cells, KhES-1, KhES-2 or KhES-3 (all available from Stem Cell Research Center, Institute for Frontier Medical Sciences, Kyoto University) and the like can be mentioned; as the simian ES cells, cynomolgus monkey ES cells (Asahi Techno Glass Corporation) can be mentioned. When these ES cells are used in the screening of the present invention, they should be used after being deprived of their undifferentiated state and pluripotency by any technique.

For vector introduction into cells, an ordinary method of introduction suitable to the aforementioned host cell may be used. Specifically, the calcium phosphate method, the DEAE-dextran method, the electroporation method, the method using a lipid for transfection (Lipofectamine, Lipofectin; Invitrogen) and the like can be mentioned.

As the vector used for the introduction, the BAC vector and the PAC vector, which are vectors enabling cloning up to about 300-kb DNA, plasmid vectors, and the targeting vector described in (1-1) above and the like can be mentioned. Hereinafter described are methods of preparing a somatic cell wherein a marker gene is present at a position permitting expression control by the expression control region of an ECAT gene using each of these vectors.

(1-2-a) Cases where the BAC Vector or the PAC Vector is Used

By utilizing the BAC vector or PAC vector comprising the expression control region of an ECAT gene, it is possible to allow a marker gene to be present at a position permitting expression control by the expression control region of the ECAT gene. A description is given below for the BAC vector.

The BAC clone comprising the expression control region of an ECAT gene used here (hereinafter referred to as the BAC clone comprising an ECAT gene) can be isolated and identified on the basis of the sequence information on the ECAT gene, as stated in (1-1) above. Replacement of a portion of the ECAT gene with a marker gene in the BAC clone comprising the ECAT gene can easily be performed using, for example, Red/ET Recombination (Gene Bridges). The expression control region of each ECAT gene is normally present upstream of the exon 1 of the ECAT gene. Therefore, to ensure that a marker gene undergoes expression control by the expression control region of the ECAT gene, it is desirable that the marker gene be present downstream of the exon 1 initiation site of the ECAT gene. In this case, the marker gene may be present at any position, as long as it is downstream of the exon 1 initiation site.

By introducing the thus-prepared BAC vector wherein a marker gene is present at a position permitting expression control by the expression control region of the ECAT gene to a somatic cell, the cell can be provided as a somatic cell for the screening of the present invention. The BAC vector introduced here may be one kind of BAC vector, and may be two or more kinds of BAC vectors comprising different ECAT genes. To enable the easy selection of the cell incorporating the BAC vector in a selection medium, it is preferable that a gene comprising a drug resistance gene (hereinafter referred to as a second drug resistance gene) be inserted into the BAC vector. In this case, to enable the expression in the somatic cell, it is necessary that a promoter expressed in the somatic cell be added to the 5' side or 3' side of the second drug resistance gene. Although the second drug resistance gene may be the same kind of drug resistance gene as the marker gene present at a position permitting expression control by the expression control region of the ECAT gene, and may be a different kind of drug resistance gene, it is desirable that the second drug resistance gene be a different kind of drug resistance gene. When the same kind of drug resistance gene is used, it is possible to previously add the loxP sequence or FRT sequence to both ends of the second drug resistance gene, and select cells incorporating the BAC vector in a selection medium, and then cleaving out the second drug resistance gene with the recombinase Cre or FLP.

When a second drug resistance gene is not inserted into the BAC vector, unlike in the aforementioned case, a second expression vector harboring the second drug resistance gene may be co-transfected with the aforementioned BAC vector, and selection may be performed using a selection medium. In that case, it is desirable that the transfection be performed using the BAC vector in large excess compared with the second expression vector.

When the BAC vector wherein a marker gene is present at a position permitting expression control by the expression control region of the aforementioned ECAT gene has been introduced into ES cells, ES cells incorporating and expressing the marker gene can be selected on the basis of the properties of the marker gene used. Subsequently, by allowing the differentiation of the ES cells into somatic cells, the ES cells can be converted to a somatic cell used for the screening of the present invention. Because ES cells differentiate during culturing conditions without feeder cells, somatic cells obtained by differentiation under these conditions and somatic cells obtained by differentiation using a differentiation inducer known to those skilled in the art, such as retinoic acid, can be used for the screening of the present invention. Here, as examples of the somatic cells differentiated from ES cells, tissue stem cells, tissue progenitor cells, or somatic cells (nerve cells, dermal corneal cells, myocardial cells, skeletal muscle cells, blood cells, islet cells or pigment cells and the like) can be mentioned.

(1-2-b) Cases where a Promoter-Free Plasmid Vector is Used

By inserting the fusion gene of the expression control region of an ECAT gene and a marker gene into a promoter-free plasmid vector and transforming cells therewith, cells for the screening of the present invention can be prepared.

As examples of the vector used here, promoter-free plasmid vectors such as pBluescript (Stratagene) and pCR2.1 (Invitrogen) can be mentioned.

As examples of the expression control region of an ECAT gene used here, an about 1-kb portion, preferably an about 2-kb portion, upstream of the transcription initiation site of the gene can be mentioned.

The expression control region of each ECAT gene can be identified by, for example, a technique comprising (i) a step for determining the 5' end by an ordinary method such as the 5'-RACE method (performed using, for example, the 5' full Race Core Kit (manufactured by Takara Shuzo Co., Ltd.) and the like), the oligo cap method, or S1 primer mapping; and (ii) a step for acquiring a 5'-upstream region using the Genome Walker Kit (manufactured by CLONTECH Laboratories Japan, Ltd.) and the like, and determining the promoter activity of the upstream region obtained, and the like. By fusing a marker gene to the 3' side of the thus-identified expression control region of the ECAT gene, and inserting this into the aforementioned plasmid vector, a plasmid vector wherein the marker gene is present at a position for expression control by expression control region of the ECAT gene can be prepared.

By introducing the vector thus prepared into a somatic cell or ES cell in the same manner as (1-2-a) above, a somatic cell for the screening of the present invention can be prepared.

(1-2-c) Cases where a Targeting Vector is Used

By introducing the targeting vector described in (1-1) above into a somatic cell or ES cell, a somatic cell for the screening of the present invention can also be prepared.

When the aforementioned targeting vector is introduced into a somatic cell, it is more preferable to use a somatic cell obtained by allowing a gene comprising a drug resistance gene (second drug resistance gene) to be present on the targeting vector in the same manner as (1-2-a) above, or co-transfecting a second expression vector comprising a second drug resistance gene with the targeting vector, in order to enable the easy selection of cells incorporating the vector in a selection medium, and selecting using a selection medium, for the screening of the present invention. In the latter case, it is desirable that the transfection be performed using the aforementioned targeting vector in large excess compared with the second expression vector.

The aforementioned somatic cell may heterozygously comprise a gene resulting from knocking in a marker gene to an ECAT gene, and may homozygously comprise the same. When the ECAT4 gene is utilized, it is desirable that the aforementioned knock-in gene be heterozygously comprised; when the same is homozygously comprised, ECAT4 may be supplied into the cell at the time of screening. When the ECAT2 gene, ECAT3 gene or ECAT5 gene (particularly the ECAT2 gene or ECAT3 gene) is utilized, it is desirable that the aforementioned knock-in gene be homozygously comprised. A somatic cell homozygously comprising a gene resulting from knocking in a marker gene to an ECAT gene can be prepared by further introducing an additional knock-in gene (a targeting vector comprising a marker gene) into a somatic cell heterozygously comprising a knock-in gene (a targeting vector comprising a marker gene). The somatic cell can also be selected by culturing a somatic cell heterozygously comprising a knock-in gene in a selection medium comprising a high concentration of drug.

Furthermore, by introducing another knock-in gene (a gene wherein another ECAT gene has been knocked out) into a somatic cell homozygously comprising the aforementioned knock-in gene, a double knock-in cell similar to that obtained in (1-1) above can be prepared.

When the aforementioned targeting vector is introduced into ES cells, cells incorporating and expressing the marker gene can be selected on the basis of the properties of the marker gene on the targeting vector. The ES cells, like the aforementioned somatic cells, may also heterozygously comprise a gene resulting from knocking in a marker gene to an ECAT gene, and may also homozygously comprise the same. For the method of preparing homozygous mutant cells, refer to the method of preparing ECAT2 gene homozygous mutant ES cells described in Example 3 below. The method of inducing the conversion of ES cells to somatic cells is the same as (1-2-a) above. with a retroviral vector harboring the ECAT4 gene and allowed As described in the literature (Mitsui, K., et al., Cell, 113: 631-642 (2003)) and WO 2004/067744), ES cells wherein the ECAT4 gene has been homozygously mutated (ES cells wherein a marker gene has been knocked in to the ECAT4 gene) are known to no longer maintain undifferentiated state and pluripotency, hence to have differentiated. Although this cell was infected to normally express ECAT4 therein, ES cell functions (undifferentiated state and pluripotency) have not been restored.

Because ECAT4 is an essential factor for the maintenance of ES cell functions (undifferentiated state and pluripotency), cells that are ECAT4 homozygous mutant ES cells, to which ECAT4 has been supplied, can be said to be differentiated cells in a state similar to that of ES cells. Therefore, a screening system for bringing these cells into contact with a test substance is an efficient screening system enabling the easier identification of a nuclear reprogramming substance; the ECAT4 homozygous mutant ES cells used for such screening, and the cells to which ECAT4 has been supplied are somatic cells preferred for the present invention.

In the screening step (a) of the present invention, a somatic cell thus prepared and a test substance are brought into contact with each other.

The test substance (test sample) used here is not subject to limitation, and is exemplified by a nucleic acid, a peptide, a protein, an organic compound, an inorganic compound or a mixture thereof and the like; the screening of the present invention is specifically performed by bringing these test substances into contact with the aforementioned somatic cell. More specifically, as the test substance, a cell extract, a gene (genome, cDNA) library, an RNAi library, an antisense nucleic acid, a gene (genome, cDNA, mRNA), a protein, a peptide, a low molecular compound, a high molecular compound, a natural compound and the like can be mentioned. More specifically, the ES cell shown in Examples, egg, cell extract of ES cell or egg (extraction fraction), cDNA library, genome library or protein library derived from ES cells or egg, or growth factor and the like can be mentioned.

As a derivation for the cDNA library, protein library or cell extract (organic compound, inorganic compound and the like), undifferentiated cells such as ES cells or eggs are preferable, as described above, and ES cells wherein the NAT1 gene has been destroyed (knocked out) are particularly effective.

The NAT1 gene is a gene similar to the protein translation initiation factor eIF4G, and it has been reported that if the NAT1 gene is destroyed in ES cells, the undifferentiated state is enhanced compared with the normal condition (Yamanaka, S. et al., Embo J., 19, 5533-5541 (2000)). However, no association with nuclear reprogramming has been shown.

As described in Examples below, the present inventor fused an NAT1 gene knockout ES cell and a thymocyte derived from an ECAT3 knock-in mouse, and performed selection with G418; the incidence of ES-cell-like colonies was much higher than that obtained using a normal ES cell. This shows that NAT1 gene knockout ES cells are higher than normal ES cells in terms of not only the degree of undifferentiated state, but also reprogramming activity, and are considered to be very effective as a derivation for the cDNA library and the like used for the screening of the present invention.

Here, a cDNA library can be constructed using a commercially available cDNA library construction kit (for example, CloneMinor cDNA library construction kit (Invitrogen) or Creator SMART cDNA library construction kit (BD Biosciences) and the like). A protein library can be constructed with reference to WO 00/71580 and the like.

Note that the aforementioned cDNA library, protein library or cell extract and the like derived from NAT1 gene knockout ES cells can be effectively used not only in the screening of the present invention, but also in any functional screening for a nuclear reprogramming factor.

These test substances are brought into contact with somatic cells in an embodiment incorporatable into the somatic cells. For example, when the test sample is a nucleic acid (cDNA library and the like), it is introduced into a somatic cell using calcium phosphate, DEAE-dextran, a lipid for transfection or electric pulse and the like.

The conditions of contact of a somatic cell and a test substance are not subject to limitation, as long as they are culturing conditions (temperature, pH, medium composition and the like) that do not kill the cell, and that are suitable for the incorporation of the test substance.

Cell culture is performed under culture conditions for ES cell before, at, or after, the aforementioned contact of a somatic cell and a test substance. The cultivation of ES cells may be performed using any method known to those skilled in the art. In the case of RF8 cells, for example, a medium of the composition: 15% FBS, 0.1 mM Non Essential Amino Acids (GIBCO BRL), 2 mM L-glutamine, 50 U/ml penicillin-streptomycin, 0.11 mM 2-ME (GIBCO BRL)/Dulbecco's Modified Eagle Medium (DMEM), and the like can be mentioned. A commercially available prepared medium (for example, No. R-ES-101 from Dainippon Pharmaceutical Co., Ltd. and the like) can also be used.

When feeder cells are used in the cultivation of ES cells, the feeder cells used may be fibroblasts prepared from a mouse embryo by a conventional method or cells of an STO cell line derived from a fibroblast (Meiner, V. et al., Proc. Natl. Acad. Sci. USA, 93: 14041-14046 (1996)), and may be a commercial product. As examples of the commercial product, feeder cells such as PMEF-N, PMEF-NL, PMEF-H, and PMEF-HL (all available from Dainippon Pharmaceutical Co., Ltd.) can be mentioned. It is desirable that the feeder cells be used for culturing the ES cells after their growth is stopped by mitomycin C treatment.

When the aforementioned feeder cells are not used in the cultivation of ES cells, the cultivation can be performed with the addition of an LIF (Leukemia Inhibitory Factor). As the LIF, mouse recombinant LIF, rat recombinant LIF (Nippon Chemi-Con Corporation and the like) and the like can be mentioned.

Although the number of days for the aforementioned culture conditions for ES cell is variable as appropriate depending on cell condition and the like, it is preferably about 1 day to 3 days.

When a gene comprising a drug resistance gene is used as the marker gene, selection with a medium comprising the corresponding drug (selection medium) is performed. The drug may be contained in the medium at the time of contact of a somatic cell and a test substance, and may be contained after the contact. Furthermore, the aforementioned drug may be contained in the medium after cultivation under culture conditions for ES cell.

Following the aforementioned step, the presence or absence of the emergence of cells expressing the marker gene is determined, and a test substance allowing the emergence of the cells is elected as a somatic cell nuclear reprogramming substance candidate (step (b)). The step (b) is described below.

When the marker gene is a gene comprising a drug resistance gene, cells expressing the marker gene can be selected by cultivation using a selection medium as described above. Cells expressing the marker gene can be detected by observation using a fluorescence microscope when the marker gene is a fluorescent protein gene, by adding a luminescent substrate when the marker gene is a luminescent enzyme gene, and by adding a chromogenic substrate when the marker gene is a chromogenic enzyme gene.

If cells expressing the marker gene are detected compared with before addition of the test substance (including cases where the amount detected has increased), the test sample (test substance) used here is selected as a somatic cell nuclear reprogramming substance candidate.

The aforementioned screening can be repeatedly performed at any frequency as necessary. For example, when a mixture such as a cDNA library or a cell extract is used in the first screening, a somatic cell nuclear reprogramming factor candidate substance can finally be selected by repeatedly performing the same screening with the mixture divided (fractionated) in the second screening and beyond.

As an example of increasing the screening efficiency, a screening system wherein a test substance is added to fusion cells of somatic cells and ES cells is effective, rather than using the aforementioned somatic cells as is for the screening. Accordingly, the screening method of the present invention includes a screening method for a somatic cell nuclear reprogramming substance comprising the following steps (a) and (b):

(a) a step for bringing into contact with each other a fusion cell (somatic cell) of a somatic cell comprising a gene wherein a marker gene is present at a position permitting expression control by the expression control region of an ECAT gene and an ES cell, and a test substance, (b) a step following the aforementioned step (a), for determining the presence or absence of the emergence of cells expressing the marker gene, and selecting a test substance allowing the emergence of the cells as a somatic cell nuclear reprogramming substance candidate, "Fusion cells" as mentioned herein means fused cells of somatic cells and ES cells, wherein the aforementioned marker gene is not expressed (or is expressed at lower expression levels). If the number of colonies increases with the addition of a test substance compared with the number of ES-like-cell colonies resulting from fusion of somatic cells and ES cells, the test substance can be selected as a somatic cell nuclear reprogramming substance candidate.

As specific examples of the aforementioned screening method of the present invention, screening methods utilizing the ECAT2 gene, the ECAT3 gene, the ECAT4 gene and the ECAT5 gene, respectively, are described below; for all ECAT genes (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene), screening can be performed in the same manner with reference to the following description.

EXAMPLE 1

Screening Utilizing the ECAT2 Gene

As a specific example of the screening method of the present invention utilizing the ECAT2 gene, a screening method comprising the following steps (a) and (b):

(a) a step for bringing into contact with each other a somatic cell comprising a gene resulting from knocking in a gene comprising a drug resistance gene to the ECAT2 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate, can be mentioned.

As shown in an Example below, the ECAT2 gene is not an essential factor for the maintenance and growth of ES cells. Therefore, it is preferable to perform the screening of the present invention using a somatic cell resulting from homozygously knocking in a marker gene to the ECAT2 gene.

A knock-in mouse wherein a marker gene has been homozygously knocked in to the ECAT2 gene (ECAT2$^{\beta geo/\beta geo}$ mouse) can be prepared by, for example, the method described in Example 3 below. Somatic cells such as lymphocytes and skin cells are isolated from this ECAT2$^{\beta geo/\beta geo}$ mouse. A test substance is added to these somatic cells, the cells are cultured under culture conditions for ES cell (see, for example, Meiner, V. L., et al., Proc. Natl. Acad. Sci. USA, 93(24): p14041-14046 (1996)), and selected with G418 (0.25 mg/ml). If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

EXAMPLE 2

Screening Utilizing the ECAT3 Gene

As a specific example of the screening method of the present invention utilizing the ECAT3 gene, a screening method comprising the following steps (a) and (b):

(a) a step for bringing into contact with each other a somatic cell comprising a gene resulting from knocking in a gene comprising a drug resistance gene to the ECAT3 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate, can be mentioned.

As shown in an Example below, the ECAT3 gene is not an essential factor for the maintenance and growth of ES cells. Therefore, it is preferable to perform the screening of the present invention using a somatic cell wherein a marker gene has been homozygously knocked in to the ECAT3 gene.

A knock-in mouse wherein a marker gene has been knocked in to the ECAT3 gene (ECAT3$^{\beta geo/\beta geo}$ mouse) can be prepared by, for example, the method described in Example 1 below. Somatic cells such as lymphocytes and skin cells are isolated from this ECAT3$^{\beta geo/\beta geo}$ mouse. A test substance is added to these somatic cells, the cells are cultured under culture conditions for ES cell (see, for example, Meiner, V. L., et al., Proc. Natl. Acad. Sci. USA, 93(24): p14041-14046 (1996)), and selected with G418 (0.25 mg/ml). If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

EXAMPLE 3

Screening Utilizing the ECAT4 Gene

As a specific example of the screening method of the present invention utilizing the ECAT4 gene, a screening method comprising the following steps (a) and (b):

(a) a step for bringing into contact with each other a somatic cell comprising a gene resulting from knocking in a gene comprising a drug resistance gene to the ECAT4 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate, can be mentioned.

The ECAT4 gene is an essential factor for the maintenance and growth of ES cells. Therefore, the screening of the present invention is performed using a somatic cell wherein a marker gene has been heterozygously knocked in to the ECAT4 gene.

A knock-in mouse wherein a marker gene has been heterozygously knocked in to the ECAT4 gene (ECAT4$^{\beta geo/+}$ mouse) can be prepared by the method described in the literature (Mitsui, K., et al., Cell, 113: 631-642 (2003)) and the like, and the following method, described briefly below, can be mentioned.

A targeting vector for replacing the exon 2 of the mouse ECAT4 gene with the IRES-β geo cassette (Mountford et al., Proc. Natl. Acad. Sci. USA, 91:4303-4307 (1994)) is prepared as described below. A 5'-side arm is prepared by amplifying a 4-kb fragment comprising the intron 1 of ECAT4 by PCR with mouse genomic DNA as the template using primers (AGGGTCTGCTACTGAGATGCTCTG (SEQ ID NO:39) and AGGCAGGTCTTCAGAGGAAGGGCG (SEQ ID NO:40)). Also prepared is a 3'-side arm by amplifying a 1.5-kb fragment comprising exon 3-intron 3-exon 4 by PCR with mouse genomic DNA as the template using primers (CGGGCTGTAGACCTGTCTGCATTCTG (SEQ ID NO:41) and GGTCCTTCTGTCTCATCCTCGAGAGT (SEQ ID NO:42)). The 5'-side arm and the 3'-side arm are ligated to the IRES-β geo cassette to prepare a targeting vector. This targeting vector is cleaved with SacII and introduced by electroporation into RF8 ES cells (see Meiner et al., Proc. Natl. Acad. Sci USA, 93: 14041-14046 (1996)). Subsequently, a clone undergoing accurate homologous recombination is selected with a G418 selection medium. By injecting these ES cells undergoing homologous recombination with β geo into mouse blastocysts, a chimeric mouse is obtained, from which a heterozygous mutant mouse (ECAT4$^{\beta geo/+}$ mouse) is established.

Next, somatic cells such as lymphocytes and skin cells are isolated from this ECAT4$^{\beta geo/+}$ mouse. A test substance is added to these somatic cells, the cells are cultured under culture conditions for ES cell (see, for example, Meiner, V. L., et al., Proc. Natl. Acad. Sci. USA, 93(24): p14041-14046 (1996)), and selected with G418 is performed. If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

As another specific example of the aforementioned screening method of the present invention utilizing the ECAT4 gene, a screening method comprising the following steps (a) and (b):

(a) a step for supplying ECAT4 to a somatic cell comprising a gene resulting from knocking in a gene comprising a drug resistance gene to the ECAT4 gene, and bringing it into contact with a test substance, (b) a step following the aforementioned step (a), for determining the presence of absence of surviving cells in a selection medium, and selecting a test substance allowing the emergence of the surviving cells as a somatic cell nuclear reprogramming substance candidate, can be mentioned.

As described in the literature (Cell, 113: 631-642 (2003), WO 2004/067744), because ECAT4 is an essential factor for the maintenance of ES cell functions (undifferentiated state and pluripotency), a cell that is ECAT4 homozygous mutant ES cell, to which ECAT4 has been supplied, can be said to be a differentiated cell in a state similar to that of ES cells. Therefore, a screening system for bringing this cell into contact with a test substance is an efficient screening system enabling the easier identification of a nuclear reprogramming substance.

The ECAT4 homozygous mutant ES cell used here can be prepared by, for example, introducing the hygro vector (a targeting vector for replacing the ECAT4 gene with the Hygro vector) into the aforementioned ES cell undergoing homologous recombination with β geo (a heterozygous mutant cell wherein the β geo gene has been knocked in to the ECAT4 gene).

ECAT4 is supplied to this ECAT4 homozygous mutant ES cell (somatic cell). To effect the supply, an expression vector harboring the ECAT4 gene may be introduced into the cell and allowed to express, or the ECAT4 protein may be introduced in a form incorporatable into the cell (for example, in fusion with a protein like TAT).

At the same time as, or after, this introduction of ECAT4 (gene), a test substance is added, the cells are cultured under culture conditions for ES cell (see, for example, Meiner, V. L., et al., Proc. Natl. Acad. Sci. USA, 93(24): p14041-14046 (1996)), and selected with G418 and/or hygromycin. If surviving cells are observed in the selection, the test substance used here is selected as a somatic cell nuclear reprogramming substance candidate.

For example, when a cDNA library derived from ES cells is used as the test substance, the ECAT4 gene is first introduced into the aforementioned somatic cell (ECAT4 homozygous mutant ES cell). Subsequently, a cDNA pool derived from a cDNA library is transfected by a known technique such as the lipofectin method, and selection with G418 and/or hygromycin is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

EXAMPLE 4

Screening Utilizing the ECAT5 Gene

As a specific example of the screening method of the present invention utilizing the ECAT5 gene, a screening method comprising the following steps (a) and (b):

(a) a step for bringing into contact with each other a somatic cell comprising a gene resulting from knocking in a gene comprising a drug resistance gene to the ECAT5 gene, and a test substance, (b) a step following the aforementioned step (a), for determining the presence or absence of surviving cells in a selection medium, and selecting a test substance allowing the emergence of the surviving cells as a somatic cell nuclear reprogramming substance candidate, can be mentioned.

As shown in an Example below, the ECAT5 gene is not an essential factor for the maintenance of ES cells. Therefore, it is preferable to perform the screening of the present invention using a somatic cell wherein a marker gene has been homozygously knocked in to the ECAT5 gene.

A knock-in mouse wherein a marker gene has been homozygously knocked in to the ECAT5 gene (ECAT5$^{\beta geo/\beta geo}$ mouse) can be prepared by, for example, the method described in Example 2 below (Japanese Patent Kokai Publication No. 2003-265166). Somatic cells such as lymphocytes and skin cells are isolated from this ECAT5$^{\beta geo/\beta geo}$ mouse. A test substance is added to these somatic cells, the cells are cultured under culture conditions for ES cell (see, for example, Meiner, V. L., et al., Proc. Natl. Acad. Sci. USA, 93(24): p14041-14046 (1996)), and selected with G418 (0.25 mg/ml). If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

EXAMPLE 5

Screening Utilizing Two ECAT Genes

As described above, a double knock-in mouse can be prepared by mating homozygous mutant mice wherein a marker gene has been knocked in to two different ECAT genes, and a somatic cell derived from the mouse can be used for the screening. Specifically, a screening method using a somatic cell derived from a double knock-in mouse concerning a combination of the ECAT2 gene and the ECAT3 gene can be mentioned as an example. As a specific example of the screening method of the present invention utilizing the ECAT2 gene and the ECAT3 gene, a screening method comprising the following steps (a) and (b):
(a) a step for bringing into contact with each other a somatic cell comprising a gene resulting from knocking in a gene comprising a drug resistance gene to each of the ECAT2 gene and the ECAT3 gene, and a test substance,
(b) a step following the aforementioned step (a), for determining the presence or absence of surviving cells in a selection medium, and selecting a test substance allowing the emergence of the surviving cells as a somatic cell nuclear reprogramming substance candidate,
can be mentioned.

It is desirable that the drug resistance genes knocked in here be different from each other between the ECAT2 gene and the ECAT3 gene. In this case, because double selection with two different drug resistance genes (for example, neomycin resistance gene and hygromycin resistance gene) is possible, the possibility of selecting false-positive ES-like cells in the screening of the present invention decreases, so that the likelihood of successful screening can be dramatically improved.

A double knock-in mouse of the ECAT2 gene and the ECAT3 gene (ECAT2$^{Hygro/Hygro}$ ECAT3$^{\beta geo/\beta geo}$ mouse) can be obtained by mating the ECAT2$^{Hygro/Hygro}$ mouse and ECAT3$^{\beta geo/\beta geo}$ mouse prepared in Examples 1 and 3 below (but the drug resistance gene is the hygromycin resistance gene). Somatic cells such as lymphocytes and skin cells are isolated from this ECAT2$^{Hygro/Hygro}$ ECAT3$^{\beta geo/\beta geo}$ mouse. A test substance is added to these somatic cells, the cells are cultured under culture conditions for ES cell (see, for example, Meiner, V. L., et al., Proc. Natl. Acad. Sci. USA, 93(24): p14041-14046 (1996)), and selected with G418 (0.25 mg/ml) and hygromycin (0.1 mg/ml). If surviving cells are observed in this selection, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 and hygromycin is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

EXAMPLE 6

Screening Using Fusion Cells

A test substance is added to the aforementioned fusion cells of the somatic cells of the present invention and ES cells, the fused cells are cultured under culture conditions for ES cell (see, for example, Meiner, V. L., et al., Proc. Natl. Acad. Sci. USA, 93(24): p14041-14046 (1996)), and selected on the basis of the properties of a selection marker. If the number of colonies has increased with the addition of the test substance compared with the number of ES-like-cell colonies emerging as a result of fusion of somatic cells and ES cells, the test substance used here is selected as a somatic cell-nuclear reprogramming substance candidate.

For example, when a cDNA library derived from ES cells is used as the test substance and a drug resistance gene is used as the marker, a cDNA pool derived from a cDNA library is transfected to the aforementioned fusion cell of somatic cells and ES cells by a known technique such as the lipofectin method, and selection with a drug is performed by the aforementioned technique to determine the number of surviving cells. If the number of surviving cells (number of ES-like-cell colonies) has increased compared with a system to which the test substance has not been added, the cDNA pool is further divided into some pools and transfected to fusion cells (or somatic cells before the fusion). By repeating this experiment, a somatic cell nuclear reprogramming factor (candidate) derived from ES cells can finally be selected.

Whether or not the somatic cell nuclear reprogramming substance (candidate) selected by the screening of the present invention reprograms the nucleus of the somatic cell can be confirmed by determining (1) whether or not the ES-like-cell converted from a somatic cell by the nuclear reprogramming factor (candidate) is expressing an ES cell marker gene such as Oct3/4 or Ecat4 (Nanog), (2) whether or not the aforementioned ES cell differentiates in vitro with retinoic acid stimulation and the like, (3) whether or not a chimeric mouse is born after injection of the aforementioned ES cells into mouse blastocysts, and the like.

(2) Nuclear Reprogramming Substance of the Present Invention

The present invention provides a somatic cell nuclear reprogramming substance selected using the aforementioned screening method of the present invention. The nuclear reprogramming substance is a nucleic acid, a peptide, a protein, an organic compound, an inorganic compound or a mixture thereof. The ES cells used in Examples below are also among somatic cell nuclear reprogramming substances. Specifically, a gene or protein derived from ES cells can be mentioned as examples. As specific examples, a gene or protein derived from ES cells having the NAT1 gene destroyed can be mentioned. The nuclear reprogramming substance of the present invention is useful in stem cell therapy. Specifically, when somatic cells (tissue stem cells, differentiated cells and the like) are collected from a patient and the nuclear reprogramming substance of the present invention is added thereto, ES-like cells emerge. By allowing these ES-like cells to differentiate into nerve cells, myocardial cells or blood cells and the like using retinoic acid, growth factors (for example, EGF, FGF-2, BMP-2, LIF and the like), or glucocorticoid and the like, and returning these cells to the patient, stem cell therapy can be accomplished.

(3) New Application for the Knock-In Mouse of the Present Invention (Use as a Source of the Somatic Cell for the Screening of the Present Invention)

Traditionally, a knock-in mouse wherein a marker gene has been knocked in to a gene has been utilized for functional analysis of the gene. In some cases, such a knock-in mouse has served as a disease model animal. However, there has been no utilization as a source of the somatic cell used in the new screening method disclosed herein.

The present invention provides an application for a knock-in mouse comprising a gene resulting from knocking in a marker gene to an ECAT gene as a source of the somatic cell used in the screening of the present invention.

Regarding the method of preparing the knock-in mouse and the like, the same as described in detail in "(1) Screening method of the present invention" above and Examples below applies. The knock-in mouse preferably homozygously comprises a gene resulting from knocking in a marker gene to the gene, when the ECAT2 gene, the ECAT3 gene and/or the ECAT5 gene is used. When a gene resulting from knocking in a marker gene to the ECAT4 gene is used, the knock-in mouse preferably heterozygously comprises such the gene. As the marker gene, a drug resistance gene, a fluorescent protein gene, a luminescent enzyme gene, a chromogenic enzyme gene or a gene comprising a combination thereof can be mentioned. A gene comprising a drug resistance gene is particularly preferable.

(4) Somatic Cell of the Present Invention

The present invention provides a somatic cell comprising a gene wherein a marker gene is present at a position permitting expression control by the expression control region of an ECAT gene.

Regarding the method of preparing the somatic cell and the like, the same as described in detail in "(1) Screening method of the present invention for somatic cell nuclear reprogramming substance" above and Examples below applies. The somatic cell of the present invention is effectively used in the aforementioned screening method of the present invention or the ES-like cell selection method of the present invention described below.

(5) ES-Like Cell Selection Method of the Present Invention

The present invention also provides an ES-like cell selection method comprising the following steps (a) and (b):

(a) a step for bringing into contact with each other a somatic cell comprising a gene wherein a marker gene is present at a position permitting expression control by the expression control region of an ECAT gene, and a somatic cell nuclear reprogramming substance, (b) a step following the aforementioned step (a), for selecting cells expressing the marker gene as ES-like cells.

A somatic cell wherein a marker gene is present at a position permitting expression control by the expression control region of an ECAT gene as described with respect to the aforementioned screening method of the present invention is also effectively used for selecting ES-like cells. For example, it is desirable, with stem cell therapy in mind, that an ES-like cell emerging with stimulation of a human somatic cell with a nuclear reprogramming substance be separated (purified) from other cells (somatic cells), and used for subsequent treatment. Because the system of the present invention is a system enabling the easy selection of ES-like cells with the expression of a marker gene such as a drug resistance gene as the index, as described above, it can be effectively used in selecting and separating ES-like cells.

"ES-like cells" as mentioned herein means cells having ES cell properties, that is, cells having undifferentiated state and pluripotency.

The ES-like cell selection method of the present invention can be used for all purposes of selecting (separating) ES cells not only in the aforementioned treatment of humans, but also in various in vitro and in vivo studies concerning ES cells.

All of the aforementioned methods, namely 1) the method of preparing a somatic cell comprising a gene wherein a marker gene is present at a position permitting expression control by the expression control region of an ECAT gene, 2) the method of bringing into contact with each other the somatic cell and a somatic cell nuclear reprogramming substance, and 3) the method of selecting cells expressing the marker gene, are the same as those described in "(1) Screening method of the present invention for somatic cell nuclear reprogramming substance". When a gene comprising a drug resistance gene as the marker gene is used, cells expressing the marker gene can easily be selected (separated) by cultivation in a selection medium. When a fluorescent protein gene, a luminescent enzyme gene, or a chromogenic enzyme gene is used as the marker gene, the cell can be selected (separated) by utilizing a cell sorter, the limiting dilution method or the soft agar colony method and the like.

"The nuclear reprogramming substance" as mentioned above refers to a substance involved in somatic cell nuclear reprogramming as obtained in the aforementioned screening of the present invention. In Examples below, cells expressing the marker gene are selected as ES-like cells using ES cells themselves as a somatic cell nuclear reprogramming substance.

In the ES-like cell selection method of the present invention, any ECAT gene (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene) can be used. As a specific example, the following selection method can be mentioned.

Specifically, as the selection method utilizing the ECAT2 gene, an ES-like cell selection method comprising the following steps (a) and (b):

(a) a step for bringing into contact with each other a somatic cell comprising a gene wherein a drug resistance gene is present at a position permitting expression control by the expression control region of an ECAT2 gene, and a somatic cell nuclear reprogramming substance,
(b) a step following the aforementioned step (a), for selecting surviving cells in a selection medium as ES-like cells,
can be mentioned.

As the selection method utilizing the ECAT3 gene, an ES-like cell selection method comprising the following steps (a) and (b):
(a) a step for bringing into contact with each other a somatic cell comprising a gene wherein a drug resistance gene is present at a position permitting expression control by the expression control region of the ECAT3 gene, and a somatic cell nuclear reprogramming substance,
(b) a step following the aforementioned step (a), for selecting surviving cells in a selection medium as ES-like cells,
can be mentioned.

As the selection method utilizing the ECAT5 gene, an ES-like cell selection method comprising the following steps (a) and (b):
(a) a step for bringing into contact with each other a somatic cell comprising a gene wherein a drug resistance gene is present at a position permitting expression control by the expression control region of the ECAT5 gene, and a somatic cell nuclear reprogramming substance,
(b) a step following the aforementioned step (a), for selecting surviving cells in a selection medium as ES-like cells,
can be mentioned.

As the selection method utilizing the ECAT2 gene and the ECAT3 gene, an ES-like cell selection method comprising the following steps (a) and (b):
(a) a step for bringing into contact with each other a somatic cell comprising a gene wherein a drug resistance gene is present at positions permitting expression control by the expression control regions of the ECAT2 gene and the ECAT3 gene, and a somatic cell nuclear reprogramming substance,
(b) a step following the aforementioned step (a), for selecting surviving cells in a selection medium as ES-like cells,
can be mentioned.

As the selection method utilizing the ECAT4 gene, an ES-like cell selection method comprising the following steps (a) and (b):
(a) a step for bringing into contact with each other a somatic cell comprising a gene wherein a drug resistance gene is present at a position permitting expression control by the expression control region of the ECAT4 gene, and a somatic cell nuclear reprogramming substance,
(b) a step following the aforementioned step (a), for selecting surviving cells in a selection medium as ES-like cells,
can be mentioned.

It is desirable, with treatment of humans in mind, that the somatic cell used in the ES-like cell selection method described above be a human somatic cell comprising a vector harboring a marker gene inserted at a position permitting expression control by the expression control region of an ECAT gene. Specifically, a somatic cell prepared as described below is used.

Specifically, first, somatic cells are prepared by isolating a patient somatic cell from a human and the like. As the somatic cell, somatic cells involved in disease, somatic cells involved in disease treatment and the like can be mentioned. Any vector described in section (1-2) above is introduced into this human somatic cell. Specifically, it is desirable that the BAC vector (BAC vector wherein a marker gene is present downstream of the expression control region of an ECAT gene) or the PAC vector be introduced. The BAC vector (PAC vector) introduced here may be one kind of BAC vector, and may be two or more kinds of BAC vectors comprising different ECAT genes. By adding a nuclear reprogramming substance to this BAC vector-incorporating cell, ES-like cells are allowed to emerge. These ES-like cells are selected depending on the properties of the marker gene used. For example, when a drug resistance gene is used as the marker gene, ES-like cells can easily be selected with the drug resistance as the index by selection with a selection medium after addition of a nuclear reprogramming substance.

(6) ES-Like Cells of the Present Invention

The present invention provides cells (ES-like cells) expressing a marker gene emerging by the screening of the present invention for a somatic cell nuclear reprogramming substance, and ES-like cells selected by the ES-like cell selection method of the present invention. The ES-like cells can be effectively used in subsequent evaluations in vitro and in vivo. Specifically, examining the differentiation induction potential of the ES-like cells, the transplantation and survival of differentiation-induced cells to individuals (mouse and the like) and the like are of paramount importance in preliminary investigations of stem cell therapy in humans and various studies concerning ES cells. The ES-like cells of the present invention are effectively used in such studies and investigations.

Furthermore, by allowing the human cells expressing a marker gene (ES-like cells) obtained by the ES-like cell selection method of the present invention to differentiate into nerve cells, myocardial cells or blood cells and the like using retinoic acid, growth factors (for example, EGF, FGF-2, BMP-2, LIF and the like), or glucocorticoid and the like, and returning this to the patient, stem cell therapy can be achieved.

(6) Screening Method of the Present Invention for Substance for the Maintenance of Undifferentiated State and Pluripotency of ES Cells The present invention provides a screening method for a substance for the maintenance of undifferentiated state and pluripotency of ES cells, which comprises the following steps (a) and (b):
(a) a step for bringing an ES cell comprising a gene wherein a marker gene is present at a position permitting expression control by the expression control region of an ECAT gene, into contact with a test substance in a medium not allowing the maintenance of undifferentiated state and pluripotency of ES cells,
(b) a step following the aforementioned step (a), for determining the presence or absence of cells expressing the marker gene, and selecting a test substance allowing the occurrence of the cells as a candidate substance for the maintenance of undifferentiated state and pluripotency of ES cells.

When ES cells wherein a marker gene is present at a position permitting expression control by the expression control region of an ECAT gene are cultured in a medium not allowing the maintenance of ES cell properties (undifferentiated state and pluripotency), the expression of the marker gene disappears. On the other hand, if a substance for the maintenance of undifferentiated state and pluripotency of ES cells is present in the aforementioned medium, the expression of the marker gene persists. By utilizing this property, a substance (candidate) for the maintenance of undifferentiated state and pluripotency of ES cells can easily be screened.

The ES cell used in the aforementioned screening step (a) may be any ES cell, as long as it comprises a gene wherein a marker gene is present at a position permitting expression control by the expression control region of an ECAT gene. Specifically, for example, ES cells derived from the knock-in mouse described in (1-1-a) above, ES cells derived from the transgenic mouse described in (1-1-b) above, ES cells comprising the BAC vector or PAC vector described in (1-2-a) above, ES cells comprising the plasmid vector described in (1-2-b) above, or ES cells comprising the targeting vector described in (1-2-c) above can be mentioned. ES-like cells resulting from conversion of a somatic cell comprising a gene wherein a marker gene is present at a position permitting expression control by the expression control region of an ECAT gene as described above can also be used in the same way (hereinafter referred to as "ES cells", including ES-like cells).

"The medium not allowing the maintenance of undifferentiated state and pluripotency of ES cells" used in the aforementioned screening step (a) may be any medium, as long as it is a medium not allowing the maintenance of ES cell properties or a medium not allowing the maintenance of undifferentiated state. For example, because it is known that serum or feeder cells are essential for the maintenance of mouse ES cells (undifferentiated state and pluripotency maintenance) at low densities, the same conditions as the culture conditions for the ES cells, but deprived of serum or feeder cells or both, can be mentioned. Also, because feeder cells are essential for the maintenance of human ES cells (undifferentiated state and pluripotency maintenance), the same conditions as culture conditions for human ES cell, but deprived of feeder cells, can be mentioned. Furthermore, in the case of human ES cells, because cells that differentiate even in the presence of feeder cells emerge, the culture may be performed in the presence of feeder cells.

Specifically, the same conditions as the culture conditions for ES cell described in the literature (Meiner, V. L., et al., Proc. Natl. Acad. Sci. USA, 93(24): p14041-14046 (1996)), but deprived of serum or feeder cells or both, and the like can be mentioned as examples.

The aforementioned step (a) is performed by bringing the aforementioned ES cell into contact with a test substance in a medium not allowing the maintenance of undifferentiated state and pluripotency of ES cells. The test substance is brought into contact with the ES cell before, at, or after the ES cells are transferred to the medium not allowing the maintenance of undifferentiated state and pluripotency.

The test substance (test sample) used in this screening is not subject to limitation, and is exemplified by a nucleic acid, a peptide, a protein, an organic compound, an inorganic compound or a mixture thereof and the like; the screening of the present invention is specifically performed by bringing these test substances into contact with the aforementioned ES cell. As the test substance, a secretion product of cells, serum, a cell extract, a gene (genome, cDNA) library, an RNAi library, a nucleic acid (genome, cDNA, mRNA), an antisense nucleic acid, a low molecular compound, a high molecular compound, a protein, a peptide, a natural compound and the like can be mentioned. Specifically, animal serum or a fraction thereof, a secretion product of feeder cells or a fraction thereof and the like can be mentioned.

These test substances (test samples) are brought into contact with somatic cells in an embodiment incorporatable into the somatic cells. For example, when the test substance is a nucleic acid (cDNA library and the like), it is introduced into somatic cells using calcium phosphate, DEAE-dextran, or a lipid for transfection.

When a gene comprising a drug resistance gene as the marker gene is used, selection is performed with a medium comprising the corresponding drug (selection medium). The drug may be contained in the medium at the time of contact of the ES cell and the test substance, and may be contained after the contact. Furthermore, the aforementioned drug may be contained in the medium after cultivation in a medium not allowing the maintenance of undifferentiated state and pluripotency of ES cells in the presence of a test substance.

After the aforementioned step (a), the presence or absence of cells expressing the marker gene is determined, and a test substance allowing the occurrence of the cells is selected as a candidate substance for the maintenance of undifferentiated state and pluripotency of ES cells (step (b)). Regarding the step (b), the same as described in "(1) Screening method of the present invention for somatic cell nuclear reprogramming substance" above applies. If cells expressing the marker gene are observed, the test sample (test substance) used here is selected as a candidate substance for the maintenance of undifferentiated state and pluripotency of ES cells.

The aforementioned screening can be repeatedly performed at any frequency as necessary. For example, when a mixture such as a secretion product secreted of feeder cells or serum is used in the first screening, a candidate substance for the maintenance of undifferentiated state and pluripotency of ES cells can finally be selected by repeatedly performing the same screening with the mixture divided (fractionated) in the second screening and beyond.

Note that when screening is performed using a mixture as the test sample as described above, a substance that promotes the growth of ES cells is possibly be selected along with a substance for the maintenance of undifferentiated state and pluripotency of ES cells. Specifically, when a mixture (fraction A) is subjected to the aforementioned screening method of the present invention, and if surviving cells are confirmed and the number of the surviving cells increases, it is considered that the fraction contains a substance that promotes the growth of ES cells along with a substance for the maintenance of undifferentiated state and pluripotency of ES cells (of course there are some cases wherein a single substance has the properties of the two substances). In that case, the fraction A is further fractionated; if surviving cells are observed but the number of cells does not increase when one resulting fraction (fraction B) is subjected to the screening of the present invention, and also if no surviving cells are observed when the other resulting fraction (fraction C) is subjected to the screening of the present invention, it is considered that the fraction B contains a substance for the maintenance of undifferentiated state and pluripotency of ES cells, whereas the fraction C contains a substance that promotes the growth of ES cells. The screening of the present invention is also useful in selecting such a substance (candidate) that promotes the growth of ES cells.

As specific examples of the aforementioned screening method, screening methods utilizing the ECAT2 gene, the ECAT3 gene, the ECAT4 gene and the ECAT5 gene, respectively, are described below; for all ECAT genes (ECAT1 gene, ECAT2 gene, ECAT3 gene, ECAT4 gene, ECAT5 gene, ECAT6 gene, ECAT7 gene, ECAT8 gene, ECAT9 gene and Oct3/4 gene), screening can be performed in the same manner with reference to the following description.

EXAMPLE 1

Screening Utilizing the ECAT2 Gene

As a specific example of the screening method for a substance for the maintenance of undifferentiated state and pluripotency of ES cells utilizing the ECAT2 gene, a screening method comprising the following steps (a) and (b):
(a) a step for bringing an ES cell comprising a gene resulting from knocking in a gene comprising a drug resistance gene to the ECAT2 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells, can be mentioned.

As shown in an Example below, the ECAT2 gene is not an essential factor for the maintenance and growth of ES cells. Therefore, it is preferable to perform the screening of the present invention using ES cells wherein a marker gene has been homozygously knocked in to the ECAT2 gene. The ES cells can be prepared by, for example, the method described in Example 3 (ECAT2 gene homozygous mutant RF8 ES cell). These ES cells are cultured in the presence of a test substance under the same conditions as the culture conditions for ES cell described in the literature (Meiner, V. L., et al., Proc. Natl. Acad. Sci. USA, 93(24): p14041-14046 (1996)), but deprived of serum or feeder cells or both. Subsequently, selection with G418 and/or hygromycin is performed. If surviving cells are observed in the selection with these drugs, the test substance used here is selected as a candidate substance for the maintenance of undifferentiated state and pluripotency of ES cells.

For example, when a secretion product of feeder cells is used as the test substance, the secretion product of feeder cells is added to the aforementioned ES cells, and selection ith G418 and/or hygromycin is performed by the aforementioned technique to confirm the presence or absence of surviving cells. If surviving cells are identified, the secretion product is further divided into some fractions and added to ES cells. By repeating this experiment, a factor (candidate) for the maintenance of undifferentiated state and pluripotency of ES cells can finally be selected. Additionally, a substance (candidate) that promotes the growth of ES cells can also be selected with the increase in the number of viable cells as the index.

EXAMPLE 2

Screening Utilizing the ECAT3 Gene

As a specific example of the screening method for a substance for the maintenance of undifferentiated state and pluripotency of ES cells utilizing the ECAT3 gene, a screening method comprising the following steps (a) and (b):
(a) a step for bringing an ES cell comprising a gene resulting from knocking in a gene comprising a drug resistance gene to the ECAT3 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells, can be mentioned.

As shown in an Example below, the ECAT3 gene is not an essential factor for the maintenance and growth of ES cells. Therefore, it is preferable to perform the screening of the present invention using ES cells wherein a marker gene has been homozygously knocked in to the ECAT3 gene. Using these ES cells, ES cells wherein the ECAT3 gene has been homozygously mutated can be prepared by, for example, further introducing the Hygro vector (a targeting vector for replacing the ECAT3 gene with the Hygro gene) into the ES cells undergoing homologous recombination with the β geo vector, prepared in Example 1. These cells are cultured in the presence of a test substance under the same conditions as the ES cell culturing conditions described in the literature (Meiner, V. L., et al., Proc. Natl. Acad. Sci. USA, 93(24): p14041-14046 (1996)), but deprived of serum or feeder cells or both. Subsequently, selection with G418 and/or hygromycin is performed. If surviving cells are observed in the selection with these drugs, the test substance used here is selected as a candidate substance for the maintenance of undifferentiated state and pluripotency of ES cells.

For example, when a secretion product of feeder cells is used as the test substance, the secretion product of feeder cells is added to the aforementioned ES cells, and selection with G418 and/or hygromycin is performed by the aforementioned technique to confirm the presence or absence of surviving cells. If surviving cells are identified, the secretion product is further divided into some fractions and added to ES cells. By repeating this experiment, a factor (candidate) for the maintenance of undifferentiated state and pluripotency of ES cells can finally be selected. Additionally, a substance (candidate) that promotes the growth of ES cells can also be selected with the increase in the number of viable cells as the index.

EXAMPLE 3

Screening Utilizing the ECAT4 Gene

As a specific example of the screening method for a substance for the maintenance of undifferentiated state and pluripotency of ES cells utilizing the ECAT4 gene, a screening method comprising the following steps (a) and (b):
(a) a step for bringing an ES cell comprising a gene resulting from knocking in a gene comprising a drug resistance gene to the ECAT4 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells, can be mentioned.

The ECAT gene is an essential factor for the maintenance and growth of ES cells. Therefore, it is preferable to perform the screening of the present invention using ES cells wherein a marker gene has been heterozygously knocked in to the ECAT4 gene.

ES cells wherein a marker gene has been heterozygously knocked in to the ECAT4 gene can be prepared by introducing a targeting vector (for example, a targeting vector for replacing the ECAT4 gene with the β geo gene) into ES cells to cause homologous recombination as in the aforementioned cases of ECAT2 and ECAT3. These cells are cultured in the presence of a test substance under the same conditions as the culture conditions for ES cell described in the literature (Meiner, V. L., et al., Proc. Natl. Acad. Sci. USA, 93(24): p14041-14046 (1996)), but deprived of serum or feeder cells or both. Subsequently, selection with G418 is performed. If surviving cells are observed in the selection with G418, the test substance used here is selected as a candidate substance for the maintenance of undifferentiated state and pluripotency of ES cells.

For example, when a secretion product of feeder cells is used as the test substance, the secretion product of feeder cells is added to the aforementioned ES cells, and selection with G418 is performed by the aforementioned technique to confirm the presence or absence of surviving cells. If surviving cells are identified, the secretion product is further divided into some fractions and added to ES cells. By repeating this experiment, a factor (candidate) for the maintenance of undifferentiated state and pluripotency of ES cells can finally be selected. Additionally, a substance (candidate) that promotes the growth of ES cells can also be selected with the increase in the number of viable cells as an index.

EXAMPLE 4

Screening Utilizing the ECAT5 Gene

As a specific example of the screening method for a substance for the maintenance of undifferentiated state and pluripotency of ES cells utilizing the ECAT5 gene, a screening method comprising the following steps (a) and (b):
(a) a step for bringing an ES cell comprising a gene resulting from knocking in a gene comprising a drug resistance gene to the ECAT5 gene into contact with a test substance in a medium not allowing the maintenance of undifferentiated state and pluripotency of ES cells,
(b) a step following the aforementioned step (a), for determining the presence or absence of surviving cells in a selection medium, and selecting a test substance allowing the occurrence of the surviving cells as a candidate substance for the maintenance of undifferentiated state and pluripotency of ES cells,
can be mentioned.

As shown in an Example below, the ECAT5 gene is not an essential factor for the maintenance of ES cells. Therefore, it is preferable to perform the screening of the present invention using ES cells wherein a marker gene has been homozygously knocked in to the ECAT5 gene. The method of preparing the ES cell and the screening method using the same are the same as in the aforementioned cases of ECAT2 and ECAT3.

Whether or not the substance (candidate) for maintenance of undifferentiated state and pluripotency of ES cells selected by the aforementioned screening of the present invention maintains undifferentiated state and pluripotency of ES cells can be confirmed by culturing ES cells in a medium not allowing the maintenance of undifferentiated state and pluripotency of ES cells under culture conditions with the addition of the candidate substance, and examining various potentials thereof as ES cells. Specifically, this can be confirmed by, for example, determining (1) whether or not the ES cells cultured under the aforementioned culture conditions are expressing an ES cell marker gene such as Oct3/4 or Ecat4 (Nanog), (2) whether or not the aforementioned ES cells differentiate in vitro with retinoic acid stimulation and the like, (3) whether or not a chimeric mouse is born after injection of the aforementioned ES cells to mouse blastocysts, and the like.

(7) Substance of the Present Invention for the Maintenance of Undifferentiated State and Pluripotency of ES Cells The present invention provides a substance for the maintenance of undifferentiated state and pluripotency of ES cells selected using the aforementioned screening method. The substance for the maintenance of undifferentiated state and pluripotency of ES cells is any of a nucleic acid, a peptide, a protein, an organic compound, and an inorganic compound, and is preferably exemplified by a secretion product of feeder cells or a serum-derived component. The substance of the present invention for the maintenance of undifferentiated state and pluripotency of ES cells is useful in the clinical application of ES cells. Specifically, since it is essential to culture human ES cells or differentiated cells differentiated therefrom in a serum-free medium in the absence of feeder cells in clinical application, clinical application of the aforementioned ES cells is made possible by adding the substance of the present invention for the maintenance of undifferentiated state and pluripotency of ES cells to a serum-free medium.

(8) New Application for the Knock-In Mouse of the Present Invention (Use as a Source of the ES Cell for the Screening of the Present Invention)

The present invention provides an application for the knock-in mouse of the present invention as a source of the ES cell for screening for a substance for the maintenance of undifferentiated state and pluripotency of ES cells. The knock-in mouse of the present invention is as described in (3) above. Isolation of ES cells from a knock-in mouse can be performed by a technique well known to those skilled in the art.

(9) ES Cell of the Present Invention

The present invention provides an ES cell comprising a gene wherein a marker gene is allowed to be present at a position permitting expression control by the expression control region of an ECAT gene. The method of preparing the ES cell and the like are as described in detail in (1) and (6) above. The ES cell of the present invention is effectively used in a screening method for a substance for the maintenance of undifferentiated state and pluripotency of ES cells.

EXAMPLES

The present invention is hereinafter described specifically by means of the following Examples, which, however, are not to be construed as limiting the scope of the present invention.

Example 1

ES-like Cell Selection System Utilizing the ECAT3 Gene

A homozygous mutant knock-in mouse wherein the coding region of the ECAT3 gene had been replaced with the fusion gene of the β galactosidase and neomycin resistance genes (β geo) to knock out the ECAT3 gene, and wherein the expression of the ECAT3 gene had been made to permit monitoring by X-Gal staining and drug resistance (hereinafter ECAT3$^{\beta geo/\beta geo}$ mouse), was prepared. This ECAT3$\beta^{geo/\beta geo}$ mouse was prepared on the basis of the description in the literature (Tokuzawa, Y., et al., Molecular and Cellular Biology, 23(8): 2699-2708 (2003)). The procedure is briefly described below.

First, the BAC clone comprising the mouse ECAT3 gene was identified from a DNA pool of the BAC library (Research Genetics) by PCR screening using a portion of ECAT3 cDNA as the primer, and the base sequence thereof was determined.

Targeting vectors for replacing the exon 3 to exon 7 of the mouse ECAT3 gene with the IRES-β geo cassette (Mountford et al., Proc. Natl. Acad. Sci. USA, 91:4303-4307 (1994)) were prepared as described below. A 5'-side arm was prepared by amplifying a 1.4-kb fragment comprising the intron 1 to exon 3 of ECAT3 by PCR with the aforementioned mouse BAC DNA as the template using primers (ACCAAGGTCACCG-CATCCAA (SEQ ID NO:43) and CTTCACCAAGATTTC-CGATG (SEQ ID NO:44)). Also prepared was a 3'-side arm by amplifying a 3.5-kb fragment comprising exon 7 to exon 8 by PCR with mouse BAC DNA as the template using primers (GAATGGTGGACTAGCTTTTG (SEQ ID NO:45) and TGCCATGAATGTCGATATGCAG (SEQ ID NO:46)). The 5'-side arm and the 3'-side arm were ligated to the β geo cassette to prepare a targeting vector. This targeting vector was cleaved with NotI and introduced by electroporation into RF8 ES cells (Meiner et al., Proc. Natl. Acad. Sci USA, 93: 14041-14046 (1996)). A clone undergoing accurate homologous recombination was selected using a G418 selection medium. By injecting these ES cells undergoing homologous recombination with β geo into mouse (C57BL/6) blastocysts, a chimeric mouse was prepared, from which a heterozygous mutant mouse (ECAT3$^{\beta geo/+}$ mouse) was established; when such heterozygous mutant mice were mated, a homozygous mutant mouse (ECAT3$^{\beta geo/\beta geo}$ mouse) was born in accordance with Mendel's law.

Next, lymphocytes were collected from the thymus of an ECAT3$^{\beta geo/\beta geo}$ mouse by a conventional method. These cells were cultured under the culture conditions for ES cell described in the literature (Meiner, V. L., et al., Proc. Natl. Acad. Sci. USA, 93(24): p14041-14046 (1996)) for 2 days, and selection with G418 (0.25 mg/ml) was performed. As a result, all these lymphocytes died, with absolutely no drug resistant colony obtained. It was also confirmed that all normal ES cells died at this G418 concentration.

Figure 2:
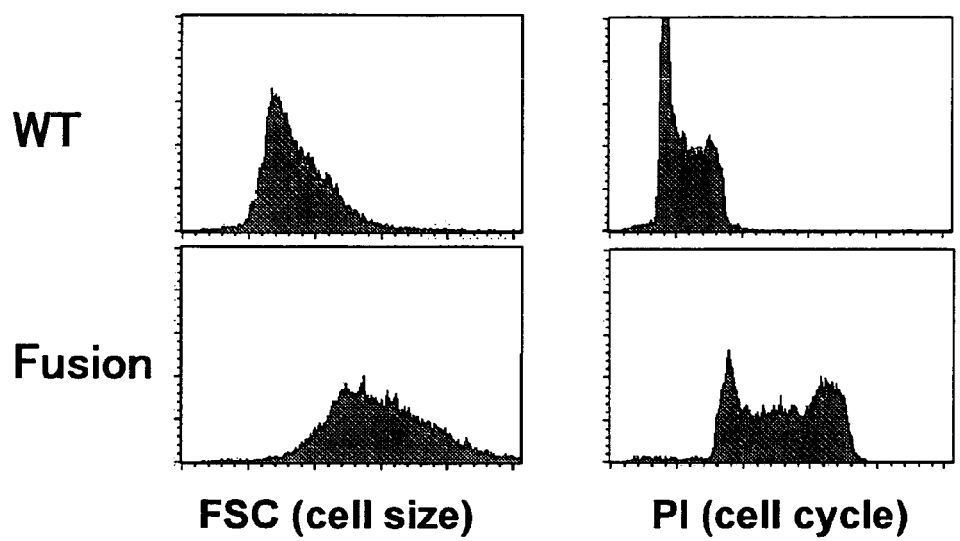
FIG. 2 is a drawing showing the results of an analysis by flow cytometry (FACS) of cells selected with G418 from among cells resulting from fusion of lymphocytes isolated from an ECAT3$^{\beta geo/\beta geo}$ mouse and normal ES cells. It is shown that the size (FSC) about doubled and the DNA content (PI) quadrupled in the fusion cells (Fusion in the figure) compared with the pre-fusion cells (WT in the figure).

Next, lymphocytes derived from an ECAT3$^{\beta geo/\beta geo}$ mouse and RF8 cells were electrically fused in accordance with the method of Tada et al. (Tada, M., et al., Curr. Biol., 11(19): p 1553-1558 (2001)), the resulting fusion cells were cultured on feeder cells (STO cells) under the aforementioned culture conditions for ES cell for 2 days, and selection was performed with G418 (0.25 mg/ml); a large number of ES-cell-like colonies were obtained. These colonies were isolated and cultured, and RNA was recovered. Because Northern blotting revealed that these cells expressed Oct3/4 or ECAT4 (Nanog) in all clones, and also because transplantation of these clones to mouse blastocysts resulted in the formation of a chimeric mouse, it was demonstrated that the cells selected with G418 were ES-like cells surely having ES cell properties (FIG. 1). Analysis of these cells by flow cytometry (FACS) showed that the size (Forward scatter) about doubled and the DNA content quadrupled (FIG. 2). From these results, it was found that these colonies had become resistant to G418 because lymphocyte nuclear reprogramming (conversion to ES cells) occurred as a result of fusion of lymphocytes derived from an ECAT3$^{\beta geo/\beta geo}$ mouse and normal ES cells. Hence, somatic cells derived from the ECAT3$^{\beta geo/\beta geo}$ mouse become drug-resistant only when converted to ES-like cells. Therefore, it was demonstrated that by utilizing this property, ES-like cells can be selected and a nuclear reprogramming factor that induces conversion to ES-like cells can easily be screened.

Example 2

ES-Like Cell Selection System Utilizing the ECAT5 Gene

A homozygous mutant knock-in mouse wherein the coding region of the ECAT5 gene had been replaced with β geo (ECAT5$^{\beta geo/\beta geo}$ mouse) was prepared on the basis of a method described in the literature (Takahashi, K., K. Mitsui, and S. Yamanaka, Nature, 423(6939): p541-545 (2003), Japanese Patent Unexamined Publication No. 2003-265166). Experiments were performed with the same protocol as described above using lymphocytes derived from this ECAT5$^{\beta geo/\beta geo}$ mouse. When 2×10$^6$ lymphocytes from the ECAT5$^{\oplus geo/\beta geo}$ mouse were fused with 4×10$^5$ ES cells and selection culture with G418 was performed, similar ES-cell-like colonies were obtained, though the number thereof was smaller than that obtained in the case of ECAT3 in Example 1. Hence, it was found that ECAT5 could likewise be utilized in an ES-like cell selection system.

Regarding the reason for the smaller number of colonies compared with the case of ECAT3, it was considered that because ECAT3 is not essential for the maintenance and growth of ES cells, whereas ECAT5 is a factor that promotes the growth of ES cells, despite the fact that the two share the feature of highly specific expression in ES cells, the reduction in the amount of the ECAT5 gene (knockout) serves unfavorably for conversion to ES cells.

Example 3

ES-Like Cell Selection System Utilizing the ECAT2 Gene

Figure 3:
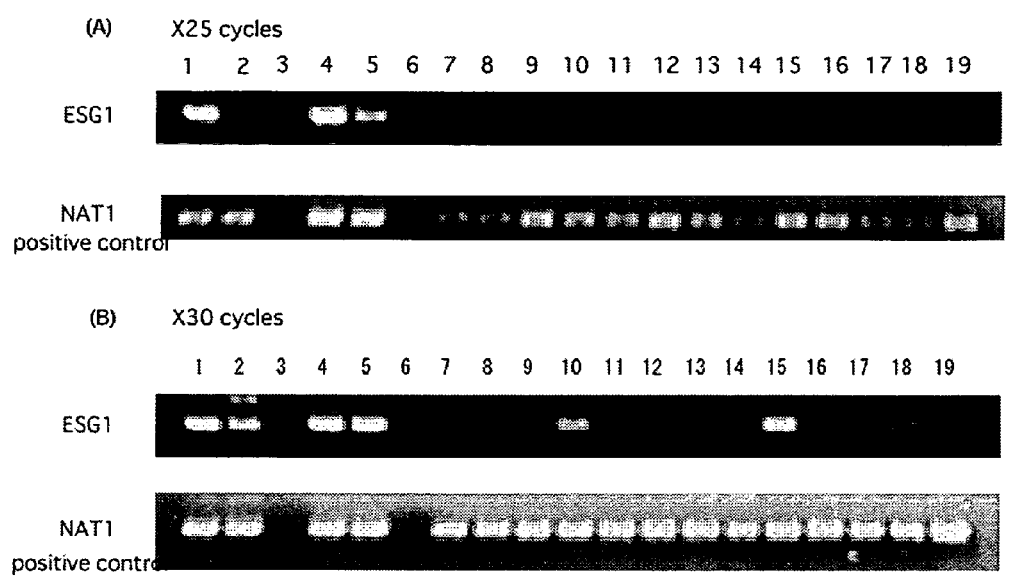
FIG. 3 is a drawing showing the results of an analysis by RT-PCR of the expression of the ECAT2 gene in various cells and tissues. (A) shows the results from 25 repeated cycles of amplification by RT-PCR; (B) shows the results from 30 repeated cycles. ESG1 shows the results for ECAT2; NAT1 shows the results for the positive control NAT1. The individual lanes show the expression of ECAT2 or NAT1 in the following cells and tissues: lane 1: undifferentiated MG1.19 cells, lane 2: differentiated MG1.19 cells, lane 3: RT-MG1.19 cells, lane 4: undifferentiated RF-8 cells, lane 5: differentiated RF-8 cells, lane 6: RT-RF-8 cells, lane 7: brain, lane 8: heart, lane 9: kidney, lane 10: testis, lane 11: spleen, lane 12: muscle, lane 13: lung, lane 14: stomach, lane 15: ovary, lane 16: thymus, lane 17: liver, lane 18: skin, lane 19: small intestine.

Specific expression of the ECAT2 gene in ES cells has already been shown by Northern blot analysis (see International Patent Publication No. WO 02/097090). Further extensive expressional analysis by RT-PCR confirmed specific expression in undifferentiated ES cells (FIG. 3A). When the cycle number was increased, expression occurred in the testis and ovary but absolutely no expression was observed in somatic tissue (FIG. 3B).

The mouse ECAT2 genome sequence was identified by the public database Mouse Genome Resources (http://www.ncbi.nlm.nih.gov/genome/guide/mouse/). A BAC clone comprising this ECAT2 genome was cloned by PCR and Southern hybridization.

A targeting vector for replacing exons 1 to 3 with β geo (fusion gene of the β galactosidase and neomycin resistance genes) or Hygro (hygromycin resistance gene) was prepared to knock out the ECAT2 gene. Specifically, a targeting vector designed to replace the exons 1 to 3 of the mouse ECAT2 gene with the IRES (internal ribosome entry site)-β geo cassette or the IRES-Hygro cassette was prepared.

Specifically, first, a fragment comprising the 5' flanking region to exon 1 region of the mouse ECAT2 genome and a fragment comprising the exon 3 to 3' flanking region were each amplified by PCR with the aforementioned BAC clone as the template, and these were used as the 5'-arm and 3'-arm, respectively, of the targeting vector. The 5'-arm was amplified using primers (CCGCGGAAAGTCAAGAGATTGGGTGG (SEQ ID NO:47) and GCGGCCGCCTTTACGGGTCAC-GAGGGTCAC (SEQ ID NO:48)), and the 3'-arm was amplified using primers (TGTGGCCAGTGTTTGGTTCTG-GCGGG (SEQ ID NO:49) and CTCGAGGACTCGCCATTCTAGCCAAG (SEQ ID NO:50)). By ligating the two amplified fragments to the IRES-β geo cassette or IRES-Hygro cassette of pBSSK(-)-IRES-β geo or pBSSK(-)-IRES-Hygro, a targeting vector was developed, and this was linearized by cleavage with SacII.

Figure 4:
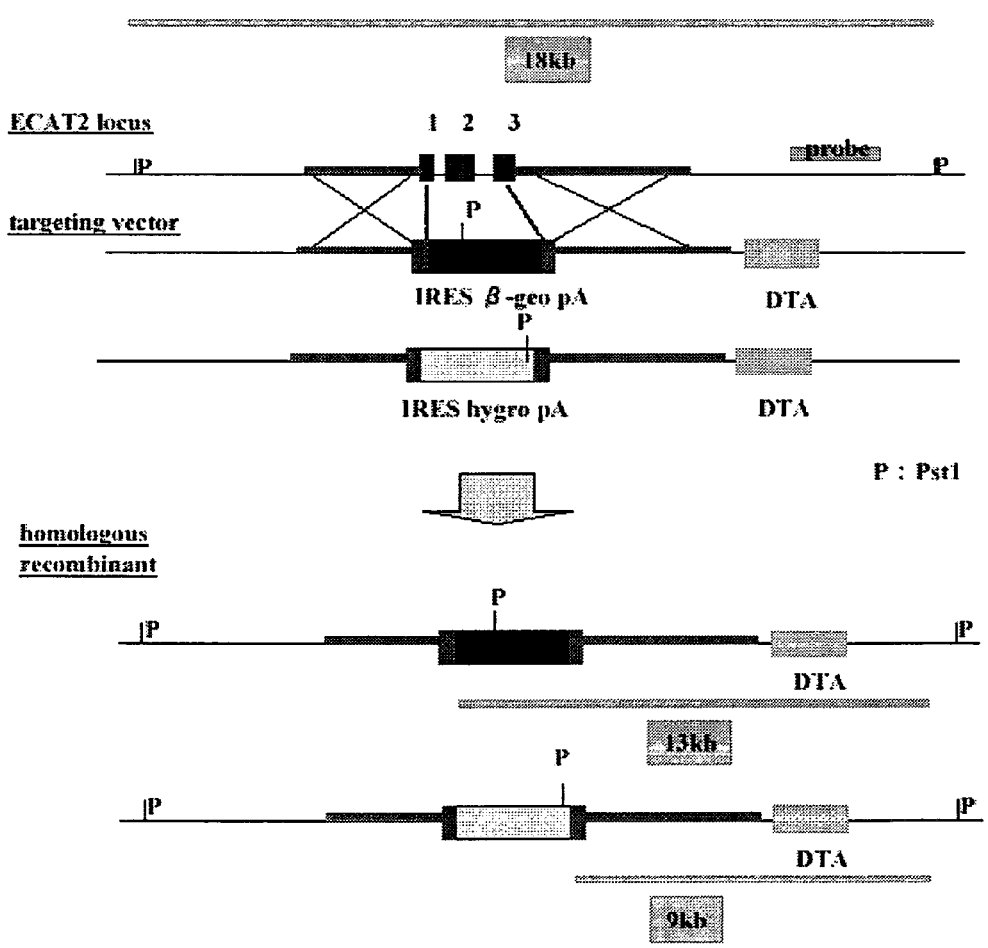
FIG. 4 is a drawing showing the targeting vector for knocking in β geo (the fusion gene of the β galactosidase and neomycin resistance genes) or Hygro (hygromycin resistance gene) to the ECAT2 gene, and the concept of destruction of the ECAT2 gene using it.

An outline of the destruction of the ECAT2 gene with the aforementioned targeting vector is shown in FIG. 4.

Figure 5:
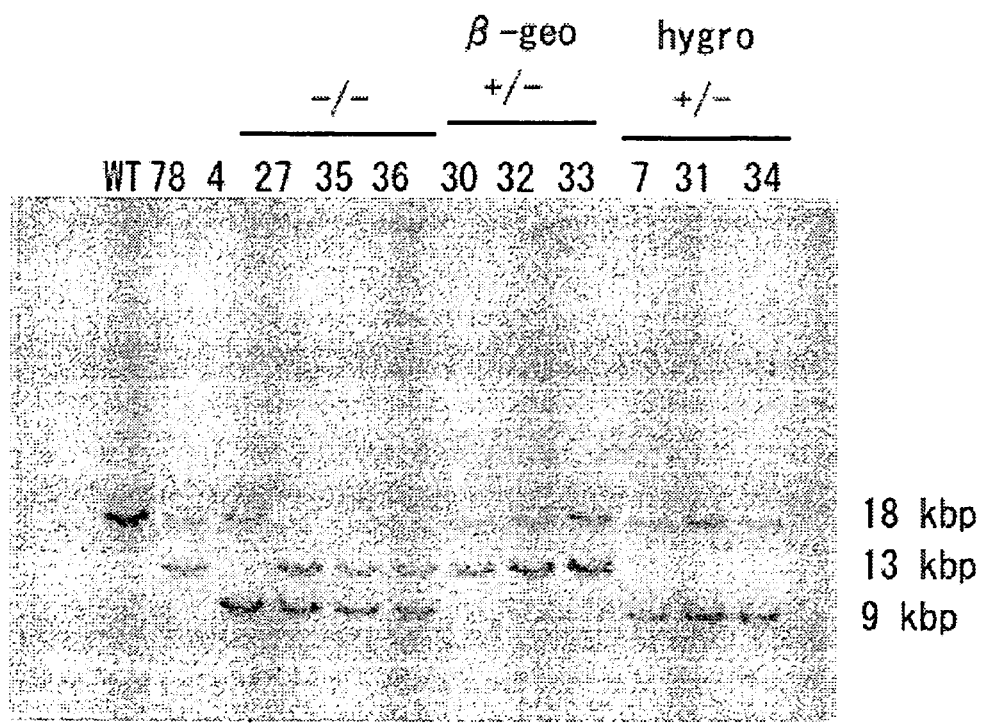
FIG. 5 is a drawing of a Southern blot analysis confirming the accurate occurrence of homologous recombination in the drug-resistant cells obtained by introducing a targeting vector into ES cells. In the figure, WT shows the results for ES cells not incorporating the vector. In the figure, –/– (lane Nos. 27, 35, and 36) shows the results for ECAT2 gene homozygous mutant ES cells wherein homologous recombination has occurred with both the β geo vector and the Hygro vector; β-geo +/– (lane Nos. 78, 30, 32, and 33) shows the results for ECAT2 gene heterozygous mutant ES cells wherein homologous recombination has occurred with the β geo vector; hygro +/– (lanes 4, 7, 31, and 34) shows the results for ECAT2 gene heterozygous mutant ES cells wherein homologous recombination has occurred with the Hygro vector.

The linearized targeting vector was introduced into RF8 ES cells (Meiner, V. et al., Proc. Natl. Acad. Sci. USA, 93: 14041-14046 (1996)) by electroporation, and selection was performed with each drug (neomycin (G418) for β geo, hygromycin for Hygro). Accurate occurrence of homologous recombination was confirmed by Southern blotting. Specifically, genomic DNA extracted from the aforementioned ES cell was cleaved with PstI, after which it was electrophoresed and transferred onto a nylon membrane. This was hybridized with the 3' region probe of the ECAT2 gene. An 18-kbp band is detected as emerging from the normal genome, a 13-kbp band is detected in homologous recombination with the β geo vector, and a 9-kbp band is detected in homologous recombination with the Hygro vector. The results are shown in FIG. 5. Accurate homologous recombination in each drug resistance ES cell was confirmed.

Figure 6:
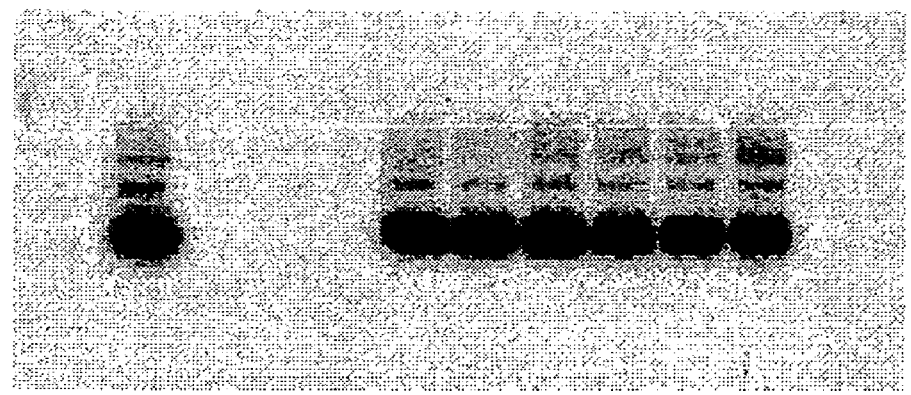
FIG. 6 is a drawing of a Northern blot analysis confirming the disappearance of the expression of the ECAT2 gene in ECAT2 gene homozygous mutant ES cells undergoing homologous recombination both with the β geo vector and with the Hygro vector. In the figure, the captions for the individual lanes are the same as FIG. 5. The upper panel is an autoradiogram showing the results of a Northern blot analysis; the lower panel shows a photograph of ribosomal RNA stained with ethidium bromide.
Figure 6:
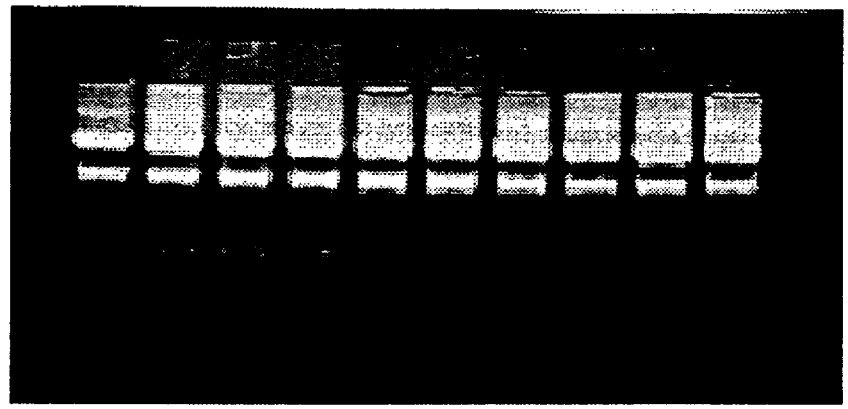

Furthermore, when the β geo vector was introduced into ES cells undergoing homologous recombination with the Hygro vector and selection with neomycin was performed, three clones of ES cells wherein homologous recombination with both vectors occurred, hence the ECAT2 gene were homozygously mutated. Accurate occurrence of homologous recombination with both the β geo vector and the Hygro vector was confirmed by Southern blotting in the same manner as described above (FIG. 5). Also, Northern blotting confirmed that these clones had lost the expression of ECAT2 (FIG. 6).

As a result of an examination to determine whether or not these homozygous mutant ES cells maintained ES cell functions, the cells were found to be normal in all of morphology, growth, and differentiation potential. From the results above, ECAT2 was found to be a factor that is specifically expressed in ES cells, testis, and ovary, but is not essential for the maintenance and initial development of ES. Thus, it was demonstrated that ECAT2, like the ECAT3 gene, could be highly effectively utilized for the selection of ES cells.

Next, by injecting ES cells undergoing homologous recombination with β geo into mouse (C57BL/6) blastocysts, a chimeric mouse was obtained, from which a heterozygous mutant mouse was established. Furthermore, when such heterozygous mutant mice were mated, a homozygous mutant mouse was born in accordance with Mendel's law. By performing experiments with the same protocol as Example 1 using somatic cells derived from this homozygous mutant mouse, ES-cell-like colonies can be obtained in the same manner as Example 1.

Specifically, when lymphocytes were collected from the thymus of an ECAT2$^{βgeo/βgeo}$ mouse by a conventional method, these lymphocytes and ES cells (RF8 cells) were fused using the same protocol as Example 1, and selection culture with G418 was performed, a large number of ES-cell-like colonies were obtained as in Example 1. Hence, it was found that ECAT2, like ECAT3, could be utilized for screening for a nuclear reprogramming factor and the like.

Example 4

Screening for Somatic Cell Nuclear Reprogramming Substance Using ECAT4 Homozygous Mutant ES Cells ES cells wherein the ECAT4 gene had been homozygously mutated (RF8 ES cells wherein the ECAT4 gene had been knocked in with both the β geo vector and the Hygro vector) were prepared on the basis of the literature (Mitsui, K., et al., Cell, 113: 631-642 (2003)) and WO 2004/067744). These ECAT4 homozygous mutant ES cells are known to no longer maintain undifferentiated state and pluripotency, hence to have differentiated (Cell, 113: 631-642 (2003), WO 2004/067744). When these cells were infected with a retroviral vector comprising the ECAT4 gene and allowed to normally express ECAT4 therein, ES cell functions (undifferentiated state and pluripotency) were not restored. From this result, it was demonstrated that nuclear reprogramming of differentiated ES cells could not be performed with ECAT4 alone.

Because ECAT4 is an essential factor for the maintenance of ES cell functions (undifferentiated state and pluripotency), as described in the literature (Cell, 113: 631-642 (2003), WO 2004/067744), the aforementioned ES cell, wherein ECAT4 has been knocked out and ECAT4 has been supplied, can be said to be a differentiated cell in a state similar to that of ES cells. Therefore, a screening system for bringing this cell into contact with a test substance was considered to be an efficient screening system enabling the easier identification of a nuclear reprogramming substance.

Screening for a somatic cell nuclear reprogramming substance using the aforementioned ECAT4 homozygous mutant ES cells is performed as described below.

First, an ECAT4 gene expression vector is introduced into the aforementioned ECAT4 homozygous mutant ES cell to supply ECAT4 to the cell. Next, a test substance is added, cell culture is performed under culture conditions for ES cell (see, for example, Meiner, V. L., et al., Proc. Natl. Acad. Sci. USA, 93(24): p14041-14046 (1996)), and selection with G418 and/or hygromycin is performed. If surviving cells are observed in the selection, the test substance used here is selected as a somatic cell nuclear reprogramming substance candidate.

For example, when a cDNA library derived from ES cells is used as the test substance, the ECAT4 gene is first introduced into the aforementioned somatic cell (ECAT4 homozygous mutant ES cell). Subsequently, a cDNA pool derived from a cDNA library is transfected by a known technique such as the lipofectin method, and selection with G418 and/or hygromycin is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

Figure 7:
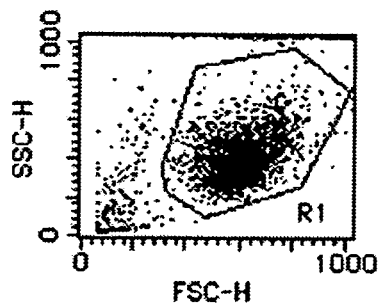
FIG. 7 is a drawing showing the results of an analysis of the fusion efficiency for normal ES cells (RF8) and thymocytes using a flow cytometer. Thymocytes derived from a mouse expressing a green fluorescent protein (EGFP) in the whole body (CAG-EGFP mouse) and normal ES cells were fused under two conditions involving DC 300 V and 500 V (RF8/T$^{CAG-EGFP}$ in the figure); on the following day, the ratio of cells becoming EGFP-positive due to the fusion was determined using a flow cytometer.
Figure 7:
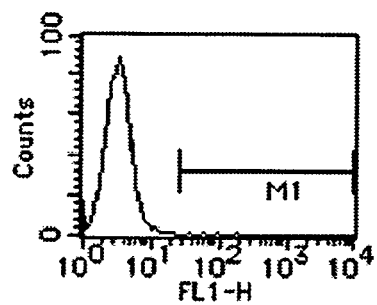
Figure 7:
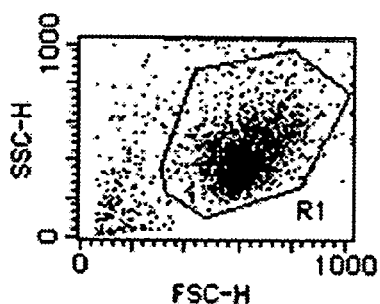
Figure 7:
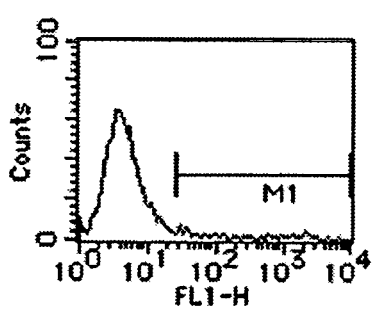
Figure 7:
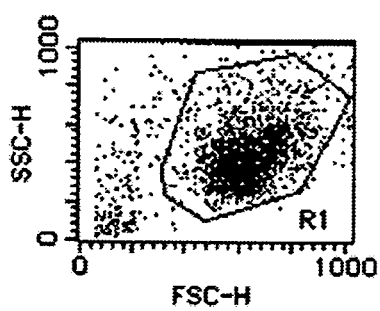
Figure 7:
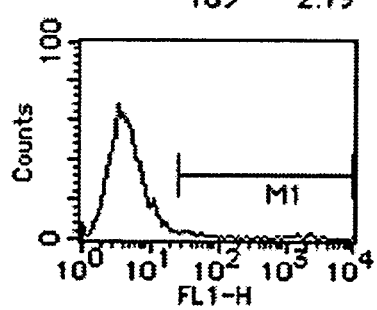
Figure 8:
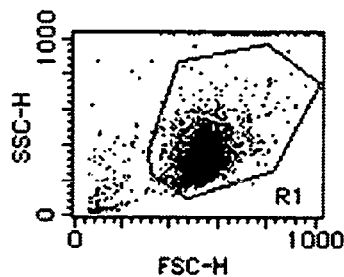
FIG. 8 is a drawing showing the results of an analysis of the fusion efficiency for NAT1 gene knockout ES cells and thymocytes using a flow cytometer. Using NAT1 gene knockout ES cells (NAT1$^{-/-}$ (neo/Cre); previously deprived of the neomycin resistance gene), experiments similar to those of FIG. 7 were performed.
Figure 8:
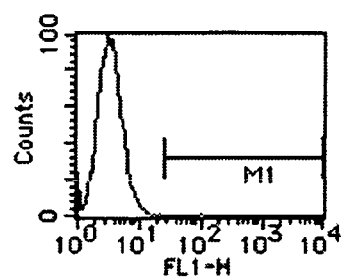
Figure 8:
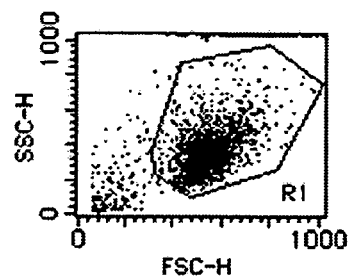
Figure 8:
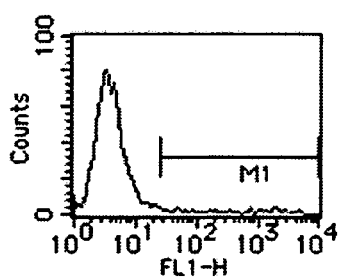
Figure 8:
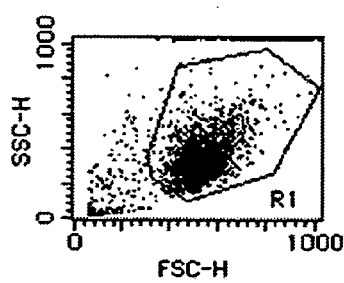
Figure 8:
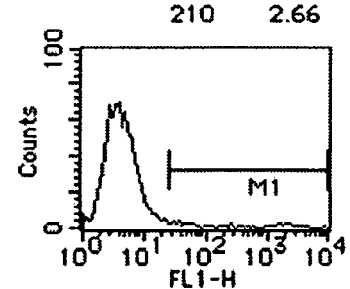
Figure 9:
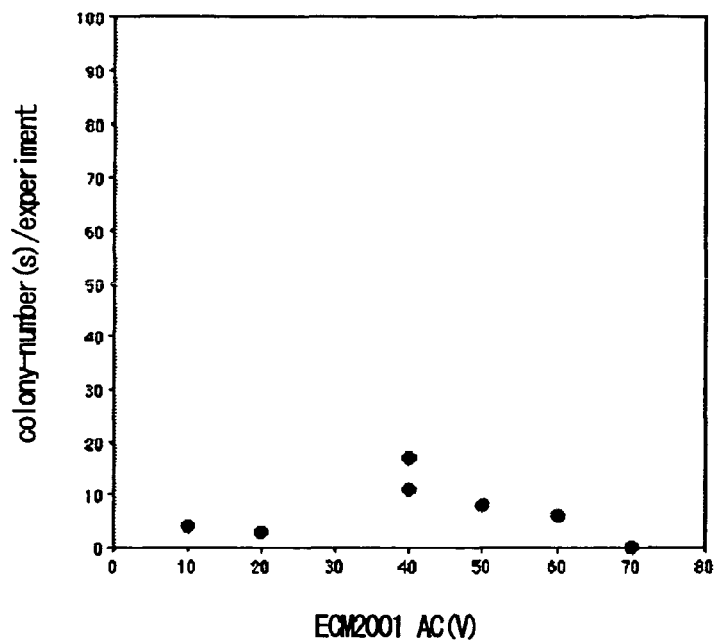
FIG. 9 is a graph showing the results of determinations of the nuclear reprogramming activities of normal ES cells and NAT1 gene knockout ES cells. Experiments of fusion of normal ES cells or NAT1 gene knockout ES cells and thymocytes derived from an ECAT3 knock-in mouse (Fbx15$^{-/-}$) were performed using various pulsation voltages. The number of ES-cell-like colonies emerging after selection with G418 was determined. The upper panel (RF8/T$^{Fbx15-/-}$) shows the results of a fusion experiment of RF8 and thymocytes derived from an ECAT3 knock-in mouse (Fbx15$^{-/-}$); the lower panel (NAT1$^{-/-}$(neo/Cre)/T$^{Fbx15-/-}$) shows the results of a fusion experiment of NAT1 gene knockout ES cells and thymocytes derived from an ECAT3 knock-in mouse (Fbx15$^{-/-}$). In the figure, the abscissa indicates pulsation voltage (V), and the ordinate indicates the number of ES-cell-like colonies emerging after selection with G418.
Figure 9:
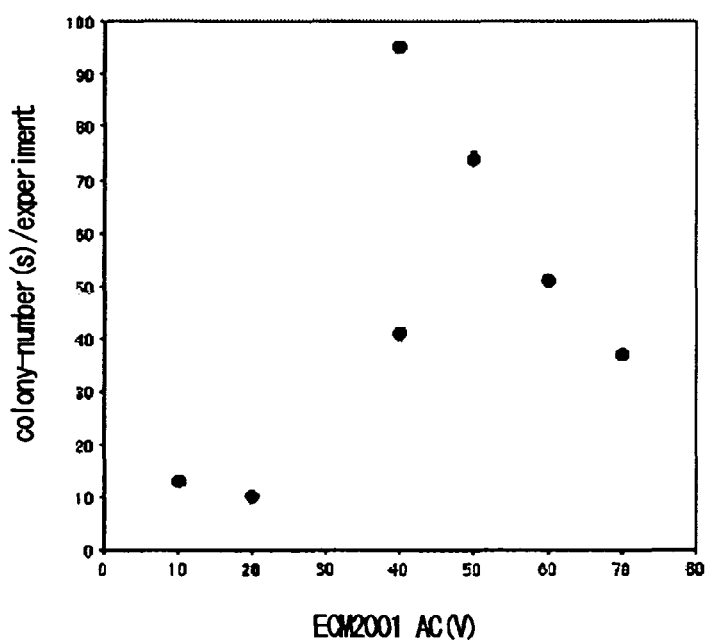

Example 5 cDNA Library as a Source for Search of Somatic Cell Nuclear Reprogramming Factor NAT1 gene knockout ES cells were prepared on the basis of the literature (Yamanaka, S. et al., Embo J., 19, 5533-5541 (2000). These ES cells are resistant to G418 because they were prepared using a targeting vector harboring the neomycin resistance gene. However, utilizing the fact that the neomycin resistance gene used is surrounded by two LoxP sequences, the neomycin resistance gene was removed by allowing the expression of the CRE gene by the same cells to establish NAT1 gene knockout ES cells having again become sensitive to G418. As a result of cell fusion of these cells with thymocytes derived from an ECAT3 knock-in mouse, no remarkable difference in fusion efficiency was observed compared with normal ES cells (FIGS. 7 and 8). However, the frequency of the emergence of ES-cell-like colonies after the selection with G418 increased significantly compared with the use of normal ES cells (FIG. 9). These results showed that the NAT1 gene knockout ES cells are higher than normal ES cells in terms of not only the degree of undifferentiated state, but also nuclear reprogramming activity, and are effective as a derivation for the cDNA library used for functional cloning of a nuclear reprogramming factor.

A cDNA library is constructed from NAT1 gene knockout ES cells using a commercially available cDNA library construction kit. Next, a cDNA pool derived from the aforementioned cDNA library is transfected to somatic cells derived from an DCAT3$^{βgeo/βgeo}$ mouse, an ECAT2$^{βgeo/βgeo}$ mouse and the like by a known technique such as the lipofectin method, and selection ith G418 is performed to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

Example 6

Screening for Somatic Cell Nuclear Reprogramming Substance Using Somatic Cells Derived from ECAT3$^{βgeo/βgeo}$ mouse Somatic cells such as lymphocytes and skin cells are isolated from an ECAT3$^{βgeo/βgeo}$ mouse. A test substance is added to these somatic cells, cell culture is performed under the culture conditions for ES cell described in the literature (Meiner, V. L., et al., Proc. Natl. Acad. Sci. USA, 93(24): p 14041-14046 (1996)) and the like, and selection with G418 (0.25 mg/ml) is performed. If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with-G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

Example 7

Screening for Somatic Cell Nuclear Reprogramming Substance Using Somatic Cells Derived from ECAT2$^{\beta geo/\beta geo}$ mouse Somatic cells such as lymphocytes and dermal cells are isolated from an ECAT2$^{\beta geo/\beta geo}$ mouse. A test substance is added to these somatic cells, cell culture is performed under the culture conditions for ES cell described in the literature (Meiner, V. L., et al., Proc. Natl. Acad. Sci. USA, 93(24): p14041-14046 (1996)) and the like, and selection with G418 (0.25 mg/ml) is performed. If surviving cells are observed in the selection with G418, the test substance used here is selected as a somatic cell nuclear reprogramming substance candidate.

For example, when a cDNA library derived from ES cells is used as the test substance, a cDNA pool derived from a cDNA library is transfected to the aforementioned somatic cell by a known technique such as the lipofectin method, and selection with G418 is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

Example 8

Screening for Somatic Cell Nuclear Reprogramming Substance Using Somatic Cells Derived from ECAT2$^{Hygro/Hygro}$-ECAT3$^{\beta geo/\beta geo}$ Double Knock-In Mouse An ECAT2$^{Hygro/Hygro}$-ECAT3$^{\beta geo/\beta geo}$ double knock-in mouse can be obtained by mating an ECAT2$^{Hygro/Hygro}$ mouse and an ECAT3$^{\beta geo/\beta geo}$ mouse. Somatic cells such as lymphocytes and skin cells are isolated from this double knock-in mouse. A test substance is added to these somatic cells, cell culture is performed under the culture conditions for ES cell described in the literature (Meiner, V. L., et al., Proc. Natl. Acad. Sci. USA, 93(24): p14041-14046 (1996)) and the like, and selection with G418 (0.25 mg/ml) and hygromycin (0.1 mg/ml) is performed. If surviving cells are observed in the selection with the two drugs, the test substance used here is selected as a somatic cell nuclear reprogramming substance candidate.

For example, when a cDNA library derived from ES cells is sed as the test substance, a cDNA pool derived from a cDNA library is transfected to the aforementioned somatic cell by a known technique such as the lipofectin method, and selection ith a drug is performed by the aforementioned technique to confirm the presence or absence of surviving cells. If surviving cells are identified, the cDNA pool is further divided into some pools and transfected to somatic cells. By repeating this experiment, a somatic cell nuclear reprogramming factor (candidate) derived from ES cells can finally be selected.

Example 9

Screening for Substance for the Maintenance of Undifferentiated State and Pluripotency of ES Cells Using ECAT2 Gene Homozygous Mutant ES Cells RF8 ES cells wherein the ECAT2 gene has been homozygously mutated, prepared in Example 3, are cultured in the presence of a test substance under the same conditions as the culture conditions for ES cell described in the literature (Meiner, V. L., et al., Proc. Natl. Acad. Sci. USA, 93(24): p14041-14046 (1996)), but deprived of serum or feeder cells or both.

Subsequently, selection with G418 (0.25 mg/ml) and/or hygromycin (0.1 mg/ml) is performed. If surviving cells are observed in the selection with these drugs, the test substance used here is selected as a candidate substance for the maintenance of undifferentiated state and pluripotency of ES cells.

For example, when a secretion product of feeder cells is used as the test substance, the secretion product of feeder cells is added to the aforementioned ES cells, and selection with G418 and/or hygromycin is performed by the aforementioned technique to confirm the presence or absence of surviving cells. If surviving cells are identified, the secretion product is further divided into some fractions and added to ES cells. By repeating this experiment, a factor (candidate) for the maintenance of undifferentiated state and pluripotency of ES cells can finally be selected.

Example 10

Screening for Substance for the Maintenance of Undifferentiated State and Pluripotency of ES Cells Using ECAT3 Gene Homozygous Mutant ES Cells The Hygro vector (a targeting vector for replacing the ECAT3 gene with the Hygro gene) is introduced into ES cells undergoing homologous recombination with the β geo vector, prepared in Example 1, to prepare RF8 ES cells wherein the ECAT3 gene has been homozygously mutated. These cells are cultured in the presence of a test substance under the same conditions as the culture conditions for ES cell described in the literature (Meiner, V. L., et al., Proc. Natl. Acad. Sci. USA, 93(24): p14041-14046 (1996)), but deprived of serum or feeder cells or both. Subsequently, selection with G418 (0.25 mg/ml) and/or hygromycin (0.1 mg/ml) is performed. If surviving cells are observed in the selection with these drugs, the test substance used here is selected as a candidate substance for the maintenance of undifferentiated state and pluripotency of ES cells.

For example, when a secretion product of feeder cells is used as the test substance, the secretion product of feeder cells is added to the aforementioned ES cells, and selection with G418 and/or hygromycin is performed by the aforementioned technique to confirm the presence or absence of surviving cells. If surviving cells are identified, the secretion product is further divided into some fractions and added to ES cells. By repeating this experiment, a factor (candidate) for the maintenance of undifferentiated state and pluripotency of ES cells can finally be selected.

INDUSTRIAL APPLICABILITY

According to the present invention, an efficient screening method for a somatic cell nuclear reprogramming substance is provided. Nuclear reprogramming substances are substances of paramount importance for realizing stem cell therapy; the screening method of the present invention enables early detection of such nuclear reprogramming substances. Furthermore, according to the present invention, an efficient screening method for substances for the maintenance of undifferentiated state and pluripotency of ES cells is provided. Substances for the maintenance of undifferentiated state and pluripotency of ES cells are substances of paramount importance for clinical application of ES cells; the screening method of the present invention enables early detection of such substances for the maintenance of undifferentiated state and pluripotency of ES cells.

SEQUENCE LISTING FREE TEXT

The base sequence shown in SEQ ID NO:39 is a primer.
The base sequence shown in SEQ ID NO:40 is a primer.
The base sequence shown in SEQ ID NO:41 is a primer.
The base sequence shown in SEQ ID NO:42 is a primer.
The base sequence shown in SEQ ID NO:43 is a primer.
The base sequence shown in SEQ ID NO:44 is a primer.
The base sequence shown in SEQ ID NO:45 is a primer.
The base sequence shown in SEQ ID NO:46 is a primer.
The base sequence shown in SEQ ID NO:47 is a primer.
The base sequence shown in SEQ ID NO:48 is a primer.
The base sequence shown in SEQ ID NO:49 is a primer.
The base sequence shown in SEQ ID NO:50 is a primer.

The invention claimed is:

1. A method of screening for a somatic cell nuclear reprogramming substance, which comprises the following steps (a) to (d):

(a) a step for providing an isolated somatic cell comprising a marker gene operably linked to the expression control region of an ECAT2 gene, wherein the ECAT2 gene encodes the amino acid sequence of SEQ ID NO: 6 or 8, (b) a step for bringing into contact a test substance with the somatic cell of the aforementioned step (a), (c) a step following the aforementioned step (b), for detecting the presence or absence of the emergence of cells expressing the marker gene, and (d) a step for selecting a test substance that allows the emergence of the cells as a candidate somatic cell nuclear reprogramming substance.

2. The screening method of claim 1, wherein the ECAT2 gene is an endogenous ECAT2 gene, and wherein the somatic cell is a mouse cell.

3. The screening method of claim 1, wherein the ECAT2 gene is an exogenous ECAT2 gene.

4. The screening method of claim 1, wherein the somatic cell homozygously comprises the marker gene.

5. The screening method of claim 1, wherein the marker gene is a drug resistance gene, a fluorescent protein gene, a luminescent enzyme gene, a chromogenic enzyme gene, or a gene comprising a combination thereof.

6. A method of screening for a somatic cell nuclear reprogramming substance, which comprises the following steps (a) to (d):
  (a) a step for providing an isolated somatic cell comprising a marker gene operably linked to the expression control region of an ECAT3 gene,
  (b) a step for bringing into contact a test substance with the somatic cell of the aforementioned step (a),
  (c) a step following the aforementioned step (b), for detecting the presence or absence of the emergence of cells expressing the marker gene, and
  (d) a step for selecting a test substance that allows the emergence of the cells as a candidate somatic cell nuclear reprogramming substance.

7. The screening method of claim 6, wherein the ECAT3 gene is an endogenous ECAT3 gene, and wherein the somatic cell is a mouse cell.

8. The screening method of claim 6, wherein the ECAT3 gene is an exogenous ECAT3 gene.

9. The screening method of claim 6, wherein the somatic cell homozygously comprises the marker gene.

10. The screening method of claim 6, wherein the marker gene is a drug resistance gene, a fluorescent protein gene, a luminescent enzyme gene, a chromogenic enzyme gene, or a gene comprising a combination thereof.

11. A method of screening for a somatic cell nuclear reprogramming substance, which comprises the following steps (a) to (d):
  (a) a step for providing an isolated somatic cell comprising
    (i) a first marker gene operably linked to the expression control region of an ECAT2 gene, wherein the ECAT2 gene encodes the amino acid sequence of SEQ ID NO: 6 or 8, and (ii) a second marker gene operably linked to the expression control region of an ECAT3 gene, wherein the first marker gene is different from the second marker gene,
  (b) a step for bringing into contact a test substance with the somatic cell of the aforementioned step (a),
  (c) a step following the aforementioned step (b), for detecting the presence or absence of the emergence of cells expressing the marker genes, and
  (d) a step for selecting a test substance that allows the emergence of the cells as a candidate somatic cell nuclear reprogramming substance.

12. The screening method of claim 11, wherein the ECAT2 is an endogenous gene and/or the ECAT3 gene is an endogenous gene, and wherein the somatic cell is a mouse cell.

13. The screening method of claim 11, wherein the ECAT2 and ECAT3 genes are exogenous genes.

14. The screening method of claim 11, wherein the somatic cell homozygously comprises the marker gene.

15. The screening method of claim 11, wherein each of the first and second marker genes is a drug resistance gene, a fluorescent protein gene, a luminescent enzyme gene, a chromogenic enzyme gene, or a gene comprising a combination thereof.

* * * * *